United States Patent [19]
Hilbert et al.

[11] Patent Number: 6,001,806
[45] Date of Patent: Dec. 14, 1999

[54] INTERFERON STIMULATING PROTEIN AND USES THEREOF

[75] Inventors: David M. Hilbert, Bethesda; Daniel P. Bednarik, Columbia; Bernadetta Nardelli, Gaithersburg, all of Md.; Marianne Murphy, Richmond, United Kingdom; David Parmelee, Rockville, Md.; Ann Gronowski, Ballwin; Robert Schreiber, St. Louis, both of Mo.

[73] Assignees: Humn Genome Sciences, Inc., Rockville, Md.; Washington University, St. Louis, Mo.

[21] Appl. No.: 09/105,039

[22] Filed: Jun. 26, 1998

Related U.S. Application Data

[60] Provisional application No. 60/051,053, Jun. 27, 1997.
[51] Int. Cl.$^6$ ........................................... A61K 38/10
[52] U.S. Cl. ...................... 514/12; 574/21; 574/2; 530/350; 530/324; 530/325
[58] Field of Search ...................... 530/350, 324, 530/325; 514/12, 2, 21

[56] References Cited

U.S. PATENT DOCUMENTS

| | | | |
|---|---|---|---|
| 5,750,383 | 5/1998 | Blissard et al. | 435/325 |
| 5,770,192 | 6/1998 | Cayley et al. | 424/93.2 |
| 5,846,714 | 12/1998 | Haskill et al. | 435/6 |
| 5,871,986 | 2/1999 | Boyce | 435/183 |

OTHER PUBLICATIONS

Whitford, M. et al., J. Of Virology, 63(3):1393–1399 (Mar. 1989)

Genbank entry, Accession No. AAA72760.

Genbank entry, Accession No. AAA66758.

*Primary Examiner*—Keith D. MacMillan
*Assistant Examiner*—T. D. Wessendorf
*Attorney, Agent, or Firm*—Kenley K. Hoover

[57] ABSTRACT

This invention relates to the use of the baculovirus glycoprotein, Interferon Stimulating Protein (ISP) (also known as gp67, gp64 EFP, or gp64), or the gene sequence encoding ISP, to stimulate production of interferon, such as for immunotherapy, anti-viral, anti-cancer, anti-bacterial, or anti-parasitic therapy. This invention also relates to novel mutant forms of ISP that show enhanced biological (i.e., anti-viral) activity, increased stability, higher yield or better solubility.

20 Claims, 15 Drawing Sheets

```
   1  ACATTTAATA TTGTCTATTA CGGTTTCTAA TCATACAGTA CAAAAATAAA ATCACAATTA    60
  61  ATATAATTAC AAAGTTAACT ACATGACCAA ACATGAACGA AGTCAATTTA GCGGCCAATT   120
 121  CGCCTTCAGC CATGGAAGTG ATGTCGCTCA GACTGGTGCC GACGCCGCCA AACTTGGTGT   180
 181  TCTCCATGGT GGTTATGAGG TTGCTTTTTT GTTGGGCAAT AAACGACCAG CCGCTGGCAT   240
 241  CTTTCCAACT GTCGTGATAG GTCGTGTTGC CGATGGTCGG GATCCAAAAC TCGACGTCGT   300
 301  GAATTGCAAG TTCCTTGTAG TTGCGAAAAT CTATGCATTG CGACGAGTCC GTGTTGGCCA   360
 361  CCCAACGCCC TTCTTTGTAG ATGCTGTTGT TGTAGCAATT ACTGGTGTGT GCCGGCGGAT   420
 421  TGGTGCACGG CATCAGCAAA AACGTGTCGT CCGACAAAAA TGTTGAAGAA ACAGAGTTGT   480
 481  TCATGAGATT GCCAATCAAA CGCTCGTCCA CCTTGGCCAC GGAGACTATC AGGTCGTGCA   540
 541  GCATATTGTT TAGCTTGTTG ATGTGCGCAT AATGTTCATT TTCAGCAAAT   600
 601  CGTTTTCGTA CATCAGCTCC TCTTGAATAT GCATCAGGTC GCCTTTGGTG GCAGTGTCTC   660
 661  CCTCTGTGTA CTTGGCTCTA ACGTTGTGGC GCCAAGTGGG CGGCCGCTTC TTGACTCGGT   720
 721  GCTCGACTTT GCGTTTAATG CATCGTTAA ACTTGCAGTT CGCGTGTCAC TTAGAAAGAT   780
 781  CATATATATC ATTGTCAATC AAACAGTGTT CGCGTGTGAC CGACTCGGGG TTATTTTTGT   840
 841  CATCTTTAAT GAGACAGACAC GCAGCTTTTA TTTGGCGCGT GGTGAACGTA GACTTTTGTT   900
 901  TGAGAATCAT ACTCACGCCG TCTCGATGAA GCACAGTGTC CACGGTCACG TTGATGGGGT   960
 961  GCCCTCAGCG TCCAAAATGT ATACCTGGCA CTCGTCCGTG TCGTCCTGGC ACTCGAGCCT  1020
1021  GCTGTACATT TTCGAAGTGG AAATGCCGCA TCGCCACCAA TTGTTGCACG TGTGGTGCGC  1080
1081  AAAGTGATTG TTATTCTGCC GCTTCACCAA CTCTTTGCCT TTGACCCACT GGCCGCGGCC  1140
1141  CTCGTTGTCG CGAAAACAGT CGTCGCTGTC ACTGCCCCAA CGGTCGATCA GCTCTTTCGCC  1200
1201  CACCTCGCAC TGCTGCCTGA TGCTCCACAT AAGCAAATCC TCTTTGCCCA GCCGTGGGT  1260
1261  TTTCATGGTT TCTTCGACGC GTGTGTTGGG ATCCAGGGAG CCGCGTTTGT ACGCATACGC  1320
1321  CTGGTAGTAC CCCTTGTAGC CGATAATCAC GTTTCGTTTG GGGCGGGGTA ATGTCCAAGT  1380
1381  GATTCCACAG TCCTTTCCTT GCGCGTTTGCA GCGCGTTGCA GTGCTCGCC GTGCTCCGCC  1440
1441  GTACGGACCC GTCTTCATTT GCGCGTTGCA GTGCTCCGCC GCAAAGGCAG AATGCGCCGC  1500
1501  CGCCGCCAAA AGCACATATA AAACAATAGC GCTTACCATC TTGCTTGTGT GTTCCTTATT  1560
      (SEQ ID NO:1)
```

FIG. 1A

```
  1  MVSAIVLYVL LAAAAHSAFA AEHCNAQMKT GPYKIKNLDI TPPKETLQKD VEITIVETDY   60
 61  NENVIIGYKG YYQAYAYNGG SLDPNTRVEE TMKTLNVGKE DLLMWSIRQQ CEVGEELIDR  120
121  WGSDSDDCFR DNEGRGQWVK GKELVKRQNN NHFAHHTCNK SWRCGISTSK MYSRLECQDD  180
181  TDECQVYILD AEGNPINVTV DTVLHRDGVS MILKQKSTFT TRQIKAACLL IKDDKNNPES  240
241  VTREHCLIDN DIYDLSKNTW NCKFNRCIKR KVEHRVKKRP PTWRHNVRAK YTEGDTATKG  300
301  DLMHIQEELM YENDLLKMNI ELMHAHINKL NNMLHDLIVS VAKVDERLIG NLMNNSVSST  360
361  FLSDDTFLLM PCTNPPAHTS NCYNNSIYKE GRWVANTDSS QCIDFRNYKE LAIHDVEFWI  420
421  PTIGNTTYHD SWKDASGWSF IAQQKSNLIT TMENTKFGGV GTSLSDITSM AEGELAAKLT  480
481  SFMFGHVVNF VIILIVILFL YCMIRNRNRQ Y                                 511

(SEQ ID NO:2)
```

FIG. 1B

```
    1 ACATTTAATA TTGTCTATTA CGGTTTCTAA TCATACAGTA CAAAAATAAA ATCACAATTA   60
   61 ATATAATTAC AAAGTTAACT ACATGACCAA ACATGAACGA AGTCAATTTA GCGGCCAATT  120
  121 CGCCTTCAGC CATGGAAGTG ATGTCGCTCA GACTGGTGCC GACGCCGCCA AACTTGGTGT  180
  181 TCTCCATGGT GGTTATGAGG TTGCTTTTTT GTTGGGCAAT AAACGACCAG CCGCTGGCAT  240
  241 CTTTCCAACT GTCGTGATAG GTCGTGTTGC CGATGGTCGG GATCCAAAAC TCGACGTCGT  300
  301 CGTCAATTGC TAGTTCCTTG TAGTTGCTAA AATCTATGCA TTGCGACGAG TCCGTGTTGG  360
  361 CCACCCAACG CCCTTCTTTG TAGATGCTGT TGTTGTAGCA ATTACTGGTG TGTGCCGGCG  420
  421 GATTGGTGCA CGGCATCAGC AAAAACGTGT CGTCCGACAA AAATGTTGAA GAAACAGAGT  480
  481 TGTTCATGAG ATTGCCAATC AAACGCTCGT CCACCTTGGC CACGGAGACT ATCAGGTCGT  540
  541 GCAGCATATT GTTAGCTTG TTGATGTGCG CATGCATCAG CTCAATGTTC ATTTTCAGCA  600
  601 AATCGTTTTC GTACATCAGC TCCTCTTGAA TATGCATCAG GTCGCCTTTG GTGGCAGTGT  660
  661 CTCCCTCTGT GTACTTGGCT CTAACGTTGT GGCGCCAAGT TAAACTTGCA TTCTTGACTC  720
  721 GGTGCTCGAC TTTGCGTTTA ATGCATCTGT GTTCGCGTGT CACCGACTCG TTTTTAGAAA  780
  781 GATCATATAT ATCATTGTCA ATCAAACAGT CGTGGTGAAC GTAGACTTTT  840
  841 TGTCATCTTT AATGAGCAGA CACGCAGCTT TTATTTGGCG GTCCACGGTC ACGTTGATGG  900
  901 GTTGAGAAT CATACTCACG CCGTCTCGAT GAAGCACAGT GTCGTCGTC TGGCACTCGA  960
  961 GGTTGCCCTC AGCGTCCAAA ATGTATACCT GGCACTCGTC CGTGTCGTCC TGGCACTCGA 1020
 1021 GCCTGCTGTA CATTTCGAA GTGGAAATGC CGCATCGCCA CGATTTGTTG CACGTGTGGT 1080
 1081 GCGCAAAGTG ATTGTTATTC TGCCGCTTCA CCAACTCTTT GCCTTTGACC CACTGGCCGC 1140
 1141 GGCCCTCGTT GTCGCGAAAA CAGTCGTCGC TGTCACTGCC CCAAGGGTCG ATCAGCTCTT 1200
 1201 CGCCCACCTC GCACTGCTGC CTGATGCTCC ACATAAGCAA ATCCTCTTTG CCCACATTCA 1260
 1261 GCGTTTTCAT GGTTTCTTCG ACGGTGTGT TGGGATCCAG TCACGTTTTC CGAGCCGCCG TTGTACGCAT 1320
 1321 ACGCCTGGTA GTACCCCTTG TAGCGCGTTT TCACGTTTTC CCTTGGGCGG GTTGTAGTCC GTCTCCACGA 1380
 1381 TGGTGATTTC CACGTCCTTT TGCAGGCGTT CCTTGGGCGG GGTAATGTCC AAGTTTTTAA 1440
 1441 TCTTGTACGG ACCGTCTTC ATTTGCGGT TATAAAACAA TAGCGCTTAC CATCTTGCTT GCAGAATGCG 1500
 1501 CCGCCGCCGC CAAAAGCACA TIGGTGTGAC TATAAACAA TAGCGCTTAC CATCTTGCTT GTGTGTTCCT 1560
 1561 TATTGAAGCC TTGGTGTGAC TGATTTACTA GTAGCATTGA GGCAT                  1605
      (SEQ ID NO:3)
```

FIG.1C

```
  1  MLLVNQSHQG FNKEHTSKMV SAIVLYVLLA AAAHSAFAAE HCNAQMKTGP YKIKNLDITP   60
 61  PKETLQKDVE ITIVETDYNE NVIIGYKGYY QAYAYNGGSL DPNTRVEETM KTLNVGKEDL  120
121  LMWSIRQQCE VGEELIDRWG SDSDDCFRDN EGRGQWVKGK ELVKRQNNNH FAHHTCNKSW  180
181  RCGISTSKMY SRLECQDDTD ECQVYILDAE GNPINVTVDT VLHRDGVSMI LKQKSTFTTR  240
241  QIKAACLLIK DDKNNPESVT REHCLIDNDI YDLSKNTWNC KFNRCIKRKV EHRVKKRPPT  300
301  WRHNVRAKYT EGDTATKGDL MHIQEELMYE NDLLKMNIEL MHAHINKLNN MLHDLIVSVA  360
361  KVDERLIGNL MNNSVSSTFL SDDTFLLMPC TNPPAHTSNC YNNSIYKEGR WVANTDSSQC  420
421  IDFSNYKELA IDDDVEFWIP TIGNTTYHDS WKDASGWSFI AQQKSNLITT MENTKFGGVG  480
481  TSLSDITSMA EGELAAKLTS FMFGHVVNFV IILIVILFLY CMIRNRNRQY              530
(SEQ ID NO:4)
```

FIG. 1D

N-terminal sequence of ISP

```
     1          10    cycles sequenced
     |...........|
     aNILAVFPtp    30%
     AEHCNAQMKT    60%
```

Data:

```
     AEHCNAQMKT    60%
     ::::::::::
     AEHCNAQMKT
```

Identities:

```
     aNILAVFPtp    30%
     ::::::::::
     ANILAVFPTPAYS    UDP-glucosyl transferase
``` gp 67-envelope glycoprotein
Autographa californica

FIG.6

* BEYOND SCALE OF ELISA

IL-12 = 1 ng/ml
PHA = 2 ug/ml
ANTI-IL-12 = 10 ug/ml
BOILED = 20 min, 100 °C

RESULTS ARE MEANS ± SD OF QUADRUPLICATE
WELLS FROM SUPERNATANTS DILUTED 1:3

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
(A) LENGTH: 1560 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:1:

```
ACATTTAATA TTGTCTATTA CGGTTTCTAA TCATACAGTA CAAAAATAAA ATCACAATTA     60

ATATAATTAC AAAGTTAACT ACATGACCAA ACATGAACGA AGTCAATTTA GCGGCCAATT    120

CGCCTTCAGC CATGGAAGTG ATGTCGCTCA GACTGGTGCC GACGCCGCCA AACTTGGTGT    180

TCTCCATGGT GGTTATGAGG TTGCTTTTTT GTTGGGCAAT AAACGACCAG CCGCTGGCAT    240

CTTTCCAACT GTCGTGATAG GTCGTGTTGC CGATGGTCGG GATCCAAAAC TCGACGTCGT    300

GAATTGCAAG TTCCTTGTAG TTGCGAAAAT CTATGCATTG CGACGAGTCC GTGTTGGCCA    360

CCCAACGCCC TTCTTTGTAG ATGCTGTTGT TGTAGCAATT ACTGGTGTGT GCCGGCGGAT    420

TGGTGCACGG CATCAGCAAA AACGTGTCGT CCGACAAAAA TGTTGAAGAA ACAGAGTTGT    480

TCATGAGATT GCCAATCAAA CGCTCGTCCA CCTTGGCCAC GGAGACTATC AGGTCGTGCA    540

GCATATTGTT TAGCTTGTTG ATGTGCGCAT GCATCAGCTC AATGTTCATT TTCAGCAAAT    600

CGTTTTCGTA CATCAGCTCC TCTTGAATAT GCATCAGGTC GCCTTTGGTG GCAGTGTCTC    660

CCTCTGTGTA CTTGGCTCTA ACGTTGTGGC GCCAAGTGGG CGGCCGCTTC TTGACTCGGT    720

GCTCGACTTT GCGTTTAATG CATCTGTTAA ACTTGCAGTT CCACGTGTTT TTAGAAAGAT    780

CATATATATC ATTGTCAATC AAACAGTGTT CGCGTGTCAC CGACTCGGGG TTATTTTTGT    840

CATCTTTAAT GAGCAGACAC GCAGCTTTTA TTTGGCGCGT GGTGAACGTA GACTTTTGTT    900

TGAGAATCAT ACTCACGCCG TCTCGATGAA GCACAGTGTC CACGGTCACG TTGATGGGGT    960
```

-continued

```
GCCCTCAGCG TCCAAAATGT ATACCTGGCA CTCGTCCGTG TCGTCCTGGC ACTCGAGCCT    1020

GCTGTACATT TTCGAAGTGG AAATGCCGCA TCGCCACGAT TTGTTGCACG TGTGGTGCGC    1080

AAAGTGATTG TTATTCTGCC GCTTCACCAA CTCTTTGCCT TTGACCCACT GGCCGCGGCC    1140

CTCGTTGTCG CGAAAACAGT CGTCGCTGTC ACTGCCCCAA CGGTCGATCA GCTCTTCGCC    1200

CACCTCGCAC TGCTGCCTGA TGCTCCACAT AAGCAAATCC TCTTTGCCCA CATTCAGCGT    1260

TTTCATGGTT TCTTCGACGC GTGTGTTGGG ATCCAGCGAG CCGCCGTTGT ACGCATACGC    1320

CTGGTAGTAC CCCTTGTAGC CGATAATCAC GTTTTCGTTG TAGTCCGTCT CCACGATGGT    1380

GATTTCCACG TCCTTTTGCA GCGTTTCCTT GGGCGGGGTA ATGTCCAAGT TTTTAATCTT    1440

GTACGGACCC GTCTTCATTT GCGCGTTGCA GTGCTCCGCC GCAAAGGCAG AATGCGCCGC    1500

CGCCGCCAAA AGCACATATA AACAATAGCG CTTACCATCT TGCTTGTGT GTTCCTTATT    1560
```

(2) INFORMATION FOR SEQ ID NO:2:

(i) SEQUENCE CHARACTERISTICS:
        (A) LENGTH: 511 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Val Ser Ala Ile Val Leu Tyr Val Leu Leu Ala Ala Ala His
  1               5                  10                  15

Ser Ala Phe Ala Ala Glu His Cys Asn Ala Gln Met Lys Thr Gly Pro
             20                  25                  30

Tyr Lys Ile Lys Asn Leu Asp Ile Thr Pro Pro Lys Glu Thr Leu Gln
         35                  40                  45

Lys Asp Val Glu Ile Thr Ile Val Glu Thr Asp Tyr Asn Glu Asn Val
 50                  55                  60

Ile Ile Gly Tyr Lys Gly Tyr Tyr Gln Ala Tyr Ala Tyr Asn Gly Gly
 65                  70                  75                  80

Ser Leu Asp Pro Asn Thr Arg Val Glu Glu Thr Met Lys Thr Leu Asn
                 85                  90                  95

Val Gly Lys Glu Asp Leu Leu Met Trp Ser Ile Arg Gln Gln Cys Glu
            100                 105                 110

Val Gly Glu Glu Leu Ile Asp Arg Trp Gly Ser Asp Ser Asp Asp Cys
        115                 120                 125

Phe Arg Asp Asn Glu Gly Arg Gly Gln Trp Val Lys Gly Lys Glu Leu
130                 135                 140

Val Lys Arg Gln Asn Asn Asn His Phe Ala His Thr Cys Asn Lys
145                 150                 155                 160

Ser Trp Arg Cys Gly Ile Ser Thr Ser Lys Met Tyr Ser Arg Leu Glu
                165                 170                 175

Cys Gln Asp Asp Thr Asp Glu Cys Gln Val Tyr Ile Leu Asp Ala Glu
            180                 185                 190

Gly Asn Pro Ile Asn Val Thr Val Asp Thr Val Leu His Arg Asp Gly
        195                 200                 205

Val Ser Met Ile Leu Lys Gln Lys Ser Thr Phe Thr Thr Arg Gln Ile
    210                 215                 220

Lys Ala Ala Cys Leu Leu Ile Lys Asp Asp Lys Asn Asn Pro Glu Ser
225                 230                 235                 240

Val Thr Arg Glu His Cys Leu Ile Asp Asn Asp Ile Tyr Asp Leu Ser
                245                 250                 255
```

```
Lys Asn Thr Trp Asn Cys Lys Phe Asn Arg Cys Ile Lys Arg Lys Val
            260                 265                 270

Glu His Arg Val Lys Lys Arg Pro Pro Thr Trp Arg His Asn Val Arg
            275                 280                 285

Ala Lys Tyr Thr Glu Gly Asp Thr Ala Thr Lys Gly Asp Leu Met His
            290                 295                 300

Ile Gln Glu Glu Leu Met Tyr Glu Asn Asp Leu Leu Lys Met Asn Ile
305                 310                 315                 320

Glu Leu Met His Ala His Ile Asn Lys Leu Asn Asn Met Leu His Asp
                325                 330                 335

Leu Ile Val Ser Val Ala Lys Val Asp Glu Arg Leu Ile Gly Asn Leu
            340                 345                 350

Met Asn Asn Ser Val Ser Ser Thr Phe Leu Ser Asp Asp Thr Phe Leu
            355                 360                 365

Leu Met Pro Cys Thr Asn Pro Pro Ala His Thr Ser Asn Cys Tyr Asn
            370                 375                 380

Asn Ser Ile Tyr Lys Glu Gly Arg Trp Val Ala Asn Thr Asp Ser Ser
385                 390                 395                 400

Gln Cys Ile Asp Phe Arg Asn Tyr Lys Glu Leu Ala Ile His Asp Val
                405                 410                 415

Glu Phe Trp Ile Pro Thr Ile Gly Asn Thr Thr Tyr His Asp Ser Trp
            420                 425                 430

Lys Asp Ala Ser Gly Trp Ser Phe Ile Ala Gln Gln Lys Ser Asn Leu
            435                 440                 445

Ile Thr Thr Met Glu Asn Thr Lys Phe Gly Gly Val Gly Thr Ser Leu
450                 455                 460

Ser Asp Ile Thr Ser Met Ala Glu Gly Glu Leu Ala Ala Lys Leu Thr
465                 470                 475                 480

Ser Phe Met Phe Gly His Val Val Asn Phe Val Ile Ile Leu Ile Val
                485                 490                 495

Ile Leu Phe Leu Tyr Cys Met Ile Arg Asn Arg Asn Arg Gln Tyr
            500                 505                 510
```

(2) INFORMATION FOR SEQ ID NO:3:

(i) SEQUENCE CHARACTERISTICS:
        (A) LENGTH: 1605 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

```
ACATTTAATA TTGTCTATTA CGGTTTCTAA TCATACAGTA CAAAAATAAA ATCACAATTA    60

ATATAATTAC AAAGTTAACT ACATGACCAA ACATGAACGA AGTCAATTTA GCGGCCAATT   120

CGCCTTCAGC CATGGAAGTG ATGTCGCTCA GACTGGTGCC GACGCCGCCA AACTTGGTGT   180

TCTCCATGGT GGTTATGAGG TTGCTTTTTT GTTGGGCAAT AAACGACCAG CCGCTGGCAT   240

CTTTCCAACT GTCGTGATAG GTCGTGTTGC CGATGGTCGG GATCCAAAAC TCGACGTCGT   300

CGTCAATTGC TAGTTCCTTG TAGTTGCTAA AATCTATGCA TTGCGACGAG TCCGTGTTGG   360

CCACCCAACG CCCTTCTTTG TAGATGCTGT TGTTGTAGCA ATTACTGGTG TGTGCCGGCG   420

GATTGGTGCA CGGCATCAGC AAAAACGTGT CGTCCGACAA AAATGTTGAA GAAACAGAGT   480

TGTTCATGAG ATTGCCAATC AAACGCTCGT CCACCTTGGC CACGGAGACT ATCAGGTCGT   540
```

```
GCAGCATATT GTTTAGCTTG TTGATGTGCG CATGCATCAG CTCAATGTTC ATTTTCAGCA      600

AATCGTTTTC GTACATCAGC TCCTCTTGAA TATGCATCAG GTCGCCTTTG GTGGCAGTGT      660

CTCCCTCTGT GTACTTGGCT CTAACGTTGT GGCGCCAAGT GGGCGGCCGC TTCTTGACTC      720

GGTGCTCGAC TTTGCGTTTA ATGCATCTGT TAAACTTGCA GTTCCACGTG TTTTTAGAAA      780

GATCATATAT ATCATTGTCA ATCAAACAGT GTTCGCGTGT CACCGACTCG GGGTTATTTT      840

TGTCATCTTT AATGAGCAGA CACGCAGCTT TTATTTGGCG CGTGGTGAAC GTAGACTTTT      900

GTTTGAGAAT CATACTCACG CCGTCTCGAT GAAGCACAGT GTCCACGGTC ACGTTGATGG      960

GGTTGCCCTC AGCGTCCAAA ATGTATACCT GGCACTCGTC CGTGTCGTCC TGGCACTCGA     1020

GCCTGCTGTA CATTTTCGAA GTGGAAATGC CGCATCGCCA CGATTTGTTG CACGTGTGGT     1080

GCGCAAAGTG ATTGTTATTC TGCCGCTTCA CCAACTCTTT GCCTTTGACC CACTGGCCGC     1140

GGCCCTCGTT GTCGCGAAAA CAGTCGTCGC TGTCACTGCC CCAACGGTCG ATCAGCTCTT     1200

CGCCCACCTC GCACTGCTGC CTGATGCTCC ACATAAGCAA ATCCTCTTTG CCCACATTCA     1260

GCGTTTTCAT GGTTTCTTCG ACGCGTGTGT TGGGATCCAG CGAGCCGCCG TTGTACGCAT     1320

ACGCCTGGTA GTACCCCTTG TAGCCGATAA TCACGTTTTC GTTGTAGTCC GTCTCCACGA     1380

TGGTGATTTC CACGTCCTTT TGCAGCGTTT CCTTGGGCGG GGTAATGTCC AAGTTTTTAA     1440

TCTTGTACGG ACCCGTCTTC ATTTGCGCGT TGCAGTGCTC CGCCGCAAAG GCAGAATGCG     1500

CCGCCGCCGC CAAAAGCACA TATAAAACAA TAGCGCTTAC CATCTTGCTT GTGTGTTCCT     1560

TATTGAAGCC TTGGTGTGAC TGATTTACTA GTAGCATTGA GGCAT                     1605

(2) INFORMATION FOR SEQ ID NO:4:

(i) SEQUENCE CHARACTERISTICS:
        (A) LENGTH: 530 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

Met Leu Leu Val Asn Gln Ser His Gln Gly Phe Asn Lys Glu His Thr
1               5                   10                  15

Ser Lys Met Val Ser Ala Ile Val Leu Tyr Val Leu Ala Ala
            20                  25                  30

Ala His Ser Ala Phe Ala Ala Glu His Cys Asn Ala Gln Met Lys Thr
            35                  40                  45

Gly Pro Tyr Lys Ile Lys Asn Leu Asp Ile Thr Pro Pro Lys Glu Thr
        50                  55                  60

Leu Gln Lys Asp Val Glu Ile Thr Ile Val Glu Thr Asp Tyr Asn Glu
65                  70                  75                  80

Asn Val Ile Ile Gly Tyr Lys Gly Tyr Tyr Gln Ala Tyr Ala Tyr Asn
                85                  90                  95

Gly Gly Ser Leu Asp Pro Asn Thr Arg Val Glu Glu Thr Met Lys Thr
            100                 105                 110

Leu Asn Val Gly Lys Glu Asp Leu Leu Met Trp Ser Ile Arg Gln Gln
        115                 120                 125

Cys Glu Val Gly Glu Glu Leu Ile Asp Arg Trp Gly Ser Asp Ser Asp
    130                 135                 140

Asp Cys Phe Arg Asp Asn Glu Gly Arg Gly Gln Trp Val Lys Gly Lys
145                 150                 155                 160

Glu Leu Val Lys Arg Gln Asn Asn Asn His Phe Ala His His Thr Cys
```

```
                    165                 170                 175
Asn Lys Ser Trp Arg Cys Gly Ile Ser Thr Ser Lys Met Tyr Ser Arg
            180                 185                 190

Leu Glu Cys Gln Asp Asp Thr Asp Glu Cys Gln Val Tyr Ile Leu Asp
        195                 200                 205

Ala Glu Gly Asn Pro Ile Asn Val Thr Val Asp Thr Val Leu His Arg
        210                 215                 220

Asp Gly Val Ser Met Ile Leu Lys Gln Lys Ser Thr Phe Thr Thr Arg
225                 230                 235                 240

Gln Ile Lys Ala Ala Cys Leu Leu Ile Lys Asp Lys Asn Asn Pro
                245                 250                 255

Glu Ser Val Thr Arg Glu His Cys Leu Ile Asp Asn Asp Ile Tyr Asp
            260                 265                 270

Leu Ser Lys Asn Thr Trp Asn Cys Lys Phe Asn Arg Cys Ile Lys Arg
        275                 280                 285

Lys Val Glu His Arg Val Lys Lys Arg Pro Pro Thr Trp Arg His Asn
        290                 295                 300

Val Arg Ala Lys Tyr Thr Glu Gly Asp Thr Ala Thr Lys Gly Asp Leu
305                 310                 315                 320

Met His Ile Gln Glu Glu Leu Met Tyr Glu Asn Asp Leu Leu Lys Met
                325                 330                 335

Asn Ile Glu Leu Met His Ala His Ile Asn Lys Leu Asn Asn Met Leu
            340                 345                 350

His Asp Leu Ile Val Ser Val Ala Lys Val Asp Glu Arg Leu Ile Gly
                355                 360                 365

Asn Leu Met Asn Asn Ser Val Ser Ser Thr Phe Leu Ser Asp Asp Thr
370                 375                 380

Phe Leu Leu Met Pro Cys Thr Asn Pro Pro Ala His Thr Ser Asn Cys
385                 390                 395                 400

Tyr Asn Asn Ser Ile Tyr Lys Glu Gly Arg Trp Val Ala Asn Thr Asp
                405                 410                 415

Ser Ser Gln Cys Ile Asp Phe Ser Asn Tyr Lys Glu Leu Ala Ile Asp
            420                 425                 430

Asp Asp Val Glu Phe Trp Ile Pro Thr Ile Gly Asn Thr Thr Tyr His
            435                 440                 445

Asp Ser Trp Lys Asp Ala Ser Gly Trp Ser Phe Ile Ala Gln Gln Lys
    450                 455                 460

Ser Asn Leu Ile Thr Thr Met Glu Asn Thr Lys Phe Gly Gly Val Gly
465                 470                 475                 480

Thr Ser Leu Ser Asp Ile Thr Ser Met Ala Glu Gly Glu Leu Ala Ala
            485                 490                 495

Lys Leu Thr Ser Phe Met Phe Gly His Val Val Asn Phe Val Ile Ile
        500                 505                 510

Leu Ile Val Ile Leu Phe Leu Tyr Cys Met Ile Arg Asn Arg Asn Arg
        515                 520                 525

Gln Tyr
530
```

INTERFERON STIMULATING PROTEIN AND USES THEREOF

This application claims the benefit of the filing date of Provisional Application Ser. No. 60/051,053 filed Jun. 27, 1997, which is herein incorporated by reference in its entirety.

FIELD OF THE INVENTION

This invention relates to the baculovirus envelope glycoprotein called the gp64 envelope fusion protein (gp64 EFP), also known as gp64 or gp67 (hereafter "gp67"). The present inventors have suprisingly discovered that this glycoprotein induces both Type I (alpha, beta) and Type II (gamma) interferon (IFN) production, in vivo and in vitro. Accordingly, gp67 is referred to herein as "interferon stimulating protein", or ISP. Thus, the present invention relates to the use of ISP polypeptides, ISP fragments (i.e., portions of ISP), and ISP derivatives, variants and analogs, that demonstrate biological activity (e.g., having anti-viral or anti-cancer activity). The invention additionally relates to polynucleotide sequences encoding ISP polypeptides, ISP fragments (i.e., portions of ISP), and ISP derivatives, variants and analogs, that have biological activity. The ISP polypeptides and polynucleotides of the invention, and fragments, variants, derivatives and analogs thereof, stimulate interferon production. Accordingly, specific embodiments of the invention are directed to the administering a therapeutically effective amount of the ISP polypeptides and polynucleotides, and fragments, variants, derivatives and analogs of the invention, to a patient, (preferably human) to stimulate the production of interferon, such as for anti-viral, anti-parasitic, or anti-cancer therapy, and/or for immunotherapy. The invention also relates to ISP polypeptides, fragments, variants, derivatives and analogs having native gp67-like biological activity (e.g., having anti-viral or anti-cancer activity), stability, immunogenicity, yield, and/or solubility. In specific embodiments, the ISP polypeptides, fragments, variants, derivatives and/or analogs of the invention have enhanced biological activity, increased stability, lower immunogenicity, higher yield, and/or better solubility when compared to native gp67.

BACKGROUND OF THE INVENTION

The Baculoviridae are a family of enveloped animal viruses that are pathogenic to invertebrates, primarily insects. Baculoviruses have large circular double-stranded DNA genomes ranging from approximately 80 to 180 kbp. Baculoviruses are characterized by an infection cycle that produces two virion phenotypes that are structurally and functionally distinct. Blissard, G. W. and Rohrmann, G. F., *Annu. Rev. Entomol.* 35: 127–155 (1990). The first virion phenotype produced in the infection cycle is the budded virus (BV). Production of the BV begins when viral nucleocapsids bud through the plasma membrane into the extracellular space. BV is responsible for the systemic infection of insect cells and tissues in vivo and is highly infectious in cell culture systems. The second virion phenotype, the occlusion-derived virus (ODV), is produced in the very late phase of the infection cycle when nucleocapsids become enveloped within the nucleus. Although BV and ODV appear to be identical in nucleocapsid structure, they differ in the sources of their envelopes. This difference results in differences in biochemical compositions and correlates with observed differences in relative infectivities for different tissues within the insect and in tissue culture. Keddie, B. A. and Volkman, L. E., *J. Gen Virol.* 66:1195–1200 (1985).

Infectivity of BV is dependent on the major BV-specific envelope glycoprotein, gp67. See, e.g., Oomens et al., *Virology* 209:592–603 (1995). This envelope protein is an extensively processed type I integral membrane glycoprotein that has been studied in some detail. See, e.g., Jarvis, D. L. and Garcia, A., *Virology* 205:300–313 (1994); Blissard, G. W. and Wenz, J. R., *J. Virol.* 66:6829–6835 (1992).

The gp67 proteins from three baculoviruses, *Orgyia pseudotsugata* multicapsid nuclear polyhedrosis virus (OpMNPV), *Autographa californica* multicapsid nuclear polyhedrosis virus (AcMNPV), and *Choristoneura fumiferana* multicapsid nuclear polyhedrosis virus (CfMNPV), show a high degree of amino acid sequence similarity (Blissard, G. W. and Rohrmann, G. F., *Virology* 170:537–555 (1989); Hill, J. E. and Faulkner, P., *J. Gen. Virol.* 75:1811–1813 (1994)) with the predicted extracellular domains showing at least 82% identity across all three baculovirus gp67 proteins. The gp67 genes of AcMNPV and OpMNPV have been mapped, cloned, and sequenced (Whitford et al., *J. Virol.* 63:1393–1399 (1989); Blissard, G. W. and Rohrmann, G. F., *Virology* 170:537–555 (1989)).

The important role of gp67 in BV infectivity has been demonstrated by the neutralization of BV infectivity with monoclonal antibodies specific to gp67. See, Hohmann, A. W and Faulkner, P., *Virology* 125:432–444 (1983); Volkman et al., *Virology* 133:354–362 (1984). Later studies demonstrated that gp67 is necessary and sufficient for low pH-activated membrane fusion activity, consistent with the role of gp67 in viral entry through the low pH environment of the endosome. Blissard, G. W. and Wenz, J. R., *J. Virol.* 66:6829–6835 (1992). More recently, Monsma et al., *J. Virol.* 70:4607–4616 (July 1996), used a stably transfected insect cell line that constitutively expressed the gp67 of Orgyia pseudotsugata multicapsid nuclear polyhedrosis virus (OpMNPV), to generate a recombinant gp67-null *Autographa californica* multicapsid nuclear polyhedrosis virus (AcMNPV) baculovirus. They then examined the effect of the gp67-null mutation on viral transmission in both cell culture and insect larvae. Monsma et al., demonstrated that gp67 is an essential virion structural protein that is required for propagation of the budded virus from cell to cell and for systemic infection of the host insect.

Despite the fact that gp67 is a well studied baculovirus envelope glycoprotein with a documented role in cell to cell transmission of infection, the recognition that gp67 induces Type I and Type II interferon production (and thereby confers, inter alia, anti-viral activity) has previously gone unnoticed.

Interferons (IFNs) are a well known family of cytokines secreted by a large variety of eukaryotic cells upon exposure to various mitogens. The interferons have been classified by their chemical and biological characteristics into three groups: IFN-alpha (leukocytes), IFN-beta (fibroblasts), and IFN-gamma (lymphocytes). IFN-alpha and beta are known as Type I interferons; IFN-gamma is known as Type II or immune interferon. The IFNs exhibit anti-viral, immunoregulatory, and antiproliferative activity. The clinical potential of interferons has been recognized, and will be summarized below:

Anti-viral: IFNs have been used clinically for anti-viral therapy, for example, in the treatment of AIDS (Lane, H. C., *Semin. Oncol.* 18:46–52 (October 1991)), viral hepatitis including chronic hepatitis B and hepatitis C (Woo, M. H. and Burnakis, T. G., *Ann. Pharmacother.* 31:330–337 (March 1997); Gibas, A. L., *Gastroenterologist* 1:129–142 (June 1993)), papilloma viruses (Levine, L. A. et al., *Urol-* ogy 47:553–557 (April 1996)), herpes (Ho, M., Annu. Rev. Med. 38:51–59 (1987)), cytomegalovirus (CMV) (Yamamoto, N. et al., Arch. Virol. 94:323–329 (1987)), viral encephalitis (Wintergerst et al., Infection 20:207–212 (July 1992)), and in the prophylaxis of rhinitis (Ho, M., Annu. Rev. Med. 38:51–59 (1987)).

Anti-parasitic: IFNs have been suggested for anti-parasite therapy, for example, IFN-gamma for treating *Cryptosporidium parvum* infection (Rehg, J. E., J. Infect. Des. 174:229–232 (July 1996)).

Anti-bacterial: IFNs have been used clinically for anti-bacterial therapy. For example, IFN-gamma has been used in the treatment of multidrug-resistant pulmonary tuberculosis (Condos et al., Lancet 349:1513–1515 (1997)).

Anti-cancer: Interferon therapy has been used in the treatment of numerous cancers (e.g., hairy cell leukemia (Hofmann et al., Cancer Treat. Rev. 12 (Suppl. B):33–37 (December 1985)), acute myeloid leukemia (Stone. et al., Am. J. Clin. Oncol. 16:159–163 (April 1993)), osteosarcoma (Strander et al., Acta Oncol. 34:877–880 (1995)), basal cell carcinoma (Dogan et al., Cancer Lett. 91:215–219 (May 1995)), glioma (Fetell et al., Cancer 65:78–83 (January 1990)), renal cell carcinoma (Aso et al., Prog. Clin. Biol. Res. 303:653–659 (1989)), multiple myeloma (Peest et al., Br. J. Haematol. 94:425–432 (September 1996)), melanoma (Ikic et al., Int. J. Dermatol. 34:872–874 (December 1995)), and Hodgkin's disease (Rybak et al., J. Biol. Response Mod. 9:1–4 (February 1990)). Synergistic treatment of advanced cancer with a combination of alpha interferon and temozolomide has also been reported (Patent publication WO 9712630 to Dugan, M. H).

Immunotherapy: IFNs have been used clinically for immunotherapy or more particularly, immunosuppression, for example, to prevent graft vs. host rejection, or to curtail the progression of autoimmune diseases, such as arthritis, multiple sclerosis, or diabetes. IFN-beta is approved for sale in the United States for the treatment of multiple sclerosis (i.e., as an immunosuppressant). Recently, it has been reported that patients with multiple sclerosis have diminished production of type I interferons and interleukin-2 (Wandinger et al., J. Neurol. Sci. 149:87–93 (1997)). In addition, immunotherapy with recombinant IFN-alpha (in combination with recombinant human IL-2) has been used successfully in lymphoma patients following autologous bone marrow or blood stem cell transplantation, and may intensify remission following transplantation (Nagler et al., Blood 89:3951–3959 (June 1997)).

Anti-allergy: The administration of IFN-gamma has been used in the treatment of allergies in mammals (See, Patent Publication WO 8701288 to Parkin, J. M. and Pinching, A. J.). It has also recently been demonstrated that there is a reduced production of IL-12 and IL-12-dependent IFN-gamma release in patients with allergic asthma (van der Pouw Kraan et al., J. Immunol. 158:5560–5565 (1997)). Thus, IFN may be useful in the treatment of allergy by inhibiting the humoral response.

Vaccine adjuvantation: Interferons may be used as an adjuvant or co-adjuvant to enhance or stimulate the immune response in cases of prophylactic or therapeutic vaccination (Heath, A. W. and Playfair, J. H. L., Vaccine 10:427–434 (1992)).

Clearly, there exists a need in the art for the discovery of proteins that stimulate endogenous, multi-form interferon production for numerous applications, in e.g., immunotherapy, as well as anti-viral, anti-parasitic, anti-bacterial, or anti-cancer therapies, or any medical condition or situation where an increased production of interferon is desired.

SUMMARY OF THE INVENTION

In accordance with one aspect of the present invention, there are provided isolated nucleic acid molecules, including mRNAs, DNAs, cDNAs, genomic DNA, as well as anti-sense analogs thereof, that encode biologically active and diagnostically or therapeutically useful fragments of ISP.

In accordance with another aspect of the present invention, there are provided novel biologically active and diagnostically or therapeutically useful polypeptide fragments, variants, analogs, and derivatives of ISP.

In accordance with another aspect of the present invention, novel variants of ISP are described. These can be produced by adding, deleting or substituting one or more amino acids of ISP. Natural mutations are called allelic variations. Allelic variations can be silent (no change in the encoded polypeptide) or may have altered amino acid sequence. In order to attempt to improve or alter the characteristics of native ISP, protein engineering may be employed. Recombinant DNA technology known in the art can be used to create novel polypeptides. Muteins and deletion mutations can show, e.g., lower immunogenicity, enhanced activity or increased stability. In addition, they could be purified in higher yield and show better solubility at least under certain purification and storage conditions.

In accordance with another aspect of the present invention, there is provided a process for producing such novel polypeptides by recombinant techniques through the use of recombinant vectors, such as cloning and expression plasmids useful as reagents in the recombinant production of ISP proteins, as well as recombinant prokaryotic and/or eukaryotic host cells comprising an ISP nucleic acid sequence.

In accordance with yet a further aspect of the present invention, there is provided a method for utilizing full-length ISP or ISP portions (i.e., fragments), variants, derivatives, and/or analogs, for therapeutic purposes, for example, to stimulate endogenous production of type I and/or type II interferons. As described above, type I and type II interferons are clinically useful in treating infection (e.g., of viral, parasitic, or bacterial origin), cancer, allergy, and/or for immunotherapy (e.g for imunosuppression of autoimmune diseases, such as, multiple sclerosis) and as an adjuvant in vaccines to enhance or stimulate the immune response. Accordingly, it is believed that the administration of ISP polypeptides, fragments, variants, derivatives, and/or analogs of the invention is clinically useful for the treatment and/or prevention of these disorders as well, or in the treatment of any disorder where an increased production of interferon is desired.

Accordingly, the present invention relates to a method of treating viral infection, bacterial infection, parasitic infection, cancer, autoimmune disorders, and allergy, using ISP polypeptides, fragments, variants, derivatives, and/or analogs of the invention, or polynucleotides there encoding.

In accordance with yet a further aspect of the present invention, there are provided antibodies against such ISP polypeptides, fragments, variants, derivatives, and/or analogs of the invention.

In accordance with another aspect of the present invention, there are provided nucleic acid probes comprising nucleic acid molecules of sufficient length to specifically hybridize to ISP sequences or sequences homologous to ISP.

In accordance with a further aspect of the present invention, there are provided mimetic peptides of ISP, which can be used as therapeutic peptides. Mimetic ISP peptides are short peptides which mimic the biological activity of the ISP protein by binding to and activating the cognate receptors of ISP. Mimetic ISP peptides can also bind to and inhibit the cognate receptors of ISP.

In accordance with yet another aspect of the present invention, there are provided ISP polypeptides and fragments, variants, derivatives, and/or analogs thereof, that may be used in combination with other known cytokines to promote the action of such polypeptides. For example, ISP, or a fragment thereof, can be used by itself or in combination with another cytokine (e.g., IL-12) to treat diseases associated with the underexpression of interferon (e.g., multiple sclerosis).

In accordance with another aspect of the invention, there is provided a method of screening compounds to identify those which antagonize or agonize the action of ISP, as measured by IFN production.

In accordance with another aspect of the present invention, there is provided a process for utilizing such polypeptides, or polynucleotides encoding such polypeptides, to identify cognate ligands (e.g., receptors) for ISP, and also their use for in vitro purposes related to scientific research, synthesis of DNA and manufacture of DNA vectors.

These and other aspects of the present invention should be apparent to those skilled in the art from the teachings herein.

BRIEF DESCRIPTION OF THE DRAWINGS

FIGS. 1A–1D. FIG. 1A shows the complementary strand of the coding sequence (SEQ ID NO:1) and FIG. 1B shows the predicted amino acid sequence (SEQ ID NO:2) of the baculovirus (*Autographica californica*) gp67 disclosed in GenBank Accession: M25420 and NCBI accession Seq ID: 293985. See, also, Whitford et al., J. Virol. 63:1393–1399 (1989). Analysis of the predicted amino acid sequence using the PSORT program (K. Nakai and M. Kanehisa, Genomics 14:897–911 (1992)), predicts a signal peptide consisting of amino acid residues from 1 to about 21, an extracellular domain constituting amino acid residues from about 22 to about 487, a transmembrane domain constituting amino acid residues from about 488 to about 504; and an intracellular domain constituting amino acid residues from about 505 to about 511. FIG. 1C shows the complementary strand of the coding sequence (SEQ ID NO:3) and FIG. 1D shows predicted amino acid sequence (SEQ ID NO:4) of gp67 contained in GenBank accession no. L22858; NID g510708, PID:g559197. Analysis of the predicted amino acid sequence using the PSORT program predicts that amino acid residues from about 39 to about 506 constitute an extracellular domain; from about 22 to about 38 and from about 507 to about 523 consitute transmembrane domains; and from about 524 to about 530 the intracellular domain.

FIG. 6 shows amino-terminal microsequencing of the transblotted material from fraction 1 of the TSK-G2000 column (cf. FIG. 5, supra). Sequencing was terminated after 10 cycles and the sequences analyzed for percent representation and homology to known sequences. The predominant sequence was identical to that of the gp67-envelope glycoprotein from *A. californica*. A second minor sequence was identified which was highly homologous to a known UDP-glucosyl transferase, also from *A. californica*.

FIG. 9C shows that ISP protects mice from lethal challenge with EMCV. The positive controls were murine IFN-gamma (FIG. 9A) and human IFN-alpha A/D (FIG. 9B), both of which are known to be potent anti-viral agents in vitro and in vivo. ISP is shown to protect mice to the same extent as that observed with mIFN-gamma and hIFN-alpha treated mice.

FIG. 10B shows that the anti-viral effect of ISP is long lasting as demonstrated by the ability of mice previously treated with ISP to resist a second lethal challenge with EMCV without the need for additional ISP. Similar results were obtained with mIFN-gamma treated mice (FIG. 10A).

DETAILED DESCRIPTION OF THE PREFERRED EMBODIMENTS

Figure 2:
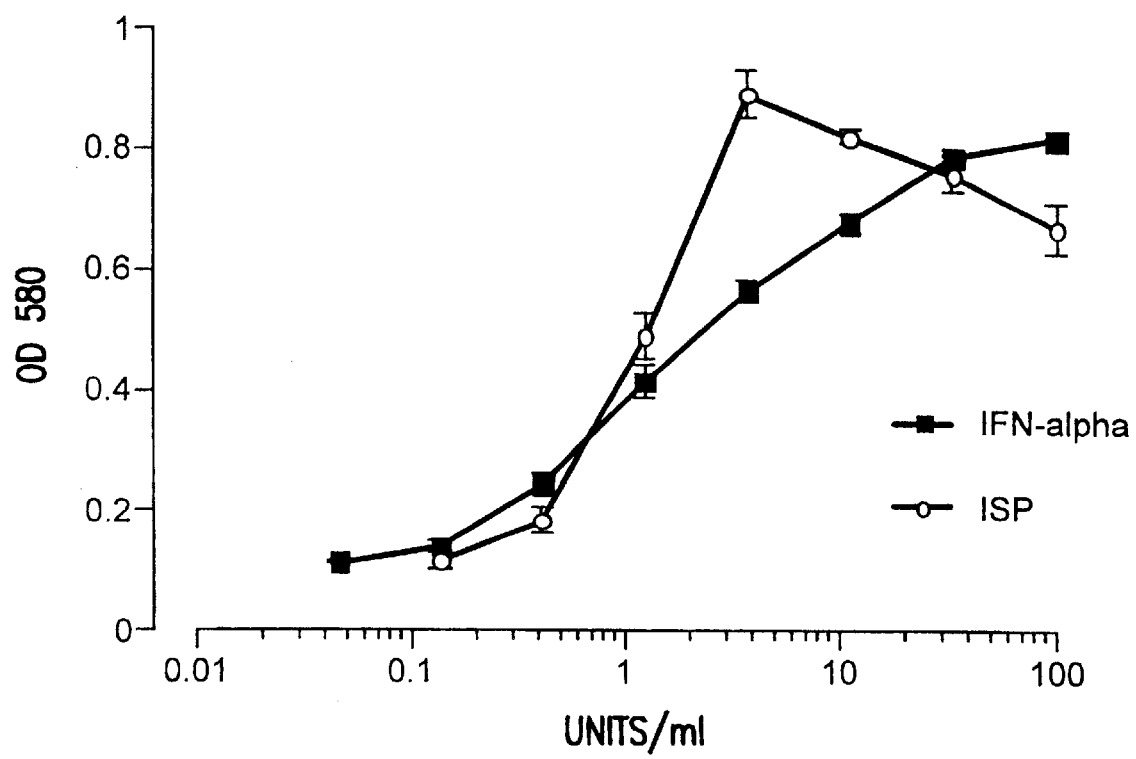
FIG. 2 is a graphic demonstration of the dose dependent anti-viral activity associated with ISP, in vitro. IFN-alpha, a known anti-viral agent, has been included as a positive control.

As discussed above, despite the fact that native gp67 is a well studied baculovirus envelope glycoprotein with a documented role in cell to cell transmission of infection, the recognition that gp67 stimulates interferon production (and thereby exhibits, inter alia, anti-viral activity) has previously gone unappreciated. In fact, the present inventors' discovery of this activity was completely serendipitous.

Briefly, the inventors had been conducting routine protein screening, when it was noticed that supernatants obtained from baculovirus (*Autographica californica* nuclear polyhedrosis virus (AcNPV)) infected Sf9 cells protected normal human dermal fibroblasts from an otherwise lethal infection with either encephalomyocarditis virus (EMCV) or vesicular stomatitis virus (VSV). This activity was initially attributed to the recombinant human protein, osteo-anti-viral protein (OAP), that had been cloned into the virus. However, subsequent purification of OAP and analyses of supernatants obtained from wild-type AcNPV infected cells indicated that the anti-viral activity was not of human origin, but rather, was derived from either the baculovirus or the Sf9 insect cell line in which the protein had been produced. Based on these results, it was decided that the potential therapeutic value of such an anti-viral agent was of sufficient interest to warrant further investigation into the nature of the agent, as well as its mechanism of action.

The inventors first began experimenting with the baculovirus genome. The entire baculovirus genome was screened for anti-viral activity, but this approach failed. However, using classical biochemical purification of this anti-viral agent in addition to independent confirmation by monoclonal antibody technology, it was determined that this anti-viral agent was in fact the baculovirus envelope protein gp67, and that the induction of an anti-viral state was elicited through the induction of multiple forms (alpha, beta, and gamma) of interferon. The ability of gp67 to induce multiple forms of IFN led the inventors to name this protein "Interferon Stimulatory Protein" or ISP. The experiments leading up to the discovery of this new use for gp67 are further described in the Examples below.

Nucleic Acid Molecules

The ISP polynucleotides (including fragments) of the present invention may be in the form of RNA, such as mRNA, or in the form of DNA, including, for instance, cDNA and genomic DNA obtained by cloning or produced synthetically. The DNA may be double-stranded or single-stranded, and if single stranded, may be the coding strand (sense) or non-coding (anti-sense) strand.

In one embodiment, the ISP polypeptides of the invention comprise a polypeptide selected from the group consisting of: (a) a nucleotide sequence encoding the ISP polypeptide having the complete amino acid sequence shown in FIG. 1B (SEQ ID NO:2); (b) a nucleotide sequence encoding the ISP polypeptide having the complete amino acid sequence shown in FIG. 1D (SEQ ID NO:4); (c) a nucleotide sequence encoding the extracellular domain of the ISP amino acid sequence shown in FIG. 1B (amino acid residues 22 to 487 in SEQ ID NO:2); (d) a nucleotide sequence encoding the extracellular domain of the ISP amino acid sequence shown in FIG. 1D (amino acid residues 39 to 506 in SEQ ID NO:4); (e) a nucleotide sequence encoding the ISP extracellular and transmembrane domain depicted in FIG. 1B (SEQ ID NO:2); (f) a nucleotide sequence encoding the ISP extracellular and one or both of the transmembrane domains depicted in FIG. 1D (SEQ ID NO:4), (g) a nucleotide sequence encoding the ISP extracellular and intracellular domains depicted in FIG. 1B, with all or part of the transmembrane domain deleted; (h) a nucleotide sequence encoding the ISP extracellular domain and intracellular domains depicted in FIG. 1D, with all or part of one or both of the transmembrane domains deleted; and (i) a nucleotide sequence complementary to any of the nucleotide sequences in (a), (b), (c), (d), (e), (f), (g), or (h).

The present invention further relates to variants of the hereinabove described polynucleotides which encode for fragments, analogs and derivatives of the ISP polypeptide. The variant of the polynucleotide may be a naturally occurring allelic variant of the polynucleotide or a non-naturally occurring variant of the polynucleotide By an "allelic variant" is intended one of several alternate forms of a gene occupying a given locus on a chromosome of an organism. Genes II, Lewin, B., ed., John Wiley & Sons, New York (1985). Non-naturally occurring variants may be produced using art-known mutagenesis techniques.

Such variants include those produced by substitutions, deletions or additions, which may involve one or more nucleotides. The variants may be altered in coding regions, non-coding regions, or both. Alterations in the coding regions may result in the expression of ISP polypeptides having conservative or non-conservative amino acid substitutions, deletions or additions. Especially preferred among these are silent substitutions, additions and deletions, which do not alter the properties and activities (e.g., anti-viral activity, anti-cancer activity, and inducing interferon production) of the ISP polypeptide or portions thereof. Also especially preferred in this regard are conservative substitutions.

Further embodiments of the invention include isolated nucleic acid molecules comprising, a polynucleotide having a nucleotide sequence at least 90% identical, and more preferably at least 95%, 96%, 97%, 98% or 99% identical to, or alternatively, which is 80–85%, 80–90%, 85–90%, 90–95%, 90–96%, 90–97%, or 90–97% identical to: (a) a nucleotide sequence encoding the ISP polypeptide having the complete amino acid sequence shown in FIG. 1B (SEQ ID NO:2); (b) a nucleotide sequence encoding the ISP polypeptide having the complete amino acid sequence shown in FIG. 1D (SEQ ID NO:4); (c) a nucleotide sequence encoding the extracellular domain of the ISP amino acid sequence shown in FIG. 1B (amino acid residues 22 to 487 in SEQ ID NO:2); (d) a nucleotide sequence encoding the extracellular domain of the ISP amino acid sequence shown in FIG. 1D (amino acid residues 39 to 506 in SEQ ID NO:4); (e) a nucleotide sequence encoding the ISP extracellular and transmembrane domain depicted in FIG. 1B (SEQ ID NO:2); (f) a nucleotide sequence encoding the ISP extracellular domain and one or more of the transmembrane domains depicted in FIG. 1D (SEQ ID NO:4); (g) a nucleotide sequence encoding the ISP extracellular and intracellular domain depicted in FIG. 1B, with all or part of the transmembrane domain deleted; (h) a nucleotide sequence encoding the ISP extracellular and intracellular domains depicted in FIG. 1D, with all or part of one or both of the transmembrane domains deleted; and (i) a nucleotide sequence complementary to any of the nucleotide sequences in (a), (b), (c), (d), (e), (f), (g), or (h).

By a polynucleotide having a nucleotide sequence at least, for example, 95% "identical" to a reference nucleotide sequence encoding a gp67 polypeptide is intended that the nucleotide sequence of the polynucleotide is identical to the reference sequence except that the polynucleotide sequence may include up to five point mutations per each 100 nucleotides of the reference nucleotide sequence encoding the gp67 polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5 or 3 terminal positions of the reference nucleotide sequence or anywhere between those terminal positions, interspersed either individually among nucleotides in the reference sequence or in one or more contiguous groups within the reference sequence. The reference (query) sequence may be the entire gp67 nucleotide sequence shown in FIG. 1A (SEQ ID NO:1) or FIG. 1C (SEQ ID NO:3), the complementary strand thereto, or any polynucleotide or fragment described herein.

As a practical matter, whether any particular nucleic acid molecule is at least 90%, 95%, 96%, 97%, 98% or 99% identical to, or alternatively, which are 80–85%, 80–90%, 85–90%, 90–95%, 90–96%, 90–97%, or 90–97% identical to, for instance, the nucleotide sequence shown in FIG. 1A (SEQ ID NO:1), FIG. 1C (SEQ ID NO:3), or the compelementary strands thereto, can be determined conventionally using known computer programs such as the Bestfit program (Wisconsin Sequence Analysis Package, Version 8 for Unix, Genetics Computer Group, University Research Park, 575 Science Drive, Madison, Wis. 53711. Bestfit uses the local homology algorithm of Smith and Waterman, Advances in Applied Mathematics 2: 482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237–245 (1990)).

Preferred parameters used in a FASTDB alignment of DNA sequences to calculate percent identity are: Matrix= Unitary, k-tuple=4, Mismatch Penalty=1, Joining Penalty= 30, Randomization Group Length=0, Cutoff Score=1, Gap Penalty=5, Gap Size Penalty 0.05, Window Size=500 or the length of the subject nucleotide sequence, whichever is shorter. According to this embodiment, if the subject sequence is shorter than the query sequence because of 5' or 3' deletions, not because of internal deletions, a manual correction is made to the results to take into consideration the fact that the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. A determination of whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of this embodiment. Only bases outside the 5' and 3' bases of the subject sequence, as displayed by the FASTDB alignment, which are not matched/aligned with the query sequence, are calculated for the purposes of manually adjusting the percent identity score. For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/ total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/ aligned with the query sequence are manually corrected for. No other manual corrections are made for the purposes of this embodiment.

Preferred, are nucleic acid molecules having sequences at least 90%, 95%, 96%, 97%, 98% or 99% identical to, or alternatively, which are 80–85%, 80–90%, 85–90%, 90–95%, 90–96%, 90–97%, or 90–97% identical to, the complementary strands of the nucleic acid sequence shown in FIG. 1A (SEQ ID NO:1), FIG. 1C (SEQ ID NO:3), or fragments thereof, which encode a polypeptide having ISP activity. By "a polypeptide having ISP activity" is intended polypeptides exhibiting activity similar, but not necessarily identical, to an activity of the ISP polypeptides of the present invention (either the full-length protein, or the splice variants, or the mature protein), as measured in a particular biological assay. For example, ISP activity can be measured using assays described herein, and/or otherwise known in the art, for determining the ability of a ISP polypeptide, fragment, variant, derivative, or analog of the invention to protect cells from the cytopathic effects of viruses (see, e.g., Examples 1 and 5), to induce IFN-α production by monocytes (see, e.g., Example 3), and to induce IFN-β and IFN-γ production (see, e.g., Example 4).

The present invention includes polynucleotides encoding mimetic peptides of ISP which can be used as therapeutic peptides. Mimetic ISP peptides are short peptides which mimic the biological activity of the ISP protein by binding to and activating the cognate receptors of ISP. Mimetic ISP peptides can also bind to and inhibit the cognate receptors of ISP. Such mimetic peptides are obtained from methods including, but not limited to, phage display or combinatorial chemistry. For example, the method disclosed by Wrighton et al., Science 273:458–463 (1996) to generate mimetic ISP peptides.

The polynucleotides of the present invention may also have the coding sequence fused in frame to a marker sequence which allows for purification of the polypeptide of the present invention. The marker sequence may be a commercially available hexahistidine tag (e.g., that supplied by a pQE-9 vector (Qiagen, Inc.)) to provide for purification of the mature polypeptide fused to the marker in the case of a bacterial host, or, for example, the marker sequence may be a hemagglutinin (HA) tag when a mammalian host (e.g., COS-7 cells) is used. The HA tag corresponds to an epitope derived from the influenza hemagglutinin protein (Wilson et al. Cell 37:767 (1984)).

The term "gene" means the segment of DNA involved in producing a polypeptide chain; it includes regions preceding and following the coding region (leader and trailer) as well as intervening sequences (introns) between individual coding segments (exons).

Using the information provided herein, such as the nucleotide sequences disclosed in FIG. 1B, FIG. 1D, or the complelmentary strand thereto, nucleic acid molecules of the present invention encoding ISP polypeptides may be obtained using standard cloning and screening procedures, such as PCR of viral DNA and/or techniques used for cloning cDNAs using mRNA as starting material. For example, fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene, including regulatory and promotor regions, exons, and introns. An example of a screen comprises: isolating the coding region of the gene by using the known DNA sequence to synthesize a labeled oligonucleotide probe having a sequence complementary to that of the DNA sequence of the present invention, and screening a cDNA or genomic library to determine which members of the library hybridize to the probe.

The present invention is further directed to fragments of the isolated nucleic acid molecules described herin. By a fragment of an isolated nucleic acid molecule having the nucleotide sequence shown in FIG. 1A (SEQ ID NO:1), FIG. 1C (SEQ ID NO:3), or the complementary strands thereto, is intended fragments at least about 15 nt, and more preferably at least about 20 nt, still more preferably at least about 30 nt, and even more preferably, at least about 40, 50, 100, 150, 200, 250, 300, 400, or 500 nt in length. These fragments have numerous uses which include, but are not limited to, diagnostic probes and primers as discussed herein. Of course, larger fragments, such as those of 500–1500 nt in length are also useful according to the present invention, as are fragments corresponding to most, if not all, of the nucleotide sequences shown in FIG. 1A (SEQ ID NO:1) or FIG. 1C (SEQ ID NO:3), or the complementary strands thereto. By a fragment at least 20 nt in length, for example, is intended fragments which include 20 or more contiguous bases from the nucleotide sequence as shown in FIG. 1A (SEQ ID NO:1), FIG. 1C (SEQ ID NO:3), or the complementary strands thereto.

Representative examples of ISP polynucleotide fragments of the invention include, for example, fragments that comprise, or alternatively, consist of a sequence from about nucleotide 1–50, 51–100, 101–150, 151–200, 201–250, 251–300, 301–350, 351–400, 401–450, 451–500, 501–550, 551–600, 651–700, 701– 750, 751–800, 800–850, 851–900, 901–950, 951–1000, 1001–1050, 1051–1100, 1101–1150, 1151–1200, 1201–1250, 1251–1300, 1301–1350, 1351–1400, 1401–1450, 1451–1500, 1501–1560, or 1560–1605 of SEQ ID NO:1, or SEQ ID NO:3, or the complementary strand thereto. In this context "about" includes the particularly recited ranges, larger or smaller by several (5, 4, 3, 2, or 1) nucleotides, at either terminus or at both termini. Preferably, these fragments encode a polypeptide having ISP activity (e.g., anti-viral activity, anti-cancer activity, and/or induction of the production of interferon).

Preferred nucleic acid fragments of the present invention include nucleic acid molecules encoding one or more ISP domains. In particular embodiments, such nucleic acid fragments include nucleic acid molecules encoding: a polypeptide comprising, or alternatively, consisting of, the extracellular domain of the polypeptide disclosed in FIG. 1B (predicted to constitute amino acid residues from about 22 to about 487 in SEQ ID NO:2); a polypeptide comprising, or alternatively, consisting of, the extracellular domain of the polypeptide disclosed in FIG. 1D (predicted to constitute amino acid residues from about 39 to about 506 in SEQ ID NO:4); a polypeptide comprising, or alternatively, consisting of the ISP extracellular domain and transmembrane domain of the polypeptide disclosed in FIG. 1B (predicted to constitute amino acid residues 22 to 504 in SEQ ID NO:2); a polypeptide comprising, or alternatively, consisting of the ISP extracellular domain and one or both of the transmembrane domains of the polypeptide disclosed in FIG. 1D (predicted to constitute amino acid residues 22 to 523 in SEQ ID NO:2); or a polypeptide comprising, or alternatively, consisiting of extracellular and intracellular domains of the ISP polypeptide of FIG. 1B or FIG. 1D, with all or part of one or both of the transmembrane domain(s) deleted.

The amino acid residues constituting the signal peptide, extracellular, transmembrane and intracellular domains have been predicted by computer analysis. Thus, as one of ordinary skill would appreciate, the amino acid residues constituting these domains may vary slightly (e.g., by about 1 to about 15 amino acid residues) depending on the criteria used to define each domain.

In another aspect, the invention provides isolated nucleic acid molecules comprising polynucleotides which hybridize, preferably under stringent hybridization conditions, to a portion or the entirety of the polynucleotides of one of the nucleic acid molecules of the invention described herein (including polynucleotide fragments as described herein). By "stringent hybridization conditions" is intended overnight incubation at 42° C. in a solution comprising: 50% formamide, 5×SSC (150 mM NaCl, 15 mM trisodium citrate), 50 mM sodium phosphate (pH 7.6). 5×Denhardt's solution, 10% dextran sulfate, and 20 µg/ml denatured, sheared salmon sperm DNA, followed by washing the filters in 0.1×SSC at about 65° C. In specific embodiments, these nucleic acid molecules do not hybridize to polynucleotides encoding the transmembrane domain, and/or intracellular domain of the ISP disclosed in FIGS. 1A–1D.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70, or 80–150 nt, or the entire length of the reference polynucleotide. These are useful as diagnostic probes and primers as discussed above and in more detail below.

Further embodiments of the invention are directed to ISP polynucleotides encoding the gp67 proteins of: *Orgyia pseudotsugata* multicapsid nuclear polyhedrosis virus (OpMNPV; as disclosed in Blissard et al., J. Virol. 170:537–555 (1989); genbank accession no. M22446, NID g332525), *Choristoneura fumiferana* multicapsid nuclear polyhedrosis virus (CtMNPV; as disclosed in Hill et al., 1994, J. Gen. Virol. 75:1811–1813; genbank accession no. L12412; NID g793913), and *Anagrapha falcifera* virus (as disclosed in genbank accession no. U64897; NID g2062364), the polynucleotide and polypeptide sequence of each of which is herein incorporated by reference in its entirety. Additional embodiments are directed to fragments (i.e., portions, preferably of the extracellular domain), variants, derivatives, and analogs of these polynucleotides which, preferably have ISP activity (e.g,. induction of interferon production, anti-viral activity, or anti-cancer activity).

Vectors and Host Cells

The present invention also relates to vectors which include the isolated DNA molecules of the present invention, host cells which are genetically engineered with the recombinant vectors, and the production of ISP polypeptides or fragments thereof by recombinant techniques or alternatively, via chemical synthetic techniques known in the art.

Polypeptide fragments of the present invention may be employed for producing the corresponding full-length polypeptide by peptide synthesis; therefore, the fragments may be employed as intermediates for producing the full-length polypeptides. The present invention also relates to vectors which include polynucleotides of the present invention, host cells which are genetically engineered with vectors of the invention and the production of polypeptides of the invention by recombinant techniques.

Host cells are genetically engineered (transduced, transformed, or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the ISP genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively associated with an appropriate expression control sequence (s) (e.g., promoter and/or enhancer) to direct cDNA synthesis. As representative examples of such promoters, there may be mentioned: LTR or SV40 promoter, the E. coli. lac or trp, the phage lambda PL promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli. The vector containing the appropriate DNA sequence as hereinabove described, as well as an appropriate promoter or control sequence, may be employed to transform an appropriate host to permit the host to express the protein.

Selection of appropriate vectors and promoters for expression in a host cell is a well known procedure and the requisite techniques for expression vector construction, introduction of the vector into the host and expression in the host are routine skills in the art.

As representative examples of appropriate hosts, there may be mentioned: bacterial cells, such as E. coli, Streptomyces, Salmonella typhimurium; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably associated with the sequence. Large numbers of suitable vectors and promoters are known to those of skill in the art, and are commercially available. The following vectors are provided by way of example; Bacterial: pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223–3, pKK233–3, pDR540, pRIT5 (Pharmacia); Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232–8 and pCM7. Particular named bacterial promoters include lacI, lacZ, T3, T7, gpt, lambda PR, PL and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

The present invention also relates to host cells containing the vector constructs discussed herein, and additionally encompasses host cells containing nucleotide sequences of the invention that are operably associated with one or more heterologous control regions (e.g., promoter and/or enhancer) using techniques known of in the art. The host cell can be a higher eukaryotic cell, such as an insect cell (e.g., sf9 cell line), or a mammalian cell (e.g., a human derived cell), or a lower eukaryotic cell, such as a yeast cell, or the host cell can be a prokaryotic cell, such as a bacterial cell. The host strain may be chosen which modulates the expression of the inserted gene sequences, or modifies and processes the gene product in the specific fashion desired. Expression from certain promoters can be elevated in the presence of certain inducers, thus expression of the genetically engineered polypeptide may be controlled. Furthermore, different host cells have characteristics and specific mechanisms for the translational and post-translational processing and modification (e.g., glycosylation, phosphorylation, or cleavage) of proteins. Appropriate cell lines can be chosen to ensure the desired modifications and processing of the foreign protein expressed. Introduction of the construct into the host cell can be effected by calcium phosphate transfection, DEAE-Dextran mediated transfection, or electroporation (Davis, L. et al., Basic Methods in Molecular Biology (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., Molecular Cloning: A Laboratory Manual, Second Edition, Cold Spring Harbor, N.Y. (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The ISP polypeptide or polypeptide fragments of the invention may be expressed in a modified form, such as a fusion protein (comprising the polypeptide joined via a peptide bond to a heterologous protein sequence (of a different protein)), and may include not only secretion signals, but also additional heterologous functional regions. Such a fusion protein can be made by ligating polynucleotides of the invention and the desired nucleic acid sequence encoding, the desired amino acid sequence to each other, by methods known in the art, in the proper reading frame, and expressing the fusion protein product by methods known in the art. Alternatively, such a fusion protein can be made by protein synthetic techniques, e.g., by use of a peptide synthesizer. Thus, a region of additional amino acids, particularly charged amino acids, may be added to the N-terminus of the polypeptide to improve stability and persistence in the host cell, during purification, or during subsequent handling, and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art.

A preferred fusion protein comprises a heterologous region from immunoglobulin that is useful to solubilize receptors. For example, EP-A-O 464 533 (Canadian counterpart 2045869) discloses fusion proteins comprising various portions of constant region of immunoglobin molecules together with another human protein or part thereof. In many cases, the Fc part of a fusion protein is advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when the Fc portion proves to be a hindrance to use in therapy and diagnosis, for example when the fusion protein is to be used as antigen for immunizations. In drug discovery, for example, human proteins, such as, shIL5- has been fused with Fc portions for the purpose of high-throughput screening assays to identify antagonists of hIL-5. See, Bennett et al., J. Molec. Recog. 8:52–58 (1995) and Johanson et al., J. Blot. Chem. 270:9459–9471 (1995).

Generally, recombinant expression vectors will include origins of replication and selectable markers permitting transformation of the host cell, e.g., the ampicillin resistance gene of E. coli and S. cerevisitie TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillits subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEMI (Promega Biotec, Madison, Wis., USA) These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, Cell 23:175 (1981), and other cell lines capable of expressing a compatible vector, for example, the C127, 3T3, CHO, HeLa, and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The ISP polypeptide can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeotides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

ISP Polypeptides and Fragments

The present invention further relates to ISP fragments, variants, derivatives, and analogs of the ISP polypeptide, in particular those, with ISP activity (e.g., induce interferon production, anti-viral activity, and anti-cancer). In specific embodiments, these polypeptides have increased biological activity compared to native gp67.

The terms "fragment," "derivative" and "analog" when referring to the ISP polypeptide, means a polypeptide which retains essentially the same biological function or activity as such polypeptide. Thus, an analog includes a proprotein which can be activated by cleavage of the proprotein portion to produce an active mature polypeptide.

The polypeptides of the present invention may be recombinant polypeptides, natural polypeptides or synthetic polypeptides, preferably recombinant polypeptides.

The polypeptides of this invention may be membrane bound or may be in a soluble circulating form. Soluble peptides are defined by amino acid sequence wherein the sequence comprises the polypeptide sequence lacking the transmembrane domain.

The polypeptides of the present invention may exist as a membrane bound polypeptide having a transmembrane region and an intra- and extracellular region or they may exist in soluble form wherein the transmembrane domain is lacking.

The fragment, derivative or analog of the ISP polypeptide of FIG. 1B, FIG. 1D or another polypeptide described herein, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide, or a leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the ISP polypeptides. The prevention of aggregation is highly desirable. Aggregation of proteins not only results in a loss of activity but can also be problematic when preparing pharmaceutical formulations, because they can be immunogenic. (Pinckard et al., Clin Exp. Immunol. 2:331–340 (1967); Robbins et al., Diabetes 36:838–845 (1987); Cleland et al., Crit. Rev. Therapeutic Drug Carrier Systems 10:307–377 (1993)).

The terms "peptide" and "oligopeptide" are considered synonymous (as is commonly recognized) and each term can be used interchangeably as the context requires to indicate a chain of at least two amino acids coupled by peptidyl linkages. The word "polypeptide" is used herein for chains containing more than ten amino acid residues. All oligopeptide and polypeptide formulas or sequences herein are written from left to right and in the direction from amino terminus to carboxy terminus.

It will be recognized in the art that some amino acid sequences of the ISP polypeptide (e.g., polypeptides corresponding to the extracellular domain of the polypeptide depicted in FIG. 1B or FIG. 1D) can be varied without significant effect of the structure or function of the protein. If such differences in sequence are contemplated, it should be remembered that there will be critical areas on the protein which determine activity. In general, it is possible to replace residues which form the tertiary structure, provided that residues performing a similar function are used. In other instances, the type of residue may be completely unimportant if the alteration occurs at a non-critical region of the protein.

Thus, the invention further includes variations of the ISP polypeptide that have ISP polypeptide activity or which include regions of ISP protein such as the polypeptide portions (i.e., fragments) discussed below. Such mutants include deletions, insertions, inversions, repeats, and type substitutions (for example, substituting one hydrophilic residue for another, but not strongly hydrophilic for strongly hydrophobic as a rule). Small changes or such "neutral" amino acid substitutions will generally have little effect on activity.

Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

As indicated in detail above, further guidance concerning which amino acid changes are likely to be phenotypically silent (i.e., are not likely to have a significant deleterious effect on a function) can be found in Bowie et al., "Deciphering the Message in Protein Sequences: Tolerance to Amino Acid Substitutions," Science 247:1306–1310 (1990).

The present invention includes mimetic peptides of ISP which can be used as therapeutic peptides. Mimetic ISP peptides are short peptides which mimic the biological activity of the ISP protein by binding to and activating the cognate receptors of ISP. Mimetic ISP peptides can also bind to and inhibit the cognate receptors of ISP. Such mimetic peptides are obtained from methods including, but not limited to, phage display or combinatorial chemistry. For example, the method disclosed by Wrighton et al., Science 273:458–463 (1996) can be used to generate mimetic ISP peptides.

The polypeptides and polynucleotides of the present invention are preferably provided in an isolated form. By "isolated polypeptide" is intended a polypeptide that is removed from its native environment. For example, a naturally occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention also include polypeptides which are at least 80% identical, more preferably at least 90%, 95%, 96%, 97%, 98% or 99% identical to, or alternatively, which are 80–85%, 80–90%, 85–90%, 90–95%, 90–96%, 90–97%, or 90–97% identical to, the ISP polypeptide sequence shown in FIG. 1B (SEQ ID NO:2), FIG. 1D (SEQ ID NO:4), or other polypeptides described herein, or fragments thereof, and include portions of such polypeptides with at least 30 amino acids and more preferably at least 50 amino acids.

By a polypeptide having an amino acid sequence at least, for example, 95% "identical" to a reference amino acid sequence of a ISP polypeptide is intended that the amino acid sequence of the polypeptide is identical to the reference sequence except that the polypeptide sequence may include up to five amino acid alterations per each 100 amino acids of the reference amino acid of an ISP polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence anywhere between those terminal positions, interspersed either individually among amino acid residues in the reference sequence or in one or more contiguous groups within the reference sequence. The reference (query) sequence may be the entire ISP polypeptide sequence shown in FIG. 1B (SEQ ID NO:2) or FIG. 1D (SEQ ID NO:4), or any polypeptide or fragment described herein.

As a practical matter, whether any particular nucleic acid molecule is at least 90%, 95%, 96%, 97%, 98% or 99% identical to, or alternatively, which is 80–85%, 80–90%, 85–90%, 90–95%, 90–96%, 90–97%, or 90–97% identical to, for instance, the amino acid sequence shown in FIG. 1B (SEQ ID NO:2), the amino acid sequence shown in FIG. 1D (SEQ ID NO:4), or fragments thereof (e.g., such as those consisting of the extracellular domain of the ISP polypeptide), can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237–245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty= 0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C- termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

For many proteins, including the extracellular domain of a membrane associated protein or the mature form(s) of a secreted protein, it is known in the art that one or more amino acids may be deleted from the N-terminus or C-terminus without substantial loss of biological function.

In one embodiment, the present invention further provides polypeptides having one or more residues deleted from the amino terminus of the amino acid sequence of the ISP polypeptide depicted in FIG. 1B (SEQ ID NO:2) or FIG. 1D (SEQ ID NO:4). Particularly, in one embodiment, N-terminal deletions of the ISP polypeptide can be described by the general formula m to 511, where m is an integer from 2 to 509 corresponding to the position of amino acid residue identified in SEQ ID NO:2 and preferably, corresponds to one of the N-terminal amino acid residues identified in the N-terminal deletions specified herein. In specific embodiments, N-terminal deletions of the ISP polypeptide of the invention comprise, or preferably consist of, amino acid residues: V-2 to Y-511; S-3 to Y-511; A-4 to Y-511; I-5 to Y-511; V-6 to Y-511; L-7 to Y-511; Y-8 to Y-511; V-9 to Y-511; L-10 to Y-511; L-11 to Y-511; A-12 to Y-511; A-13 to Y-511; A-14 to Y-511; A-15 to Y-511; H-16 to Y-511; S-17 to Y-511; A-18 to Y-511; F-19 to Y-511; A-20 to Y-511; A-21 to Y-511; E-22 to Y-511; H-23 to Y-511; C-24 to Y-511; N-25 to Y-511; A-26 to Y-511; Q-27 to Y-511; M-28 to Y-511; K-29 to Y-511; T-30 to Y-511; G-31 to Y-511; P-32 to Y-511; Y-33 to Y-511; K-34 to Y-511; I-35 to Y-511; K-36 to Y-511; N-37 to Y-511; L-38 to Y-511; D-39 to Y-511; I-40 to Y-511; T-41 to Y-511; P-42 to Y-511; P-43 to Y-511; K-44 to Y-511; E-45 to Y-511; T-46 to Y-511; L-47 to Y-511; Q-48 to Y-511; K-49 to Y-511; D-50 to Y-511 V-51 to Y-511; E-52 to Y-511; I-53 to Y-511; T-54 to Y-511; I-55 to Y-511; V-56 to Y-511; E-57 to Y-511; T-58 to Y-511; D-59 to Y-511; Y-60 to Y-511; N-61 to Y-511; E-62 to Y-511; N-63 to Y-511; V-64 to Y-511; I-65 to Y-511; I-66 to Y-511; G-67 to Y-511; Y-68 to Y-511; K-69 to Y-511; G-70 to Y-511; Y-71 to Y-511; Y-72 to Y-511; Q-73 to Y-511; A-74 to Y-511; Y-75 to Y-511; A-76 to Y-511; Y-77 to Y-511; N-78 to Y-511; G-79 to Y-511; G-80 to Y-511; S-81 to Y-511; L-82 to Y-511; D-83 to Y-511; P-84 to Y-511; N-85 to Y-511, T-86 to Y-511; R-87 to Y-511; V-88 to Y-511; E-89 to Y-511; E-90 to Y-511; T-91 to Y-511; M-92 to Y-511; K-93 to Y-511; T-94 to Y-511; L-95 to Y-511; N-96 to Y-511; V-97 to Y-511; G-98 to Y-511; K-99 to Y-511; E-100 to Y-511; D-101 to Y-511; L-102 to Y-511; L-103 to Y-511; M-104 to Y-511; W-105 to Y-511; S-106 to Y-511; I-107 to Y-511; R-108 to Y-511; Q-109 to Y-511; Q-110 to Y-511; C-111 to Y-511; E-112 to Y-511; V-113 to Y-511; G-114 to Y-511; E-115 to Y-511; E-116 to Y-511; L-117 to Y-511; I-118 to Y-511; D-119 to Y-511; R-120 to Y-511; W-121 to Y-511; G-122 to Y-511; S-123 to Y-511; D-124 to Y-511; S-125 to Y-511; D-126 to Y-511; D-127 to Y-511; C-128 to Y-511; F-129 to Y-511; R-130 to Y-511; D-131 to Y-511; N-132 to Y-511; E-133 to Y-511; G-134 to Y-511; R-135 to Y-511; G-136 to Y-511; Q-137 to Y-511; W-138 to Y-511; V-139 to Y-511; K-140 to Y-511; G-141 to Y-511; K-142 to Y-511; E-143 to Y-511; L-144 to Y-511; V-145 to Y-511; K-146 to Y-511; R-147 to Y-511; Q-148 to Y-511; N-149 to Y-511; N-150 to Y-511; N-151 to Y-511; H-152 to Y-511; F-153 to Y-511; A-154 to Y-511; H-155 to Y-511; H-156 to Y-511; T-157 to Y-511; C-158 to Y-511; N-159 to Y-511; K-160 to Y-511; S-161 to Y-511; W-162 to Y-511; R-163 to Y-511; C-164 to Y-511; G-165 to Y-511; I-166 to Y-511; S-167 to Y-511; T-168 to Y-511; S-169 to Y-511; K-170 to Y-511; M-171 to Y-511; Y-172 to Y-511; S-173 to Y-511; R-174 to Y-511; L-175 to Y-511; E-176 to Y-511; C-177 to Y-511; Q-178 to Y-511; D-179 to Y-511; D-180 to Y-511; T-181 to Y-511; D-182 to Y-511; E-183 to Y-511; C-184 to Y-511; Q-185 to Y-511; V-186 to Y-511; Y-187 to Y-511; I-188 to Y-511; L-189 to Y-511; D-190 to Y-511; A-l91 to Y-511; E-192 to Y-511; G-193 to Y-511; N-194 to Y-511; P-195 to Y-511; I-196 to Y-511; N-197 to Y-511; V-198 to Y-511; T-199 to Y-511; V-200 to Y-511; D-201 to Y-511; T-202 to Y-511; V-203 to Y-511; L-204 to Y-511; H-205 to Y-511; R-206 to Y-511; D-207 to Y-511; G-208 to Y-511; V-209 to Y-511; S-210 to Y-511; M-211 to Y-511; I-212 to Y-511; L-213 to Y-511; K-214 to Y-51; Q-215 to Y-511; K-216 to Y-511; S-217 to Y-511; T-218 to Y-511; F-219 to Y-511; T-220 to Y-511; T-221 to Y-511; R-222 to Y-511; Q-223 to Y-511; I-224 to Y-511; K-225 to Y-511; A-226 to Y-511; A-227 to Y-511; C-228 to Y-511; L-229 to Y-511; L-230 to Y-511; I-231 to Y-511; K-232 to Y-511; D-233 to Y-511; D-234 to Y-511; K-235 to Y-511; N-236 to Y-511; N-237 to Y-511; P-238 to Y-511; E-239 to Y-511; S-240 to Y-511; V-241 to Y-511; T-242 to Y-511; R-243 to Y-511; E-244 to Y-511; H-245 to Y-511; C-246 to Y-511; L-247 to Y-511; I-248 to Y-511; D-249 to Y-511; N-250 to Y-511; D-251 to Y-511; I-252 to Y-511; Y-253 to Y-511; D-254 to Y-511; L-255 to Y-511; S-256 to Y-511; K-257 to Y-511; N-258 to Y-511; T-259 to Y-511; W-260 to Y-511; N-261 to Y-511; C-262 to Y-511; K-263 to Y-511; F-264 to Y-511; N-265 to Y-511; R-266 to Y-511; C-267 to Y-511; I-268 to Y-511; K-269 to Y-511; R-270 to Y-511; K-271 to Y-511; V-271 to Y-511; E-273 to Y-511; H-274 to Y-511; R-275 to Y-511; V-276 to Y-511; K-277 to Y-511; K-278 to Y-511; R-279 to Y-511; P-280 to Y-511; P-281 to Y-511; T-282 to Y-511; W-283 to Y-511; R-284 to Y-511; H-285 to Y-511; N-286 to Y-511; V-287 to Y-511; R-288 to Y-511; A-289 to Y-511; K-290 to Y-511; Y-291 to Y-511; T-292 to Y-511; E-293 to Y-511; G-294 to Y-511; D-295 to Y-511; T-296 to Y-511; A-297 to Y-511; T-298 to Y-511; K-299 to Y-511; G-300 to Y-511; D-301 to Y-511; L-302 to Y-511; M-303 to Y-511; H-304 to Y-511; I-305 to Y-511; Q-306 to Y-511; E-307 to Y-511; E-308 to Y-511; L-309 to Y-511; M-310 to Y-511; Y-311 to Y-511; E-312 to Y-511; N-313 to Y-511; D-314 to Y-511; L-315 to Y-511; L-316 to Y-511; K-317 to Y-511; M-318 to Y-511; N-319 to Y-511; I-320 to Y-511; E-321 to Y-511; L-322 to Y-511; M-323 to Y-511; H-324 to Y-511; A-325 to Y-511; H-326 to Y-511; I-327 to Y-511; N-328 to Y-511; K-329 to Y-511; L-330 to Y-511; N-331 to Y-511; N-332 to Y-511; M-333 to Y-511; L-334 to Y-511; H-335 to Y-511; D-336 to Y-511; L-337 to Y-511; I-338 to Y-511; V-339 to Y-511; S-340 to Y-511; V-341 to Y-511; A-342 to Y-511; K-343 to Y-511; V-344 to Y-511; D-345 to Y-511; E-346 to Y-511; R-347 to Y-511; L-348 to Y-511; I-349 to Y-511; G-350 to Y-511; N-351 to Y-511; L-352 to Y-511; M-353 to Y-511; N-354 to Y-511; N-355 to Y-511; S-356 to Y-511; V-357 to Y-511; S-358 to Y-511; S-359 to Y-511; T-360 to Y-511; F-361 to Y-511; L-362 to Y-511; S-363 to Y-511; D-364 to Y-511; D-365 to Y-511; T-366 to Y-511; F-367 to Y-511; L-368 to Y-511; L-369 to Y-511; M-370 to Y-511; P-371 to Y-511; C-372 to Y-511; T-373 to Y-511; N-374 to Y-511; P-375 to Y-511; P-376 to Y-511; A-377 to Y-511; H-378 to Y-511; T-379 to Y-511; S-380 to Y-511; N-381 to Y-511; C-382 to Y-511; Y-383 to Y-511; N-384 to Y-511; N-385 to Y-511; S-386 to Y-511; I-387 to Y-511; Y-388 to Y-511; K-389 to Y-511; E-390 to Y-511; G-391 to Y-511; R-392 to Y-511; W-393 to Y-511; V-394 to Y-511; A-395 to Y-511; N-396 to Y-511; T-397 to Y-511; D-398 to Y-511; S-399 to Y-511; S-400 to Y-511; Q-401 to Y-511; C-402 to Y-511; I-403 to Y-511; D-404 to Y-511; F-405 to Y-511; R-406 to Y-511; N-407 to Y-511; Y-408 to Y-511; K-409 to Y-511; E-410 to Y-511; L-411 to Y-511; A-412 to Y-511; I-413 to Y-511; H-414 to Y-511; D-415 to Y-511; V-416 to Y-511; E-417 to Y-511; F-418 to Y-511; W-419 to Y-511; I-420 to Y-511; P-421 to Y-511; T-422 to Y-511; I-423 to Y-511; G-424 to Y-511; N-425 to Y-511; T-426 to Y-511; T-427 to Y-511; Y-428 to Y-511; H-429 to Y-511; D-430 to Y-511; S-431 to Y-511; W-432 to Y-511; K-433 to Y-511; D-434 to Y-511; A-435 to Y-511;

S-436 to Y-511; G-437 to Y-511; W-438 to Y-511; S-439 to Y-511; F-440 to Y-511; I-441 to Y-511; A-442 to Y-511; Q-443 to Y-511; Q-444 to Y-511; K-445 to Y-511; S-446 to Y-511; N-447 to Y-511; L-448 to Y-511; I-449 to Y-511; T-450 to Y-511; T-451 to Y-511; M-452 to Y-511; E-453 to Y-511; N-454 to Y-511; T-455 to Y-511; K-456 to Y-511; F-457 to Y-511; G-458 to Y-511; G-459 to Y-511; V-460 to Y-511; G-461 to Y-511; T-462 to Y-511; S-463 to Y-511; L-464 to Y-511; S-465 to Y-511; D-466 to Y-511; I-467 to Y-511; T-468 to Y-511; S-469 to Y-511; M-470 to Y-511; A-471 to Y-511; E-472 to Y-511; G-473 to Y-511; E-474 to Y-511; L-475 to Y-511; A-476 to Y-511; A-477 to Y-511; K-478 to Y-511; L-479 to Y-511; T-480 to Y-511; S-481 to Y-511; F-482 to Y-511; M-483 to Y-511; F-484 to Y-511; G-485 to Y-511; H-486 to Y-511; V-487 to Y-511; V-488 to Y-511; N-489 to Y-511; F-490 to Y-511; V-491 to Y-511; I-492 to Y-511; I-493 to Y-511; L-494 to Y-511; I-495 to Y-51i; V-496 to Y-511; I-497 to Y-511; L-498 to Y-511; F-499 to Y-511; L-500 to Y-511; Y-501 to Y-511; C-502 to Y-511; M-503 to Y-511; I-504 to Y-511; R-505 to Y-511; N-506 to Y-511; of SEQ ID NO:2. Polynucleotides encoding these polypeptides are also encompassed by the invention.

In another embodiment, N-terminal deletions of the ISP polypeptide can be described by the general formula m to 477 where m is an integer from 1 to 475 corresponding to the amino acid residue identified in SEQ ID NO:2. In specific embodiments, N terminal deletions of the ISP polypeptide of the invention comprise, or preferably, consist of, amino acids residues V-2 to A-477; S-3 to A-477; A-4 to A-477; I-5 to A-477; V-6 to A-477; L-7 to A-477; Y-8 to A-477; V-9 to A-477; L-10 to A-477; L-11 to A-477; A-12 to A-477; A-13 to A-477; A-14 to A-477; A-15 to A-477; H-16 to A-477; S-17 to A-477; A-18 to A-477; F-19 to A-477; A-20 to A-477; A-21 to A-477; E-22 to A-477; H-23 to A-477; C-24 to A-477; N-25 to A-477; A-26 to A-477; Q-27 to A-477; M-28 to A-477; K-29 to A-477; T-30 to A-477; G-31 to A-477; P-32 to A-477; Y-33 to A-477; K-34 to A-477; I-35 to A-477; K-36 to A-477; N-37 to A-477; L-38 to A-477; D-39 to A-477; I-40 to A-477; T-41 to A-477; P-42 to A-477; P-43 to A-477; K-44 to A-477; E-45 to A-477; T-46 to A-477; L-47 to A-477; Q-48 to A-477; K-49 to A-477; D-50 to A-477; V-51 to A-477; E-52 to A-477; I-53 to A-477; T-54 to A-477; I-55 to A-477; V-56 to A-477; E-57 to A-377; T-58 to A-477; D-59 to A-477; Y-60 to A-477; N-61 A-477; E-62 to A-477; N-63 to A-477; V-64 to A-477; I-65 to A-477; I-66 to A-477; G-67 to A-477; Y-68 to A-477; K-69 to A-477; G-70 to A-477; Y-71 to A-477; Y-72 to A-477; Q-73 to A-477; A-74 to A-477; Y-75 to A-477; A-76 to A-477; Y-77 to A-477; N-78 to A-477; G-79 to A-477; G-80 to A-477; S-81 to A-477; L-82 to A-477; D-83 to A-477; P-84 to A-477; N-85 to A-477; T-86 to A-477; R-87 to A-477; V-88 to A-477; E-89 to A-477; E-90 to A-477; T-91 to A-477; M-92 to A-477; K-93 to A-477; T-94 to A-477; L-95 to A-477; N-96 to A-477; V-97 to A-477; G-98 to A-477; K-99 to A-477; E-100 to A-477; D-101 to A-477; L-102 to A-477; L-103 to A-477; M-104 to A-477; W-105 to A-477; S-106 to A-477; I-107 to A-477; R-108 to A-477; Q-109 to A-477; Q-110 to A-477; C-111 to A-477; E-112 to A-477; V-113 to A-477; G-114 to A-477; E-115 to A-477; E-116 to A-477; L-117 to A-477; I-118 to A-477; D-119 to A-477; R-120 to A-477; W-121 to A-477; G-122 to A-477; S-123 to A-477; D-124 to A-477; S-125 to A-477; D-126 to A-477; D-127 to A-477; C-128 to A-477; F-129 to A-477; R-130 to A-477; D-131 to A-477; N-132 to A-477; E-133 to A-477; G-134 to A-477; R-135 to A-477; G-136 to A-477; Q-137 to A-477; W-138 to A-477; V-139 to A-477; K-140 to A-477; G-141 to A-477; K-142 to A-477; E-143 to A-477; L-144 to A-477; V-145 to A-477; K-146 to A-477; R-147 to A-477; Q-148 to A-477; N-149 to A-477; N-150 to A-477; N-151 to A-477; H-152 to A-477; F-153 to A-477; A-154 to A-477; H-155 to A-477; H-156 to A-477; T-157 to A-477; C-158 to A-477; N-159 to A-477; K-160 to A-477; S-161 to A-477; W-162 to A-477; R-163 to A-477; C-164 to A-477; G-165 to A-477; I-166 to A-477; S-167 to A-477; T-168 to A-477; S-169 to A-477; K-170 to A-477; M-171 to A-477; Y-172 to A-477; S-173 to A-477; R-174 to A-477; L-175 to A-477; E-176 to A-477; C-177 to A-477; Q-178 to A-477; D-179 to A-477; D-180 to A-477; T-181 to A-477; D-182 to A-477; E-183 to A-477; C-184 to A-477; Q-185 to A-477; V-186 to A-477; Y-187 to A-477; I-188 to A-477; L-189 to A-477; D-190 to A-477; A-191 to A-477; E-192 to A-477; G-193 to A-477; N-194 to A-477; P-195 to A-477; I-196 to A-477; N-197 to A-477; V-198 to A-477; T-199 to A-477; V-200 to A-477; D-201 to A-477; T-202 to A-477; V-203 to A-477; L-204 to A-477; H-205 to A-477; R-206 to A-477; D-207 to A-477; G-208 to A-477; V-209 to A-477; S-210 to A-477; M-211 to A-477; I-212 to A-477; L-213 to A-477; K-214 to A-477; Q-215 to A-477; K-216 to A-477; S-217 to A-477; T-218 to A-477; F-219 to A-477; T-220 to A-477; T-221 to A-477; R-222 to A-477; Q-223 to A-477; I-224 to A-477; K-225 to A-477; A-226 to A-477; A-227 to A-477; C-228 to A-477; L-229 to A-477; L-230 to A-477; I-231 to A-477; K-232 to A-477; D-133 to A-477; D-234 to A-477; K-235 to A-477; N-236 to A-477; N-937 to A-477; P-238 to A-477; E-239 to A-477; S-240 to A-477; V-241 to A-477; T-242 to A-477; R-243 to A-477; E-244 to A-477; H-245 to A-477; C-246 to A-477; L-247 to A-477; I-248 to A-477; D-249 to A-477; N-250 to A-477; D-251 to A-477; I-252 to A-477; Y-253 to A-477; D-254 to A-477; L-255 to A-477; S-256 to A-477; K-157 to A-477; N-258 to A-477; T-259 to A-477; W-260 to A-477; N-261 to A-477; C-262 to A-477; K-263 to A-477; F-264 to A-477; N-265 to A-477; R-266 to A-477; C-267 to A-477; I-268 to A-477; K-269 to A-477; R-270 to A-477; K-271 to A-477; V-272 to A-477; E-273 to A-477; H-274 to A-477; R-275 to A-477; V-276 to A-477; K-277 to A-477; K-278 to A-477; R-279 to A-477; P-280 to A-477; P-281 to A-477; T-282 to A-477; W-283 to A-477; R-284 to A-477; H-285 to A-477; N-286 to A-477; V-287 to A-477; R-288 to A-477; A-289 to A-477; K-290 to A-477; Y-291 to A-477; T-292 to A-477; E-293 to A-477; G-294 to A-477; D-295 to A-477; T-296 to A-477; A-297 to A-477; T-298 to A-477; K-299 to A-477; G-300 to A-477; D-301 to A-477; L-302 to A-477; M-303 to A-477; H-304 to A-477; I-305 to A-477; Q-306 to A-477; E-307 to A-477; E-308 to A-477; L-309 to A-477; M-310 to A-477; Y-311 to A-477; E-312 to A-477; N-313 to A-477; D-314 to A-477; L-315 to A-477; L-316 to A-477; K-317 to A-477; M-318 to A-477; N-319 to A-477; I-320 to A-477; E-321 to A-477; L-322 to A-477; M-323 to A-477; H-324 to A-477; A-325 to A-477; H-326 to A-477; I-327 to A-477; N-328 to A-477; K-329 to A-477; L-330 to A-477; N-331 to A-477; N-332 to A-477; M-333 to A-477; L-334 to A-477; H-335 to A-477; D-336 to A-477; L-337 to A-477; I-338 to A-477; V-339 to A-477; S-340 to A-477; V-341 to A-477; A-342 to A-477; K-343 to A-477; V-344 to A-477; D-345 to A-477; E-346 to A-477; R-347 to A-477; L-348 to A-477; I-349 to A-477; G-350 to A-477; N-351 to A-477; L-352 to A-477; M-353 to A-477; N-354 to A-477; N-355 to A-477; S-356 to A-477; V-357 to A-477; S-358 to A-477; S-359 to A-477; T-360 to A-477; F-361 to A-477; L-362 to A-477; S-363 to A-477; D-364 to A-477; D-365 to A-477; T-366 to A-477; F-367 to A-477; L-368 to A-477; L-369 to A-477; M-370 to A-477; P-371 to A-477; C-372 to A-477; T-373 to A-477; N-374 to A-477; P-375 to A-477; P-376 to A-477; A-377 to A-477; H-378 to A-477; T-379 to A-477; S-380 to A-477; N-381 to A-477; C-382 to A-477; Y-383 to A-477; N-384 to A-477; N-385 to A-477; S-386 to A-477; I-387 to A-477; Y-388 to A-477; K-389 to A-477; E-390 to A-477; G-391 to A-477; R-392 to A-477; W-393 to A-477; V-394 to A-477; A-395 to A-477; N-396 to A-477; T-397 to A-477; D-398 to A-477; S-399 to A-477; S-400 to A-477; Q-401 to A-477; C-402 to A-477; I-403 to A-477; D-404 to A-477; F-405 to A-477; R-406 to A-477; N-407 to A-477; Y-408 to A-477; K-409 to A-477; E-410 to A-477; L-411 to A-477; A-412 to A-477; I-413 to A-477; H-414 to A-477; D-415 to A-477; V-416 to A-477; E-417 to A-477; F-418 to A-477; W-419 to A-477; I-420 to A-477; P-421 to A-477; T-422 to A-477; I-423 to A-477; G-424 to A-477; N-425 to A-477; T-426 to A-477; T-427 to A-477; Y-428 to A-477; H-429 to A-477; D-430 to A-477; S-431 to A-477; W-432 to A-477; K-433 to A-477; D-434 to A-477; A-435 to A-477; S-436 to A-477; G-437 to A-477; W-438 to A-477; S-439 to A-477; F-440 to A-477; I-441 to A-477; A-442 to A-477; Q-443 to A-477; Q-444 to A-477; K-445 to A-477; S-446 to A-477; N-447 to A-477; L-448 to A-477; I-449 to A-477; T-450 to A-477; T-451 to A-477; M-452 to A-477; E-453 to A-477; N-454 to A-477; T-455 to A-477; K-456 to A-477; F-457 to A-477; G-458 to A-477; G-459 to A-477; V-460 to A-477; G-461 to A-477; T-462 to A-477; S-463 to A-477; L-464 to A-477; S-465 to A-477; D-466 to A-477; I-467 to A-477; T-468 to A-477; S-469 to A-477; M-470 to A-477; A-471 to A-477; E- 472 to A-477; of SEQ ID NO:2. Polynucleotides encoding these polypeptides are also encompassed by the invention.

Further embodiments of the invention are directed to C-terminal deletions of the ISP polypeptide described by the general formula 22 to n, where n is an integer from 23–510 corresponding to the position of amino acid residue identified in SEQ ID NO:2 and preferably, corresponds to one of the C-terminal amino acid residues identified in the C-terminal deletions specified herein. In specific embodiments, C terminal deletions of the ISP polypeptide of the invention comprise or preferably, consist of, amino acid residues: H-23 to Q-510; H-23 to R-509; H-23 to N-508; H-23 to R-507; H-23 to N-506; H-23 to R-505; H-23 to I-504; H-23 to M-503; H-23 to C-502; H-23 to Y-501; H-23 to L-500; H-23 to F-499; H-23 to L-498; H-23 to I-497; H-23 to V-496; H-23 to I-495; H-23 to L-494; H-23 to I-493; H-23 to I-492; H-23 to V-491; H-23 to F-490; H-23 to N-489; H-23 to V-488; H-23 to V-487; H-23 to H-486; H-23 to G-485; H-23 to F-484; H-23 to M-483; H-23 to F-482; H-23 to S-481; H-23 to T-480; H-23 to L-479; H-23 to K-478; H-23 to A-477; H-23 to A-476; H-23 to L-475; H-23 to E-474; H-23 to G-473; H-23 to E-472; H-23 to A-471; H-23 to M-470; H-23 to S-469; H-23 to T-468; H-23 to I-467; H-23 to D-466; H-23 to S-465; H-23 to L-464; H-23 to S-463; H-23 to T-462; H-23 to G-461; H-23 to V-460; H-23 to G-459; H-23 to G-458; H-23 to F-457; H-23 to K-456; H-23 to T-455; H-23 to N-454; H-23 to E-453; H-23 to M-452; H-23 to T-451; H-23 to T-450; H-23 to I-449; H-23 to L-448; H-23 to N-447; H-23 to S-446; H-23 to K-445; H-23 to Q-444; H-23 to Q-443; H-23 to A-442; H-23 to I-441; H-23 to F-440; H-23 to S-439; H-23 to W-438; H-23 to G-437; H-23 to S-436; H-23 to A-435; H-23 to D-434; H-23 to K-433; H-23 to W-432; H-23 to S-431; H-23 to D-430; H-23 to H-429; H-2 to Y-428; H-23 to T-427; H-23 to T-426; H-23 to N-425; H-23 to G-424; H-23 to I-423; H-23 to T-422; H-23 to P-421; H-23 to I-420; H-23 to W-419; H-23 to F-418; H-23 to E-417; H-23 to V-416; H-23 to D-415; H-23 to H-414; H-23 to I-413; H-23 to A-412; H-23 to L-411; H-23 to E-410; H-23 to K-409; H-23 to Y-408; H-23 to N-407; H-23 to R-406; H-23 to F-405; H-23 to D-404; H-93 to I-403; H-23 to C-402; H-23 to Q-401; H-23 to S-400; H-23 to S-399; H-23 to D-398; H-23 to T-397; H-23 to N-396; H-23 to A-395; H-23 to V-394; H-23 to W-393; H-23 to R-392; H-23 to G-391; H-23 to E-390; H-23 to K-389; H-23 to Y-388; H-23 to I-387; H-23 to S-386; H-23 to N-385; H-23 to N-384; H-23 to Y-383; H-23 to C-382; H-23 to N-381; H-23 to S-380; H-23 to T-379; H-23 to H-378; H-23 to A-377; H-23 to P-376; H-23 to P-375; H-23 to N-374; H-23 to T-373; H-23 to C-372; H-23 to P-371; H-23 to M-370; H-23 to L-369; H-23 to L-368; H-23 to F-367; H-23 to T-366; H-23 to D-365; H-23 to D-364; H-23 to S-363; H-23 to L-362; H-23 to F- 361; H-23 to T-360; H-23 to S-359; H-23 to S-358; H-23 to V-357; H-23 to S-356; H-23 to N-355; H-23 to N-354; H-23 to M-353; H-23 to L-352; H-23 to N-351; H-23 to G-350; H-23 to I-349; H-23 to L-348; H-23 to R-347; H-23 to E-346; H-23 to D-345; H-23 to V-344; H-23 to K-343; H-23 to A-342; H-23 to V-341; H-23 to S-340; H-23 to V-339; H-23 to I-338; H-23 to L-337; H-23 to D-336; H-23 to H-335; H-23 to L-334; H-23 to M-333; H-23 to N-332; H-23 to N-331; H-23 to L-330; H-23 to K-329; H-23 to N-328; H-23 to I-327; H-23 to H-326; H-23 to A-325; H-23 to H-324; H-23 to M-323; H-23 to L-322; H-23 to E-321; H-23 to I-320; H-23 to N-319; H-23 to M-318; H-23 to K-317; H-23 to L-316; H-23 to L-315; H-23 to D-314; H-23 to N-313; H-23 to E-312; H-23 to Y-311; H-23 to M-310; H-23 to L-309; H-23 to E-308; H-23 to E-307; H-23 to Q-306; H-23 to I-305; H-23 to H-304; H-23 to M-303; H-23 to L-302; H-23 to D-301; H-23 to G-300; H-23 to K-299; H-23 to T-298; H-23 to A-297; H-23 to T-296; H-23 to D-295; H-23 to G-294; H-23 to E-293; H-23 to T-292; H-23 to Y-291; H-23 to K-290; H-23 to A-289; H-23 to R-288; H-23 to V-287; H-23 to N-286; H-23 to H-285; H-23 to R-284; H-23 to W-283; H-23 to T-282; H-23 to P-281; H-23 to P-280; H-23 to R-279; H-23 to K-278; H-23 to K-277; H-23 to V-276; H-23 to R-275; H-23 to H-274; H-23 to E-273; H-23 to V-272; H-23 to K-271; H-23 to R-270; H-23 to K-269; H-23 to I-268; H-23 to C-267; H-23 to R-266; H-23 to N-265; H-23 to F-264; H-23 to K-263; H-23 to C-262; H-23 to N-261; H-23 to W-260; H-23 to T-259; H-23 to N-258; H-23 to K-257; H-23 to S-256; H-23 to L-255; H-23 to D-254; H-23 to Y-253; H-23 to I-252; H-23 to D-251; H-23 to N-250; H-23 to D-249; H-23 to I-248; H-23 to L-247; H-23 to C-246; H-23 to H-245; H-23 to E-244; H-23 to R-243; H-23 to T-242; H-23 to V-241; H-23 to S-240; H-23 to E-239; H-23 to P-238; H-23 to N-237; H-23 to N-236; H-23 to K-235; H-23 to D-234; H-23 to D-233; H-23 to K-232; H-23 to I-231; H-23 to L-230; H-23 to L-229; H-23 to C-228; H-23 to A-227; H-23 to A-226; H-23 to K-225; H-23 to I-224; H-23 to Q-223; H-23 to R-222; H-23 to T-221; H-23 to T-220; H-23 to F-219; H-23 to T-218; H-23 to S-217; H-23 to K-216; H-23 to Q-215; H-23 to K-214; H-23 to L-213; H-23 to I-212; H-23 to M-211; H-23 to S-210; H-23 to V-209; H-23 to G-208; H-23 to D-207; H-23 to R-206; H-23 to H-205; H-23 to L-204; H-23 to V-203; H-23 to T-202; H-23 to D-201; H-23 to V-200; H-23 to T-199; H-23 to V-198; H-23 to N-197; H-23 to I-196; H-23 to P-195; H-23 to N-194; H-23 to G-193; H-93 to E-192; H-23 to A-191; H-23 to D-190; H-23 to L-189; H-23 to I-188; H-23 to Y-187; H-23 to V-186; H-23 to Q-185; H-23 to C-184; H-23 to E-183; H-23 to D-182; H-23 to T-181; H-23 to D-180; H-23 to D-179; H-23 to Q-178; H-23 to C-177; H-23 to E-176; H-23 to L-175; H-23 to R-174; H-23 to S-173; H-23 to Y-172; H-23 to H-2371; H-23 to K-170; H-23 to S- 169; H-23 to T-168; H-23 to S-167; H-23 to I-166; H-23 to G-165; H-23 to C-164; H-23 to R-163; H-23 to W-162; H-23 to S-161; H-23 to K-160; H-23 to N-159;

H-23 to C-158; H-23 to T-157; H-23 to H-156; H-23 to H-155; H-23 to A-154; H-23 to F-153; H-23 to H-152; H-23 to N-151; H-23 to N-150; H-23 to N-149; H-23 to Q-148; H-23 to R-147; H-23 to K-146; H-23 to V-145; H-23 to L-144; H-23 to E-143; H-23 to K-142; H-23 to G-141; H-23 to K-140; H-23 to V-139; H-23 to W-138; H-23 to Q-137; H-23 to G-136; H-23 to R-135; H-23 to G-134; H-23 to E-133; H-23 to N-132; H-23 to D-131; H-23 to R-130; H-23 to F-129; H-23 to C-128; H-23 to D-127; H-23 to D-126; H-23 to S-125; H-23 to D-124; H-23 to S-123; H-23 to G-122; H-23 to W-121; H-23 to R-120; H-23 to D-119; H-23 to I-118; H-23 to L-117; H-23 to E-116; H-23 to E-115; H-23 to G-114; H-23 to V-113; H-23 to E-112; H-23 to C-111; H-23 to Q-110; H-23 to Q-109; H-23 to R-108; H-23 to I-107; H-23 to S-106; H-23 to W-105; H-23 to H-2304; H-23 to L-103; H-23 to L-102; H-23 to D-101; H-23 to E-100; H-23 to K-99; H-23 to G-98; H-23 to V-97; H-23 to N-96; H-23 to L-95; H-23 to T-94; H-23 to K-93; H-23 to M-92; H-23 to T-91; H-23 to E-90; H-23 to E-89; H-23 to V-88; H-23 to R-87; H-23 to T-86; H-23 to N-85; H-23 to P-84; H-23 to D-83; H-23 to L-82; H-23 to S-81; H-23 to G-80; H-23 to G-79; H-23 to N-78; H-23 to Y-77; H-23 to A-76; H-23 to Y-75; H-23 to A-74; H-23 to Q-73; H-23 to Y-72; H-23 to Y-71; H-23 to G-70; H-23 to K-69; H-23 to Y-68; H-23 to G-67; H-23 to I-66; H-23 to I-65; H-23 to V-64; H-23 to N-63; H-23 to E-62; H-23 to N-61; H-23 to Y-60; H-23 to D-59; H-23 to T-58; H-23 to E-57; H-23 to V-56; H-23 to I-55; H-23 to T-54; H-23 to I-53; H-23 to E-52; H-23 to V-51; H-23 to D-50; H-23 to K-49; H-23 to Q-48; H-23 to L-47; H-23 to T-46; H-23 to E-45; H-23 to K-44; H-23 to P-43; H-23 to P-42; H-23 to T-41; H-23 to I-40; H-23 to D-39; H-23 to L-38; H-23 to N-37; H-23 to K-36; H-23 to I-35; H-23 to K-34; H-23 to Y-33; H-23 to P-32; H-23 to G-31; H-23 to T-30; H-23 to K-29; H-23 to M-28; H-23 to Q-27; H-23 to A-26; H-23 to N-25; H-23 to C-24; of SEQ ID NO:2. Polynucleotides encoding these polypeptides are also encompassed by the invention.

In other embodiments, the present invention provides polypeptides having one or more residues deleted from the amino terminus of the amino acid sequence of the ISP polypeptide depicted in FIG. 1D (SEQ ID NO:4). Particularly, in one embodiment, N-terminal deletions of the ISP polypeptide can be described by the general formula m to 530, where m is an integer from 1 to 529 corresponding to the position of amino acid residue identified in SEQ ID NO:4 and preferably, corresponds to one of the N-terminal amino acid residues identified in the N-terminal deletions specified herein. In specific embodiments, N-terminal deletions of the ISP polypeptide of the invention comprise, or preferably consist of, amino acid residues: L-2 to Y-530; L-3 to Y-530; V-4 to Y-530; N-5 to Y-530; Q-6 to Y-530; S-7 to Y-530; H-8 to Y-530; Q-9 to Y-530; G-10 to Y-530; F-11 to Y-530; N-12 to Y-530; K-13 to Y-530; E-14 to Y-530; H-15 to Y-530; T-16 to Y-530; S-17 to Y-530; K-18 to Y-530; H-239 to Y-530; V-20 to Y-530; S-21 to Y-530; A-22 to Y-530; I-23 to Y-530; V-24 to Y-530; L-25 to Y-530; Y-26 to Y-530; V-27 to Y-530; L-28 to Y-530; L-29 to Y-530; A-30 to Y-530; A-31 to Y-530; A-32 to Y-530; A-33 to Y-530; H-34 to Y-530; S-35 to Y-530; A-36 to Y-530; F-37 to Y-530; A-38 to Y-530; A-39 to Y-530; E-40 to Y-530; H-41 to Y-530; C-42 to Y-530; N-43 to Y-530; A-44 to Y-530; Q-45 to Y-530; M-46 to Y-530; K-47 to Y-530; T-48 to Y-530; G-49 to Y-530; P-50 to Y-530; Y-51 to Y-530; K-52 to Y-530; I-53 to Y-530; K-54 to Y-530; N-55 to Y-530; L-56 to Y-530; D-57 to Y-530; I-58 to Y-530; T-59 to Y-530; P-60 to Y-530; P-61 to Y-530; K-62 to Y-530; E-63 to Y-530; T-64 to Y-530; L-65 to Y-530; Q-66 to Y-530; K-67 to Y-530; D-68 to Y-530; V-69 to Y-530; E-70 to Y-530; I-71 to Y-530; T-72 to Y-530; I-73 to Y-530; V-74 to Y-530; E-75 to Y-530; T-76 to Y-530; D-77 to Y-530; Y-78 to Y-530; N-79 to Y-530; E-80 to Y-530; N-81 to Y-530; V-82 to Y-530; I-83 to Y-530; I-84 to Y-530; G-85 to Y-530; Y-86 to Y-530; K-87 to Y-530; G-88 to Y-530; Y-89 to Y-530; Y-90 to Y-530; Q-91 to Y-530; A-92 to Y-530; Y-93 to Y-530; A-94 to Y-530; Y-95 to Y-530; N-96 to Y-530; G-97 to Y-530; G-98 to Y-530; S-99 to Y-530; L-100 to Y-530; D-101 to Y-530; P-102 to Y-530; N-103 to Y-530; T-104 to Y-530; R-105 to Y-530; V-106 to Y-530; E-107 to Y-530; E-108 to Y-530; T-109 to Y-530; H-2310 to Y-530; K-111 to Y-530; T-112 to Y-530; L-113 to Y-530; N-114 to Y-530; V-115 to Y-530; G-116 to Y-530; K-117 to Y-530; E-118 to Y-530; D-119 to Y-530; L-120 to Y-530; L-121 to Y-530; H-2322 to Y-530; W-123 to Y-530; S-124 to Y-530; I-125 to Y-530; R-126 to Y-530; Q-127 to Y-530; Q-128 to Y-530; C-129 to Y-530; E-130 to Y-530; V-131 to Y-530; G-132 to Y-530; E-133 to Y-530; E-134 to Y-530; L-135 to Y-530; I-136 to Y-530; D-137 to Y-530; R-138 to Y-530; W-139 to Y-530; G-140 to Y-530; S-141 to Y-530; D-142 to Y-530; S-143 to Y-530; D-144 to Y-530; D-145 to Y-530; C-146 to Y-530; F-147 to Y-530; R-148 to Y-530; D-149 to Y-530; N-150 to Y-530; E-151 to Y-530; G-152 to Y-530; R-153 to Y-530; G-154 to Y-530; Q-155 to Y-530; W-156 to Y-530; V-157 to Y-530; K-158 to Y-530; G-159 to Y-530; K-160 to Y-530; E-161 to Y-530; L-162 to Y-530; V-163 to Y-530; K-164 to Y-530; R-165 to Y-530; Q-166 to Y-530; N-167 to Y-530; N-168 to Y-530; N-169 to Y-530; H-170 to Y-530; F-171 to Y-530; A-172 to Y-530; H-173 to Y-530; H-174 to Y-530; T-175 to Y-530; C-176 to Y-530; N-177 to Y-530; K-178 to Y-530; S-179 to Y-530; W-180 to Y-530; R-181 to Y-530; C-182 to Y-530; G-183 to Y-530; I-184 to Y-530; S-185 to Y-530; T-186 to Y-530; S-187 to Y-530; K-188 to Y-530; H-2389 to Y-530; Y-190 to Y-530; S-191 to Y- 530; R-192 to Y-530; L-193 to Y-530; E-194 to Y-530; C-195 to Y-530; Q-196 to Y-530; D-197 to Y-530; D-198 to Y-530; T-199 to Y-530; D-200 to Y-530; E-201 to Y-530; C-202 to Y-530; Q-203 to Y-530; V-204 to Y-530; Y-205 to Y-530; I-206 to Y-530; L-207 to Y-530; D-208 to Y-530; A-209 to Y-530; E-210 to Y-530; G-211 to Y-530; N-212 to Y-530; P-213 to Y-530; I-214 to Y-530; N-215 to Y-530; V-216 to Y-530; T-217 to Y-530; V-218 to Y-530; D-219 to Y-530; T-220 to Y-530; V-221 to Y-130; L-222 to Y-530; H-223 to Y-530; R-224 to Y-530; D-225 to Y-530; G-226 to Y-530; V-227 to Y-530; S-228 to Y-530; M-229 to Y-530; I-230 to Y-530; L-231 to Y-530; K-232 to Y-530; Q-233 to Y-530; K-234 to Y-530; S-235 to Y-530; T-236 to Y-530; F-237 to Y-530; T-238 to Y-530; T-239 to Y-530; R-240 to Y-530; Q-241 to Y-530; I-242 to Y-530; K-243 to Y-530; A-244 to Y-530; A-245 to Y-530; C-246 to Y-530; L-247 to Y-530; L-248 to Y-530; I-249 to Y-530; K-250 to Y-530; D-251 to Y-530; D-252 to Y-530; K-253 to Y-530; N-254 to Y-530; N-255 to Y-530; P-256 to Y-530; E-257 to Y-530; S-258 to Y-530; V-259 to Y-530; T-260 to Y-530; R-261 to Y-530; E-262 to Y-530; H-263 to Y-530; C-264 to Y-530; L-265 to Y-530; I-266 to Y-530; D-267 to Y-530; N-268 to Y-530; D-269 to Y-530; I-270 to Y-530; Y-271 to Y-530; D-272 to Y-530; L-273 to Y-530; S-274 to Y-530; K-275 to Y-530; N-276 to Y-530; T-277 to Y-530; W-278 to Y-530; N-279 to Y-530; C-280 to Y-530; K-281 to Y-530; F-282 to Y-530; N-283 to Y-530; R-284 to Y-530; C-285 to Y-530; I-286 to Y-530; K-287 to Y-530; R-288 to Y-530; K-289 to Y-530; V-290 to Y-530; E-291 to Y-530; H-292 to Y-530; R-293 to Y-530; V-294 to Y-530; K-295 to Y-530; K-296 to Y-530; R-297 to Y-530; P-298 to Y-530; P-299 to Y-530; T-300 to Y-530; W-301 to Y-530. R-302 to Y-530; H-303 to Y-530; N-304 to Y-530; V-305 to Y-530;

R-306 to Y-530; A-307 to Y-530; K-:308 to Y-530; Y-309 to Y-530; T-310 to Y-530; E-311 to Y-530; G-312 to Y-530; D-313 to Y-530; T-314 to Y-530; A-315 to Y-530; T-316 to Y-530; K-317 to Y-530; G-318 to Y-530; D-319 to Y-530; L-320 to Y-530; M-321 to Y-530; H-392 to Y-530; I-323 to Y-530; Q-324 to Y-530; E-325 to Y-530; E-326 to Y-530; L-327 to Y-530; M-328 to Y-530; Y-329 to Y-530; E-330 to Y-530; N-331 to Y-530; D-332 to Y-530; L-333 to Y-530; L-334 to Y-530; K-335 to Y-530; M-336 to Y-530; N-337 to Y-530; I-338 to Y-530; E-339 to Y-530; L-340 to Y-530; M-341 to Y-530; H-342 to Y-530; A-343 to Y-530; H-344 to Y-530; I-345 to Y-530; N-346 to Y-530; K-347 to Y-530; L-348 to Y-530; N-349 to Y-530; N-350 to Y-530; M-351 to Y-530; L-352 to Y-530; H-353 to Y-530; D-354 to Y-530; L-355 to Y-530; I-356 to Y-530; V-357 to Y-530; S-358 to Y-530; V-359 to Y-530; A-360 to Y-530; K-361 to Y-530; V-362 to Y-530; D-363 to Y-530; E-364 to Y-530; R-365 to Y-530; L-366 to Y-530; I-367 to Y-530; G-368 to Y-530; N-369 to Y-530; L-370 to Y-530; M-371 to Y-530; N-372 to Y-530; N-373 to Y-530; S- 374 to Y-530; V-375 to Y-530; S-376 to Y-530; S-377 to Y-530; T-378 to Y-530; F-379 to Y-530; L-380 to Y-530; S-381 to Y-530; D-382 to Y-530; D-383 to Y-530; T-384 to Y-530; F-385 to Y-530; L-386 to Y-530; L-387 to Y-530; M-388 to Y-530; P-389 to Y-530; C-390 to Y-530; T-391 to Y-530; N-392 to Y-530; P-393 to Y-530; P-394 to Y-530; A-395 to Y-530; H-396 to Y-530; T-397 to Y-530; S-398 to Y-530; N-399 to Y-530; C-400 to Y-530; Y-401 to Y-530; N-402 to Y-530; N-403 to Y-530; S-404 to Y-530; I-405 to Y-530; Y-406 to Y-530; K-407 to Y-530; E-408 to Y-530; G-409 to Y-530; R-410 to Y-530; W-411 to Y-530; V-412 to Y-530; A-413 to Y-130; N-414 to Y-530; T-415 to Y-530; D-416 to Y-530; S-417 to Y-530; S-418 to Y-530; Q-419 to Y-530; C-420 to Y-530; I-421 to Y-530; D-422 to Y-530; F-423 to Y-530; S-424 to Y-530; N-425 to Y-530; Y-426 to Y-530; K-427 to Y-530; E-428 to Y-530; L-429 to Y-530; A-430 to Y-530; I-431 to Y-530; D-432 to Y-530; D-433 to Y-530; D-434 to Y-530; V-435 to Y-530; E-436 to Y-530; F-437 to Y-530; W-438 to Y-530; I-439 to Y-530; P-440 to Y-530; T-441 to Y-530; I-442 to Y-530; G-443 to Y-530; N-444 to Y-530; T-445 to Y-530; T-446 to Y-530; Y-447 to Y-530; H-448 to Y-530; D-449 to Y-530; S-450 to Y-530; W-451 to Y-530; K-452 to Y-530; D-453 to Y-530; A-454 to Y-530; S-455 to Y-530; G-456 to Y-530; W-457 to Y-530; S-458 to Y-530; F-459 to Y-530; I-460 to Y-530; A-461 to Y-530; Q-462 to Y-530; Q-463 to Y-530; K-464 to Y-530; S-465 to Y-530; N-466 to Y-530; L-467 to Y-530; I-468 to Y-530; T-469 to Y-530; T-470 to Y-530; M-471 to Y-530; E-472 to Y-530; N-473 to Y-530; T-474 to Y-530; K-475 to Y-530; F-476 to Y-530; G-477 to Y-530; G-478 to Y-530; V-479 to Y-530; G-480 to Y-530; T-481 to Y-530; S-482 to Y-530; L-483 to Y-530; S-484 to Y-530; D-485 to Y-530; I-486 to Y-530; T-487 to Y-530; S-488 to Y-530; M-489 to Y-530; A-490 to Y-530; E-491 to Y-530; G-492 to Y-530; E-493 to Y-530; L-494 to Y-530; A-495 to Y-530; A-496 to Y-530; K-497 to Y-530; L-498 to Y-530; T-499 to Y-530; S-500 to Y-530; F-501 to Y-530; M-502 to Y-530; F-503 to Y-530; G-504 to Y-530; H-505 to Y-530; V-506 to Y-530; V-507 to Y-530; N-508 to Y-530; F-509 to Y-530; V-510 to Y-530; I-511 to Y-530; I-512 to Y-530; L-513 to Y-530; I-514 to Y-530; V-515 to Y-530; I-516 to Y-530; L-517 to Y-530; F-518 to Y-530; L-519 to Y-530; Y-520 to Y-530; C-521 to Y-530; M-522 to Y-530; I-523 to Y-530; R-524 to Y-530; N-525 to Y-530; of SEQ ID NO:4. Polynucleotides encoding these polypeptides are also encompassed by the invention.

In another embodiment, N-terminal deletions of the ISP polypeptide can be described by the general formula m to 496 where m is an integer from 2 to 495 corresponding to the amino acid residue identified in SEQ ID NO:4. In specific embodiments, N terminal deletions of the ISP polypeptide of the invention comprise, or preferably, consist of, amino acids L-2 to A-496; L-3 to A-496; V-4 to A-496; N-5 to A-496; Q-6 to A-496; S-7 to A-496; H-8 to A-496; Q-9 to A-496; G-10 to A-496; F-11 to A-496; N-12 to A-496; K-13 to A-496; E-14 to A-496; H-15 to A-496; T-16 to A-496; S-17 to A-496; K-18 to A-496; H-239 to A-496; V-20 to A-496; S-21 to A-496; A-22 to A-496; I-23 to A-496; V-24 to A-496; L-25 to A-496; Y-26 to A-496; V-27 to A-496; L-28 to A-496; L-29 to A-496; A-30 to A-496; A-31 to A-496; A-32 to A-496; A-33 to A-496; H-34 to A-496; S-35 to A-496; A-36 to A-496; F-37 to A-496; A-38 to A-496; A-39 to A-496; E-40 to A-496; H-41 to A-496; C-42 to A-496; N-43 to A-496; A-44 to A-496; Q-45 to A-496; M-46 to A-496; K-47 to A-496; T-48 to A-496; G-49 to A-496; P-50 to A-496; Y-51 to A-496; K-52 to A-496; I-53 to A-496; K-54 to A-496; N-55 to A-496; L-56 to A-496; D-57 to A-496; I-58 to A-496; T-59 to A-496; P-60 to A-496; P-61 to A-496; K-62 to A-496; E-63 to A-496; T-64 to A-496; L-65 to A-496; Q-66 to A-496; K-67 to A-496; D-68 to A-416; V-69 to A-496; E-70 to A-496; I-71 to A-496; T-72 to A-496; I-73 to A-496; V-74 to A-496; E-75 to A-496; T-76 to A-496; D-77 to A-496; Y-78 to A-496; N-79 to A-496; E-80 to A-496; N-81 to A-496; V-82 to A-496; I-83 to A-496; I-84 to A-496; G-85 to A-496; Y-86 to A-496; K-87 to A-496; G-88 to A-496; Y-89 to A-496; Y-90 to A-496; Q-91 to A-496; A-92 to A-496; Y-93 to A-496; A-94 to A-496; Y-95 to A-496; N-96 to A-496; G-97 to A-496; G-98 to A-496; S-99 to A-496; L-100 to A-496; D-101 to A-496; P-102 to A-496; N-103 to A-496; T-104 to A-496; R-105 to A-496; V-106 to A-496; E-107 to A-496; E-108 to A-496; T-109 to A-496; H-2310 to A-496; K-111 to A-496; T-112 to A-496; L-113 to A-496; N-114 to A-496; V-115 to A-496; G-116 to A-496; K-117 to A-496; E-118 to A-496; D-119 to A-496; L-120 to A-496; L-121 to A-496; H-2322 to A-496; W-123 to A-496; S-124 to A-496; I-125 to A-496; R-126 to A-496; Q-127 to A-496; Q-128 to A-496; C-129 to A-496; E-130 to A-496; V-131 to A-496; G-132 to A-496; E-133 to A-496; E-134 to A-496; L-135 to A-496; I-136 to A-496; D-137 to A-496; R-138 to A-496; W-139 to A-496; G-140 to A-496; S-141 to A-496; D-142 to A-496; S-143 to A-496; D-144 to A-496; D-145 to A-496; C-146 to A-496; F-147 to A-496; R-148 to A-496; D-149 to A-496; N-150 to A-496; E-151 to A-496; G-152 to A-496; R-153 to A-496; G-154 to A-496; Q-155 to A-496; W-156 to A-496; V-157 to A-496; K-158 to A-496; G-159 to A-496; K-160 to A-496; E-161 to A-496; L-162 to A-496; V-163 to A-496; K-164 to A-496; R-165 to A-496; Q-166 to A-496; N-167 to A-496; N-168 to A-496; N-169 to A-496; H-170 to A-496; F-171 to A-496; A-172 to A-496; H-173 to A-496; H-174 to A-496; T-175 to A-496; C-176 to A-496; N-177 to A-496; K-178 to A-496; S-179 to A-496; W-180 to A-496; R-181 to A-496; C-182 to A-496; G-183 to A-496; I-184 to A-496; S-185 to A-496; T-186 to A-496; S-187 to A-496; K-188 to A-496; H-2389 to A-496; Y-190 to A-496; S-191 to A-496; R-192 to A-496; L-193 to A-496; E-194 to A-496; C-195 to A-496; Q-196 to A-496; D-197 to A-496; D-198 to A-496; T-199 to A-496; D-200 to A-496; E-201 to A-496; C-202 to A-496; Q-203 to A-496; V-204 to A-496; Y-205 to A-496; I-206 to A-496; L-207 to A-496; D-208 to A-496; A-209 to A-496; E-210 to A-496; G-211 to A-496; N-212 to A-496; P-213 to A-496; I-214 to A-496; N-215 to A-496; V-216 to A-496; T-217 to A-496; V-218 to A-496; D-219 to A-496; T-220 to A-496; V-221 to A-496; L-222 to A-496; H-223 to A-496; R-224 to A-496; D-225 to A-496; G-226 to A-496; V-227 to A-496;

S-228 to A-496; M-229 to A-496; I-230 to A-496; L-231 to A-496; K-232 to A-496; Q-233 to A-496; K-234 to A-496; S-235 to A-496; T-236 to A-496; F-237 to A-496; T-238 to A-496; T-239 to A-496; R-240 to A-496; Q-241 to A-496; I-242 to A-496; K-243 to A-496; A-244 to A-496; A-245 to A-496; C-246 to A-496; L-247 to A-496; L-248 to A-496; I-249 to A-496; K-250 to A-496; D-251 to A-496; D-252 to A-496; K-253 to A-496; N-254 to A-496; N-255 to A-496; P-256 to A-496; E-257 to A-496; S-258 to A-496; V-259 to A-496; T-260 to A-496; R-261 to A-496; E-262 to A-496; H-263 to A-496; C-264 to A-496; L-265 to A-496; I-266 to A-496; D-267 to A-496; N-268 to A-496; D-269 to A-496; I-270 to A-496; Y-271 to A-496; D-272 to A-496; L-273 to A-496; S-274 to A-496; K-275 to A-496; N-276 to A-496; T-277 to A-496; W-278 to A-496; N-279 to A-496; C-280 to A-496; K-281 to A-496; F-282 to A-496; N-283 to A-496; R-284 to A-496; C-285 to A-496; I-286 to A-496; K-287 to A-496; R-288 to A-496; K-289 to A-496; V-290 to A-496; E-291 to A-496; H-292 to A-496; R-293 to A-496; V-294 to A-496; K-295 to A-496; K-296 to A-496; R-297 to A-496; P-298 to A-496; P-299 to A-496; T-300 to A-496; W-301 to A-496; R-302 to A-496; H-303 to A-496; N-304 to A-496; V-305 to A-496; R-306 to A-496; A-307 to A-496; K-308 to A-496; Y-309 to A-496; T-310 to A-496; E-311 to A-496; G-312 to A-496; D-313 to A-496; T-314 to A-496; A-315 to A-496; T-316 to A-496; K-317 to A-496; G-318 to A-496; D-319 to A-496; L-320 to A-496; M-321 to A-496; H-322 to A-496; I-323 to A-496; Q-324 to A-496; E-325 to A-496; E-326 to A-496; L-327 to A-496; M-328 to A-496; Y-329 to A-496; E-330 to A-496; N-331 to A-496; D-332 to A-496; L-333 to A-496; L-334 to A-496; K-335 to A-496; M-336 to A-496; N-337 to A-496; I-338 to A-496; E-339 to A-496; L-340 to A-496; M-341 to A-496; H-342 to A-496; A-343 to A-496; H-344 to A-496; I-345 to A-496; N-346 to A-496; K-347 to A-496; L-348 to A-496; N-349 to A-496; N-350 to A-496; M-351 to A-496; L-352 to A-496; H-353 to A-496; D-354 to A-496; L-355 to A-496; I-356 to A-496; V-357 to A-496; S-358 to A-496; V-359 to A-496; A-360 to A-496; K-361 to A-496; V-362 to A-496; D-363 to A-496; E-364 to A-496; R-365 to A-496; L-366 to A-496; I-367 to A-496; G-368 to A-496; N-369 to A-496; L-370 to A-496; M-371 to A-496; N-372 to A-496; N-373 to A-496; S-374 to A-496; V-375 to A-496; S-376 to A-496; S-377 to A-496; T-378 to A-496; F-379 to A-496; L-380 to A-496; S-381 to A-496; D-382 to A-496; D-383 to A-496; T-384 to A-496; F-385 to A-496; L-386 to A-496; L-387 to A-496; M-388 to A-496; P-389 to A-496; C-390 to A-496; T-391 to A-496; N-392 to A-496; P-393 to A-496; P-394 to A-496; A-395 to A-496; H-396 to A-496; T-397 to A-496; S-398 to A-496; N-399 to A-496; C-400 to A-496; Y-401 to A-496; N-402 to A-496; N-403 to A-496; S-404 to A-496; I-405 to A-496; Y-406 to A-496; K-407 to A-496; E-408 to A-496; G-409 to A-496; R-410 to A-496; W-411 to A-496; V-412 to A-496; A-413 to A-496. N-414 to A-496; T-415 to A-496; D-416 to A-496; S-417 to A-496; S-418 to A-496; Q-419 to A-496; C-420 to A-496; I-421 to A-496; D-422 to A-496; F-423 to A-496; S-424 to A-496; N-425 to A-496; Y-426 to A-496; K-427 to A-496; E-428 to A-496; L-429 to A-496; A-430 to A-496; I-431 to A-496; D-432 to A-496; D-433 to A-496; D-434 to A-496; V-435 to A-496; E-436 to A-496; F-437 to A-496; W-438 to A-496; I-439 to A-496; P-440 to A-496; T-441 to A-496; I-442 to A-496; G-443 to A-496; N-444 to A-496; T-445 to A-496; T-446 to A-496; Y-447 to A-496; H-448 to A-496; D-449 to A-496; S-450 to A-496; W-451 to A-496; K-452 to A-496; D-453 to A-496; A-454 to A-496; S-455 to A-496; G-456 to A-496; W-457 to A-496; S-458 to A-496; F-459 to A-496; I-460 to A-496; A-461 to A-496; Q-462 to A-496; Q-463 to A-496; K-464 to A-496; S-465 to A-496; N-466 to A-496; L-467 to A-496; I-468 to A-496; T-469 to A-496; T-470 to A-496; M-471 to A-496; E-472 to A-496; N-473 to A-496; T-474 to A-496; K-475 to A-496; F-476 to A-496; G-477 to A-496; G-478 to A-496; V-479 to A-496; G-480 to A-496; T-481 to A-496; S-482 to A-496; L-483 to A-496; S-484 to A-496; D-485 to A-496; I-486 to A-496; T-487 to A-496; S-488 to A-496; M-489 to A-496; A-490 to A-496; E-491 to A-496; of SEQ ID NO:4. Polynucleotides encoding these polypeptides are also encompassed by the invention.

Further embodiments of the invention are directed to C-terminal deletions of the ISP polypeptide depicted in FIG. 1D (SEQ ID NO:4) and described by the general formula 1 to n, where n is a number from 40 to 529 corresponding to the position of amino acid residue identified in SEQ ID NO:4 and preferably, corresponds to one of the C-terminal amino acid residues identified in the C-terminal deletions specified herein. In specific embodiments, C terminal deletions of the ISP polypeptide of the invention comprise or preferably, consist of, amino acid residues E-40 to Q-529; E-40 to R-528; E-40 to N-527; E-40 to R-526; E-40 to N-525; E-40 to R-524; E-40 to I-523; E-40 to M-522; E-40 to C-521; E-40 to Y-520; E-40 to L-519; E-40 to F-518; E-40 to L-517; E-40 to I-516; E-40 to V-515; E-40 to I-514; E-40 to L-513; E-40 to I-512; E-40 to I-511; E-40 to V-510; E-40 to F-509; E-40 to N-508; E-40 to V-507; E-40 to V-506; E-40 to H-505; E-40 to G- 504; E-40 to F-503; E-40 to M-502; E-40 to F-501; E-40 to S-500; E-40 to T-499; E-40 to L-498; E-40 to K-497; E-40 to A-496; E-40 to A-495; E-40 to L-494; E-40 to E-493; E-40 to G-492; E-40 to E-491; E-40 to A-490; E-40 to M-489; E-40 to S-488; E-40 to T-487; E-40 to I-486; E-40 to D-485; E-40 to S-484; E-40 to L-483; E-40 to S-482; E-40 to T-481; E-40 to G-480; E-40 to V-479; E-40 to G-478; E-40 to G-477; E-40 to F-476; E-40 to K-475; E-40 to T-474; E-40 to N-473; E-40 to E-472; E-40 to M-471; E-40 to T-470; E-40 to T-469; E-40 to I-468; E-40 to L-467; E-40 to N-466; E-40 to S-465; E-40 to K-464; E-40 to Q-463; E-40 to Q-462; E-40 to A-461; E-40 to I-460; E-40 to F-459; E-40 to S-458; E-40 to W-457; E-40 to G-456; E-40 to S-455; E-40 to A-454; E-40 to D-453; E-40 to K-452; E-40 to W-451; E-40 to S-450; E-40 to D-449; E-40 to H-448; E-40 to Y-447; E-40 to T-446; E-40 to T-445; E-40 to N-444; E-40 to G-443; E-40 to I-442; E-40 to T-441; E-40 to P-440; E-40 to I-439; E-40 to W-438; E-40 to F-437; E-40 to E-436; E-40 to V-435; E-40 to D-434; E-40 to D-433; E-40 to D-432; E-40 to I-431; E-40 to A-430; E-40 to L-429; E-40 to E-428; E-40 to K-427; E-40 to Y-426; E-40 to N-425; E-40 to S-424; E-40 to F-423; E-40 to D-422; E-40 to I-421; E-40 to C-420; E-40 to Q-419; E-40 to S-418; E-40 to S-417; E-40 to D-416; E-40 to T-415; E-40 to N-414; E-40 to A-413; E-40 to V-412; E-40 to W-411; E-40 to R-410; E-40 to G-409; E-40 to E-408; E-40 to K-107; E-40 to Y-406; E-40 to I-405; E-40 to S-404; E-40 to N-403; E-40 to N-402; E-40 to Y-401; E-40 to C-400; E-40 to N-399; E-40 to S-398; E-40 to T-397; E-40 to H-396; E-40 to A-395; E-40 to P-394; E-40 to P-393; E-40 to N-392; E-40 to T-391; E-40 to C-390; E-40 to P-389; E-40 to M-388; E-40 to L-387; E-40 to L-386; E-40 to F-385; E-40 to T-384; E-40 to D-383; E-40 to D-382; E-40 to S-381; E-40 to L-380; E-40 to F-379; E-40 to T-378; E-40 to S-377; E-40 to S-376; E-40 to V-375; E-40 to S-374; E-40 to N-373; E-40 to N-372; E-40 to M-371; E-40 to L-370; E-40 to N-369; E-40 to G-368; E-40 to I-367; E-40 to L-366; E-40 to R-365; E-40 to E-364; E-40 to D-363; E-40 to V-362; E-40 to K-361; E-40 to A-360; E-40 to V-359; E-40 to S-358; E-40 to V-357; E-40 to I-356; E-40 to L-355; E-40 to D-354; E-40 to H-353; E-40 to L-352; E-40 to M-351; E-40 to N-350; E-40 to N-349; E-40 to L-348; E-40 to K-347; E-40 to N-346; E-40 to I-345; E-40 to H-344; E-40 to A-343; E-40 to H-342; E-40 to M-341; E-40 to L-340; E-40 to E-339; E-40 to I-338; E-40 to N-337; E-40 to M-336; E-40 to K-335; E-40 to L-334; E-40 to L-333; E-40 to D-332; E-40 to N-331; E-40 to E-330; E-40 to Y-329; E-40 to M-328; E-40 to L-327; E-40 to E-326; E-40 to E-325; E-40 to Q-324; E-40 to I-323; E-40 to H-322; E-40 to M-321; E-40 to L-320; E-40 to D-319; E-40 to G-318; E-40 to K-317; E-40 to T-316; E-40 to A-315; E-40 to T-314; E-40 to D-313; E-40 to G-312; E-40 to E-311; E-40 to T-310; E-40 to Y-309; E-40 to K-308; E-40 to A-307; E-40 to R-306; E-40 to V-305; E-40 to N-304; E-40 to H-303; E-40 to R-302; E-40 to W-301; E-40 to T-300; E-40 to P-299; E-40 to P-298; E-40 to R-297; E-40 to K-296; E-40 to K-295; E-40 to V-294; E-40 to R-293; E-40 to H-292; E-40 to E-291; E-40 to V-290; E-40 to K-289; E-40 to R-288; E-40 to K-287; E-40 to I-286; E-40 to C-285; E-40 to R-284; E-40 to N-283; E-40 to F-282; E-40 to K-281; E-40 to C-280; E-40 to N-279; E-40 to W-278; E-40 to T-277; E-40 to N-276; E-40 to K-275; E-40 to S-274; E-40 to L-273; E-40 to D-272; E-40 to Y-271; E-40 to I-270; E-40 to D-269; E-40 to N-268; E-40 to D-267; E-40 to I-266; E-40 to L-265; E-40 to C-264; E-40 to H-263; E-40 to E-262; E-40 to R-261; E-40 to T-260; E-40 to V-259; E-40 to S-258; E-40 to E-257; E-40 to P-256; E-40 to N-255; E-40 to N-254; E-40 to K-253; E-40 to D-252; E-40 to D-251; E-40 to K-250; E-40 to I-249; E-40 to L-248; E-40 to L-247; E-40 to C-246; E-40 to A-245; E-40 to A-244; E-40 to K-243; E-40 to I-242; E-40 to Q-241; E-40 to R-240; E-40 to T-239; E-40 to T-238; E-40 to F-237; E-40 to T-236; E-40 to S-235; E-40 to K-234; E-40 to Q-233; E-40 to K-232; E-40 to L-231; E-40 to I-230; E-40 to M-229; E-40 to S-228; E-40 to V-227; E-40 to G-226; E-40 to D-225; E-40 to R-224; E-40 to H-223; E-40 to L-222; E-40 to V-221; E-40 to T-220; E-40 to D-219; E-40 to V-218; E-40 to T-217; E-40 to V-216; E-40 to N-215; E-40 to I-214; E-40 to P-213; E-40 to N-212; E-40 to G-211; E-40 to E-210; E-40 to A-209; E-40 to D-208; E-40 to L-207; E-40 to I-206; E-40 to Y-205; E-40 to V-204; E-40 to Q-203; E-40 to C-202; E-40 to E-201; E-40 to D-200; E-40 to T-199; E-40 to D-198; E-40 to D-197; E-40 to Q-196; E-40 to C-195; E-40 to E-194; E-40 to L-193; E-40 to R-192; E-40 to S-191; E-40 to Y-190; E-40 to E-4089; E-40 to K-188; E-40 to S-187; E-40 to T-186; E-40 to S-185; E-40 to I-184; E-40 to G-183; E-40 to C-182; E-40 to R-181; E-40 to W-180; E-40 to S-179; E-40 to K-178; E-40 to N-177; E-40 to C-176; E-40 to T-175; E-40 to H-174; E-40 to H-173; E-40 to A-172; E-40 to F-171; E-40 to H-170; E-40 to N-169; E-40 to N-168; E-40 to N-167; E-40 to Q-166; E-40 to R-165; E-40 to K-164; E-40 to V-163; E-40 to L-162; E-40 to E-161; E-40 to K-160; E-40 to G-159; E-40 to K-158; E-40 to V-157; E-40 to W-156; E-40 to Q-155; E-40 to G-154; E-40 to R-153; E-40 to G-152; E-40 to E-151; E-40 to N-150; E-40 to D-149; E-40 to R-148; E-40 to F-147; E-40 to C-146; E-40 to D-145; E-40 to D-144; E-40 to S-143; E-40 to D-142; E-40 to S-141; E-40 to G-140; E-40 to W-139; E-40 to R-138; E-40 to D-137; E-40 to I-136; E-40 to L-135; E-40 to E-134; E-40 to E-133; E-40 to G-132; E-40 to V-131; E-40 to E-130; E-40 to C-129; E-40 to Q-128; E-40 to Q-127; E-40 to R-126; E-40 to I-125; E-40 to S-124; E-40 to W-123; E-40 to E-4022; E-40 to L-121; E-40 to L-120; E-40 to D-119; E-40 to E-118; E-40 to K-117; E-40 to G-116; E-40 to V-115; E-40 to N-114; E-40 to L-113; E-40 to T-112; E-40 to K-111; E-40 to E-4010; E-40 to T-109; E-40 to E-108; E-40 to E-107; E-40 to V-106; E-40 to R-105; E-40 to T-104; E-40 to N-103; E-40 to P-102; E-40 to D-101; E-40 to L-100; E-40 to S-99; E-40 to G-98; E-40 to G-97; E-40 to N-96; E-40 to Y-95; E-40 to A-94; E-40 to Y-93; E-40 to A-92; E-40 to Q-91; E-40 to Y-90; E-40 to Y-89; E-40 to G-88; E-40 to K-87; E-40 to Y-86; E-40 to G-85; E-40 to I-84; E-40 to I-83; E-40 to V-82; E-40 to N-81; E-40 to E-80; E-40 to N-79; E-40 to Y-78; E-40 to D-77; E-40 to T-76; E-40 to E-75; E-40 to V-74; E-40 to I-73; E-40 to T-72; E-40 to I-71; E-40 to E-70; E-40 to V-69; E-40 to D-68; E-40 to K-67; E-40 to Q-66; E-40 to L-65; E-40 to T-64; E-40 to E-63; E-40 to K-62; E-40 to P-61; E-40 to P-60; E-40 to T-59; E-40 to I-58; E-40 to D-57; E-40 to L-56; E-40 to N-55; E-40 to K-54; E-40 to I-53; E-40 to K-52; E-40 to Y-51; E-40 to P-50; E-40 to G-49; E-40 to T-48; E-40 to K-47; E-40 to M46; E-40 to Q-45; E-40 to A-44; E-40 to N-43; E-40 to C-42; of SEQ ID NO:4. Polynucleotides encoding these polypeptides are also encompassed by the invention.

Further embodiments of the invention are directed to polypeptide fragments comprising, or preferably, consisting of, amino acids described by the general formula m to n, where m and n correspond to any one of the amino acid residues specified above for these symbols, respectively.

Polypeptide fragments of the present invention include polypeptides comprising an amino acid sequence contained in SEQ ID NO:2, SEQ ID NO:4, other polypeptides disclosed herein, or encoded by nucleic acids which hybridize (e.g., under stringent hybridization conditions) to the nucleotide sequence shown in FIG. 1A (SEQ ID NO:1), FIG. 1C (SEQ ID NO:3), or the complementary strands thereto. Protein fragments may be "free-standing," or comprised within a larger polypeptide of which the fragment forms a part or region, most preferably as a single continuous region. Representative examples of polypeptide fragments of the invention, include, for example, fragments that comprise or alternatively, consist of from about amino acid residues 1 to 20, 21 to 40, 41 to 60, 61 to 80, 81 to 100, 102 to 120, 121 to 140, 141 to 160, 161 to 180, 181 to 200, 201 to 220, 221 to 240, 241 to 260, 261 to 280, 281 to 310, 311 to 350, 351 to 400, 401 to 450, 451 to 496, 497 to 511, or 497 to 530, of SEQ ID NO:2, SEQ ID NO:4, or corresponding to other polypeptides disclosed herein. Moreover, polypeptide fragments can be at least about 20, 30, 40, 50, 60, 70, 80, 90, 100, 110, 120, 130, 140, or 150 amino acids in length. In this context "about" includes the particularly recited ranges, larger or smaller by several (5, 4, 3, 2, or 1) amino acids, at either extreme or at both extremes.

Among the especially preferred fragments of the invention are fragments characterized by structural or functional attributes of ISP. Such fragments include amino acid residues that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophillic regions, hydrophobic regions, alpha amphipathic regions, beta amphipathic regions, surface forming regions, and high antigenic index regions (i.e., having 4 or more contiguous amino acids, each of which have an antigenic index of greater than or equal to 1.5, as identified using the default parameters of the Jameson-Wolf program) of the ISP polypeptides disclosed in FIG. 1B or FIG. 1D. Certain preferred regions are those set out in FIGS. 11A and 11B and include, but are not limited to, regions of the aforementioned types identified by analysis of the amino acid sequence depicted in FIG. 1B and/or FIG. 1D, such preferred regions include; Garnier-Robson predicted alpha-regions, beta-regions, turn-regions, and coil-regions; Chou- Fasman predicted alpha-regions, beta-regions, turn-regions, and coil-regions; Kyte-Doolittle predicted hydrophilic and hydrophobic regions; Eisenberg alpha and beta amphipathic regions; Emini surface-forming regions; and Jameson-Wolf high antigenic index regions, as predicted using the default parameters of these computer programs. Polynucleotides encoding these polypeptides are also encompassed by the invention.

In preferred embodiments, the polypeptide fragments of the invention comprise or alternatively, consist of a domain of the ISP protein. In specific embodiments, the polypeptide fragments of the invention comprise, or alternatively, consist of, the extracellular domain of the ISP amino acid sequence shown in FIG. 1B (amino acid residues 22 to 487 in SEQ ID NO:2); the extracellular domain of the ISP amino acid sequence shown in FIG. 1D (amino acid residues 39 to 506 in SEQ ID NO:4); the ISP extracellular and transmembrane domain depicted in FIG. 1B; the ISP extracellular and one or both of the transmembrane domains depicted in FIG. 1D; the ISP extracellular and intracellular domains depicted in FIG. 1B, with all or part of the transmembrane domain deleted; or the ISP extracellular and intracellular domains depicted in FIG. 1D, with all or part of one or both of the transmembrane domains deleted.

In other embodiments, the fragments or polypeptides of the invention (i.e., those described herein) are not larger than 525, 500, 475, 450, 400, 425, 390, 380, 375, 350, 336, 334, 331, 300, 275, 250, 225, 200, 185, 175, 170, 165, 160, 155, 150, 145, 140, 135, 130, 125, 120, 115, 110, 105, 100, 90, 80, 75, 60, 50, 40, 30, or 25 amino acid residues in length.

As one of skill in the art will appreciate, ISP polypeptides, fragments, variants, derivatives, and analogs of the present invention can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., Nature 331:84–86 (1988)). Fusion proteins that have a disulfide-linked dimeric structure due to the IgG part can also be more efficient in binding and neutralizing other molecules than the monomeric ISP protein or protein fragment alone (Fountoulakis et al., J. Biochem. 270:3958–3964 (1995)).

In accordance with the present invention, novel variants of ISP are also described. These can be produced by deleting or substituting one or more amino acids of ISP. Natural mutations are called allelic variations. Allelic variations can be silent (no change in the encoded polypeptide) or may have altered amino acid sequence.

In order to retain, improve or alter the characteristics of native ISP, protein engineering may be employed. Recombinant DNA technology known to those skilled in the art can be used to create novel polypeptides. Muteins and deletions can show, e.g., enhanced activity or increased stability. In addition, they could be purified in higher yield and show better solubility at least under certain purification and storage conditions.

As indicated, changes are preferably of a minor nature, such as conservative amino acid substitutions that do not significantly affect the folding or activity of the protein (see Table 1).

TABLE 1

Conservative Amino Acid Substitutions

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

In specific embodiments, the number of substitutions, additions or deletions in the amino acid sequence of FIG. 1B or FIG. 1D and/or any of the polypeptides or fragments described herein (e.g., the extracellular domain of the polypeptide depicted in FIG. 1B, FIG. 1D, or other ISP polypeptide disclosed herein) is 75, 70, 60, 50, 40, 35, 30, 25, 20, 15, 10, 9, 8, 7, 6, 5, 4, 3, 2, 1 or 50–25, 50–40, 40–30, 30–20, 25–5, 20–10, 5–10, 1–5, 1–3 or 1–2.

A further aspect of the present invention arc fusions of ISP (or fragments of ISP) with other proteins or fragments thereof, such as fusions or hybrids with other proteins or protein fragments that would increase expression, secretion, or protein processing, e.g., signal sequences, such as the MPIF-1 leader sequence. Fusions with sequences from other cytokines, such as IL-1 or IL-6 are also envisioned. In the published European patent application no. 0205404, a hybrid (chimeric) interferon protein was produced, which was derived from lymphoblastoid interferons alpha-2 and alpha-3. The hybrid interferon produced valuable anti-viral and antiproliferative properties.

Fusions with parts of the constant domain of immunoglobulins (IgG) show often an increased half-life time in vivo. This has been shown, e.g., for chimeric proteins consisting of the first two domains of the human CD4-polypeptide with various domains of the constant regions of the heavy or light chains of mammalian immnunoglobulins (European Patent application, Publication No. 394 827, Traunecker et al., Nature 331, 84–86 (1988). Fusion proteins that have a disulfide-linked dimeric structure can also be more efficient in binding monomeric molecules alone (Fountoulakis et al., J. of Biochemistry, 270: 3958–3964, (1995)).

Native ISP (i.e., naturally occuring, wild type) and ISP polypeptides, fragments, variants, derivatives, and analogs, may be further modified to contain additional chemical moieties not normally part of the protein. Those derivatized moieties may improve the solubility, the biological half life or absorption of the protein. The moieties may also reduce or eliminate any desirable side effects of the proteins and the like. An overview for those moieties can be found in Remington's Pharmaceutical Sciences, 18th ed., Mack Publishing Co., Easton, Pa. (1990).

Polyethylene glycol (PEG) is one such chemical moiety which has been used for the preparation of therapeutic proteins. The attachment of PEG to proteins has been shown to protect against proteolysis, Sada et al., J. Fermentation Bioengineering 71:137–139 (1991). Various methods are available for the attachment of certain PEG moieties. For review, see: Abuchowski et al., in Enzymes as Drugs, Holcerberg and Roberts, eds., pp. 367–383 (1981). Many published patents describe derivatives of PEG and processes how to prepare them, e.g., Ono et al., U.S. Pat. No. 5,342,940; Nitecki et al., U.S. Pat. No. 5,089,261; Delgado et al., U.S. Pat. No. 5,349,052. Generally, PEG molecules are connected to the protein via a reactive group found on the protein. Amino groups, (e.g., on lysines or the amino terminus of the protein) are convenient for this attachment among others.

Further embodiments of the invention are directed to polypeptides having the amino acid sequence of the gp67 proteins of: *Orgyia pseudotsugata* multicapsid nuclear polyhedrosis virus (OpMNPV; as disclosed in Blissard et al., J. Virol. 170:537–555 (1989); genbank accession no. M22446, NID g332525), *Choristoneura fumiferana* multicapsid nuclear polyhedrosis virus (CfMNPV; as disclosed in Hill et al., 1994, J. Gen. Virol. 75:1811–1813; genbank accession no. L12412; NID g793913), or *Anagrapha falcifera* virus (as disclosed in genbank accession no. U64897; NID g2062364), the polypeptide sequences of each of which is herein incorporated by reference in its entirety. Additional embodiments are directed to fragments (i.e., portions, preferably of the extracellular domain), variants, derivatives, and analogs of these polypeptides which, preferably have ISP activity (e.g,. induction of interferon production, anti-viral activity, or anti-cancer activity).

Therapeutic Applications of ISP

As discussed above, the various classes of interferon (IFN-alpha, IFN-beta, and IFN-gamma) have been used in the treatment of numerous medical conditions:

Anti-viral: IFNs have been used clinically for anti-viral therapy, for example, in the treatment of AIDS (Lane, H. C., Semin. Oncol. 18:46–52 (October 1991)), viral hepatitis including chronic hepatitis B and hepatitis C (Woo, M. H. and Burnakis, T. G., Ann. Pharmacother. 31:330–337 (March 1997); Gibas, A. L., Gastroenterologist 1:129–142 (June 1993)), papilloma viruses (Levine et al., Urology 47:553–557 (April 1996)), herpes (Ho, M., Annu. Rev. Med. 38:51–59 (1987)), cytomegalovirus (CMV) (Yamamoto et al., Arch. Virol. 94:323–329 (1987)), viral encephalitis (Wintergerst et al., Infection 20:207–212 (July 1992)), and in the prophylaxis of rhinitis (Ho, M., Annu. Rev. Med. 38:51–59 (1987)).

Anti-parasitic: IFNs have been suggested for anti-parasite therapy, for example, IFN-gamma for treating Cryptosporidium parvum infection (Rehg, J. E., J. Infect. Des. 174:229–232 (July 1996)).

Anti-bacterial: IFNs have been used clinically for anti-bacterial therapy. For example, IFN-gamma has been used in the treatment of multidrug-resistant pulmonary tuberculosis (Condos et al., Lancet 349:1513–1515 (1997)).

Anti-cancer: Interferon therapy has been used in the treatment of numerous cancers (e.g., hairy cell leukemia (Hofmann et al., Cancer Treat. Rev. 12 (Suppl. B):33–37 (December 1985)), acute myeloid leukemia (Stone et al., Am. J. Clin. Oncol. 16:159–163 (April 1993)), osteosarcoma (Strander et al., Acta Oncol. 34:877–880 (1995)), basal cell carcinoma (Dogan et al., Cancer Lett. 91:215–219 (May 1995)), glioma (Fetell et al., Cancer 65:78–83 (January 1990)), renal cell carcinoma (Aso et al., Prog. Clin. Biol. Res. 303:653–659 (1989)), multiple myeloma (Peest et al., Br. J. Haematol. 94:425–432 (September 1996)), melanoma (Ikic et al., Int. J. Dermatol. 34:872–874 (December 1995)), and Hodgkin's disease (Rybak et al., J. Biol. Response Mod. 9:1–4 (February 1990)). Synergistic treatment of advanced cancer with a combination of alpha interferon and temozolomide has also been reported (Patent publication WO 9712630 to Dugan, M. H).

Immunotherapy: IFNs have been used clinically for immunotherapy or more particularly, immunosuppression, for example, to prevent graft vs. host rejection, or to curtail the progression of autoimmune diseases, such as arthritis, multiple sclerosis, or diabetes. IFN-beta is approved for sale in the United States for the treatment (i.e., as an immunosuppressant) of multiple sclerosis. Recently, it has been reported that patients with multiple sclerosis have diminished production of type I interferons and interleukin-2 (Wandinger et al., J. Neurol. Sci. 149:87–93 (1997)). In addition, immunotherapy with recombinant IFN-alpha (in combination with recombinant human IL-2) has been used successfully in lymphoma patients following autologous bone marrow or blood stem cell transplantation, and may intensify remission following transplantation (Nagler et al., Blood 89:3951–3959 (June 1997)).

Anti-allergy: The administration of IFN-gamma has been used in the treatment of allergies in mammals (See, Patent Publication WO 8701288 to Parkin, J. M. and Pinching, A. J.). It has also recently been demonstrated that there is a reduced production of IL-12 and IL-12-dependent IFN-gamma release in patients with allergic asthma (van der Pouw Kraan et al., J. Immunol. 158:5560–5565 (1997)). Thus, IFN may be useful in the treatment of allergy by inhibiting the humoral response.

Vaccine adjuvantation: Interferons may be used as an adjuvant or co-adjuvant to enhance or stimulate the immune response in cases of prophylactic or therapeutic vaccination (Heath, A. W. and Playfair, J. H. L., Vaccine 10:427–434 (1992)).

Thus, the ISP polypeptides of the present invention, or fragments, variants, derivatives, muteins, or analogs thereof may be employed clinically to stimulate interferon production in a mammalian, preferably human, host. Particularly, the polypeptides of the present invention, including fragments, variants, derivatives, muteins and analogs thereof, may be administered to a patient (e.g., mammal, preferably human), to stimulate alpha, beta, and/or gamma interferon production. Thus, polypeptides, fragments, variants, derivatives, and analogs of the present invention have prophylactic and therapeutic uses which include, but are not limited to, anti-viral therapy, anti-cancer therapy, anti-parasitic therapy, anti-bacterial therapy, treatment and prevention of allergy, immunotherapy, and/or in the treatment of any condition, such as those mentioned above, where an increased production of interferon is desired. The polypeptides of the invention may also be used as an adjuvant or co-adjuvant to enhance or stimulate the immune response in cases of prophylactic or therapeutic vaccination.

Further, there is provided a method of treating infection in a patient comprising administering an effective amount of a polypeptide, or fragment, variant, derivative or analog of the invention to a patient in need of anti-infective therapy. In a preferred embodiment the infection is of viral, bacterial, or parasitic etiology. In a particularly preferred embodiment, the infection is a viral infection.

Further, there is provided a method of treating cancer in a patient comprising administering an effective amount of a polypeptide, or fragment, variant, derivative or analog of the invention to a patient in need of anti-cancer therapy.

Further, there is provided a method of immunotherapy in a patient comprising administering an effective amount of a polypeptide, or fragment, variant, derivative or analog of the invention to a patient in need of immunotherapy.

The polypeptides, or fragments, variants, derivatives or analogs of the present invention may be employed in combination with a suitable pharmaceutically acceptable carrier to comprise a pharmaceutical composition. Such compositions comprise a therapeutically effective amount of the polypeptide (including fragments, variants, derivatives, and analogs as described herein), agonist or antagonist and a pharmaceutically acceptable carrier or excipient. Such a carrier includes, but is not limited to, saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such containers can be a notice in the form prescribed by a governmental agency regulating the manufacture, use or sale of pharmaceuticals or biological products, which notice reflects approval by the agency of manufacture, use or sale for human administration. In addition, the polypeptides, agonists and antagonists of the present invention may be employed in conjunction with other therapeutic compounds.

The ISP polypeptide, or fragment, variant, derivative or analog of the invention, having ISP activity may be administered in pharmaceutical compositions in combination with one or more pharmaceutically acceptable excipients. It will be understood that, when administered to a human patient, the total daily usage of the pharmaceutical compositions of the present invention will be decided by the attending physician within the scope of sound medical judgment. The specific therapeutically effective dose level for any particular patient will depend upon a variety of factors including the type and degree of the response to be achieved; the specific composition an other agent, if any, employed; the age, body weight, general health, sex and diet of the patient; the time of administration, route of administration, and rate of excretion of the composition; the duration of the treatment; drugs (such as a chemotherapeutic agent) used in combination or coincidental with the specific composition; and like factors well known in the medical arts. Suitable formulations, known in the art, can be found in Remington's Pharmaceutical Sciences (latest edition), Mack Publishing Company, Easton, Pa..

The ISP composition to be used in the therapy will be formulated and dosed in a fashion consistent with good medical practice, taking into account the clinical condition of the individual patient (especially the side effects of treatment with ISP alone), the site of delivery of the ISP composition, the method of administration, the scheduling of administration, and other factors known to practitioners. The "effective amount" of ISP for purposes herein (including a ISP effective amount) is thus determined by such considerations.

The pharmaceutical compositions may be administered in a convenient manner such as by the oral, topical, intravenous, intraperitoneal, intramuscular, intraarticular, subcutaneous, intranasal or intradermal routes. The pharmaceutical compositions are administered in an amount which is effective for treating and/or prophylaxis of the specific indication. In most cases, the dosage is from about 1 $\mu$g/kg to about 50 mg/kg body weight daily, taking into account the routes of administration, symptoms, etc. In the specific case of topical administration dosages are preferably administered from about 0.01 $\mu$g to 9 mg per cm$^2$.

As a general proposition, the total pharmaceutically effective amount of the ISP administered parenterally per more preferably dose will be in the range of about 1 $\mu$g/kg/day to 100 mg/kg/day of patient body weight, although, as noted above, this will be subject to therapeutic discretion. If given continuously, the ISP is typically administered at a dose rate of about 1 $\mu$g/kg/hour to about 50 $\mu$g/kg/hour, either by 1–4 injections per day or by continuous subcutaneous infusions, for example, using a mini-pump. An intravenous bag solution or bottle solution may also be employed.

The ISP is also suitably administered by sustained-release systems. Suitable examples of sustained-release compositions include semi-permeable polymer matrices in the form of shaped articles, e.g., films, or microcapsules. Sustained-release matrices include polylactides (U.S. Pat. No. 3,773,919, EP 58,481), copolymers of L-glutamic acid and gamma-ethyl-L-glutamate (Sidman et al., Biopolymers 22:547–556 (1983)), poly (2-hydroxyethyl methacrylate) (R. Langer et al., J. Biomed. Mater. Res. 15:167–277 (1981), and R. Langer, Chem. Tech. 12:98–105 (1982)), ethylene vinyl acetate (R. Langer et al., Id.) or poly-D-(−)-3-hydroxybutyric acid (EP 133,988). Sustained-release ISP compositions also include liposomally entrapped ISP. Liposomes containing ISP are prepared by methods known per se: DE 3,218,121; Epstein et al., Proc. Natl. Acad. Sci. USA 82:3688–3692 (1985); Hwang et al., Proc. Natl. Acad. Sci. USA 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal ISP therapy.

For parenteral administration, in one embodiment, the ISP is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the ISP polypeptide, fragment, variant derivative or analog, uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes. Suitable formulations, known in the art, can be found in Remington's Pharmaceutical Sciences (latest edition), Mack Publishing Company, Easton, Pa.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine, monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

ISP polypeptide, fragment, variant, derivative, or analog is typically formulated in such vehicles at a concentration of about 0.01 μg/ml to 100 mg/ml, preferably 0.01 μg/ml to 10 mg/ml, at a pH of about 3 to 8. It will be understood that the use of certain of the foregoing excipients, carriers, or stabilizers will result in the formation of ISP salts.

ISP to be used for therapeutic administration must be sterile. Sterility is readily accomplished by filtration through sterile filtration membranes (e.g.. 0.2 micron membranes). Therapeutic ISP compositions generally are placed into a container having a sterile access port, for example, an intravenous solution bag or vial having a stopper pierceable by a hypodermic injection needle.

ISP ordinarily will be stored in unit or multi-dose containers, for example, sealed ampules or vials, as an aqueous solution or as a lyophilized formulation for reconstitution. As an example of a lyophilized formulation, 10-ml vials are filled with 5 mil of sterile-Filtered 1% (w/v) aqueous ISP solution, and the resulting mixture is lyophilized. The infusion solution is prepared by reconstituting the lyophilized ISP using bacteriostatic water-for-injection.

Dosaging may also be arranged in a patient specific manner to provide a predetermined concentration of an ISP activity in the blood, as determined by an RIA technique, for instance. Thus patient dosaging may be adjusted to achieve regular on-going trough blood levels, as measured by RIA, on the order of from 50 to 1000 ng/ml, preferably 150 to 500 ng/ml.

Pharmaceutical compositions of the invention may be administered orally, rectally, parenterally, intracisternally, intradermally, intravaginally. intraperitoneally, topically (as by powders, ointments, gels, creams, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

In a specific embodiment, "pharmaceutically acceptable" means approved by a regulatory agency of the federal or a state government or listed in the U.S. Pharmacopeia or other generally recognized pharmacopeia for use in animals, and more particularly humans. Nonlimiting examples of suitable pharmaceutical carriers according to this embodiment are provided in "Remington's Pharmaceutical Sciences" by E. W. Martin, and include sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glyceral solutions can be employed as liquid carriers, particularly for injectable solutions.

Application of the Gene Encoding ISP in Gene Therapy

The gene encoding ISP or fragments of the ISP gene may also be employed in gene therapy to treat patients in need of increased interferon production. Such patients include those in need of anti-viral, anti-bacterial, anti-parasitic, anti-cancer therapy, or immunotherapy.

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle. Examples of other delivery vehicles include an HSV-based vector system, adeno-associated virus vectors, and inert vehicles, for example, dextran coated ferrite particles.

Retroviruses from which the retroviral plasmid vectors mentioned herein may be derived include, but are not limited to, Moloney Murine Leukemia virus, spleen necrosis virus, retroviruses such as Rous Sarcoma Virus, Harvey Sarcoma virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller et al., Biotechniques 7:980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or heterologous promoters, such as cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cell lines which may be transfected include, but are not limited to, the PE501, PA317, ψ-2, ψ-AM, PA12, T19–14X, VT-19-17-H2, ψCRE, ψCRIP, GP+E-86, GP+envAm12, and DAN cell lines as described in Miller, Human Gene Therapy 1:5–14 (1990), which is incorporated herein by reference in its entirety. The vector may transduce the packaging cells through any means known in the art.

Such means include, but are not limited to, electroporation, the use of liposomes, and CaPO4 precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

Other Applications of ISP

The ISP protein may also be employed as a positive control in experiments designed to identify peptidomimetics acting upon the ISP receptor.

In accordance with yet a further aspect of the present invention, there is provided a process for utilizing such polypeptides, or polynucleotides encoding such polypeptides, for in vitro purposes related to scientific research, synthesis of DNA, manufacture of DNA vectors and for the purpose of providing diagnostics and therapeutics for the treatment of human disease.

Fragments of the full length ISP gene may be used as a probe for screening cDNA libraries to isolate other genes that have a high sequence similarity to ISP genes or similar biological (e.g., anti-viral or anti-cancer) activity. Probes of this type generally have at least 20 bases. Preferably, however, the probes have at least 30 bases and generally do not exceed 50 bases, although they may have a greater number of bases. The probe may also be used to identify a cDNA clone corresponding to a full length transcript and a genomic clone or clones that contain the complete ISP gene including regulatory and promoter regions, exons, and introns. An example of a screen comprises isolating the coding region of the ISP gene by using the known DNA sequence to synthesize an oligonucleotide probe. Labeled oligonucleotides having a sequence complementary to that of the gene of the present invention are used to screen a library of human cDNA, genomic DNA or cDNA to determine which members of the library the probe hybridizes to.

In another embodiment, the invention provides a method for identification of ligands (e.g., receptors) for the ISP polypeptide. Any method suitable for detecting protein-protein interactions may be employed for identifying transmembrane proteins that interact with ISP. See generally, Phizicky et al., 1995, Microbiol Rev. 59:94–123, for a review of assays that may be routinely modified to isolate and characterize ISP ligands (e.g., receptors). Among the traditional methods which may be employed are co-immunoprecipitation, crosslinking and co-purification through gradients or chromatographic columns of cell lysates, or proteins obtained from cell lysates, and the ISP, to identify proteins in the lysate that interact with the ISP. For these assays, the ISP component used can be full length or a soluble derivative lacking the membrane-anchoring region (e.g., a truncated ISP in which the transmembrane domain is deleted resulting in a truncated molecule containing the extracellular domain). Once identified and isolated, the sequence of the ISP receptor can be ascertained using techniques well known to those of skill in the art, such as via the Edman degradation technique. (See, e.g., Creighton, 1983, "Proteins: Structures and Molecular Principles", W.H. Freeman & Co., N.Y., pp.34–49). The amino acid sequence obtained may be used as a guide for the generation of oligonucleotide mixtures that can be used to screen for gene sequences encoding such ISP ligands (e.g., receptors). Screening may be accomplished, for example, by standard hybridization or PCR techniques. Techniques for the generation of oligonucleotide mixtures and the screening are well-known. (See, e.g., Ausubel, supra., and PCR Protocols: A Guide to Methods and Applications, 1990, Innis, M. et al., eds. Academic Press, Inc., New York).

In one approach for ligand (e.g., receptor) identification, labeled ISP polypeptides can be photoaffinity linked with cell membrane or extract preparations that express the receptor molecule. Cross-linked material is resolved by PAGE analysis and exposed to x-ray film. The labeled complex containing the ligands (e.g., receptors) of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

Additionally, methods may be employed which result in the simultaneous identification of genes which encode the cognate ligand proteins interacting with ISP. These methods include, for example, probing expression, libraries, in a manner similar to the well known technique of antibody probing of λgt11 libraries, using labeled ISP polypeptide or fusion protein, e.g., an ISP polypeptide fused to a marker (e.g., an enzyme, fluor, luminescent protein, or dye), or an Ig-Fc domain.

In a specific embodiment, protein interactions between ISP polypeptides and its cognate ligands (e.g., receptors) are detected in vivo, using the two-hybrid system. One version of this system has been described (Chien et al., 1991, Proc. Natl. Acad. Sci. USA, 88:9578–9582) and is commercially available from Clontech (Palo Alto, Calif.).

In another embodiment, the gene encoding the receptor is identified via ligand panning and FACS sorting (Coligan et al., Current Protocols in Immun., 1(2), Chapter 5 (1991)). Preferably, expression cloning is employed wherein polyadenylated RNA is prepared from a cell responsive to the polypeptides, and a cDNA library created from this RNA is divided into pools and used to transfect COS cells or other cells that are not responsive to the polypeptides. Transfected cells which are grown on glass slides are exposed to the labeled polypeptides. The polypeptides can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an iterative sub-pooling and rescreening process, eventually yielding single clones that encodes the putative receptor.

In another embodiment, the invention provides a method of screening compounds to identify those which antagonize or agonize the action of ISP, as measured by IFN production. An example of such an assay comprises culturing (i.e., contacting) a responding cell type (e.g., normal dermal fibroblasts), ISP, and a compound to be screened, and comparing levels of ISP produced by this mixture with that observed when the responding cell type is cultured with the same concentration of ISP, under the same or similar conditions, but in the absence of the compound to be screened. A compound that acts as an ISP agonist increases the production of IFN relative to that observed when ISP and the responding cell type are cultured in the absence of the test compound, whereas a compound that acts as an antagonist of ISP activity decreases the production of IFN, when compared to that observed when ISP and the responding cell type are cultured in the absence of the test compound.

EXAMPLES

Materials and Methods

Mice: Male A/J mice (7–10 weeks) were purchased from Harlan Sprague-Dawley. Female C57BU6 NCr mice were purchased from Charles River Labs. Mice were maintained according to USDA recommended standards in microisolator cages with recycled paper bedding (Harlan Sprague Dawley), and provided with pelleted rodent diet (Harlan Sprague Dawley) and bottled drinking water on an ad libitum basis.

Virus: *Autographica californica* nuclear polyhedrosis virus (AcNPV) clone 6 (C6) was obtained from the American Type Culture Collection (ATCC)(Rockville, Md.). Frozen stocks of EMCV (EMC strain VR-129), VSV (Indiana strain), and CMV (Towne strain) were also obtained from the American Type Culture Collection (ATCC) (Rockville, Md.).

Cell lines: Normal human dermal embryonic fibroblasts (NHDF), were obtained from Clonetics, Inc. (San Diego, Calif.) and maintained in DMEM containing 10% FBS. Murine Balb/c C.7 cells were obtained from the ATCC (Rockville, Md.) and maintained in DMEM containing 10% FBS. *Spodoptera frugiperda* (SF9) cells were also obtained from the ATCC.

Anti-viral assay: The ability of a given sample to elicit an anti-viral state was assessed using a modified version of the assay developed by Finter et al. (Finter, N. B., Nature 206:597–599 (1965); Finter, N. B., J. Gen. Virol 1:395–397 (1967); Finter. N. B. J. Immunol 98:88–93 (1967); Finter, N. B., Methods Enzymol. 78:14–22 (1981); Johnston, M. D. & Finter, N. B., Tex. Rep. Biol. Med. 41:19–22 (1981)).

Briefly, NHDF cells ($2 \times 10^4$ cells/well) were dispensed into 96-well, flat-bottom plates in a total volume of 100 µl of medium (DMEM containing 10% FBS) and incubated overnight at 37° C. in a humidified environment. Medium was then removed and 100 µl of medium containing various dilutions of test samples or control proteins (IFN-alpha, IFN-beta, or IFN-gamma) was added. Cultures were incubated for an additional 24 hours at which time medium was removed and 100 µl of infectious virus (EMCV, VSV, or CMV) added. After an additional 24 hour incubation, cells were washed twice with PBS and stained by addition of 50 µl of an aqueous solution containing 1% crystal violet and 15% ETOH. The extent of protection was quantitated by extraction of dye from stained cells using a 70% ethanol/1% acetic acid solution. The amount of dye extracted was quantitated by absorbance determination at 580 nm in a Molecular Devices SpectraMAX 250 Reader. The resultant data was analyzed using the associated Sof MAX™PRO program.

In vivo analyses: PBS, mIFNgamma (specific activity= $2 \times 10^7$ U/mg), hIFNgamana (specific activity= $2 \times 10^7$ U/mg), hIFNalpha A/D (specific activity= $5 \times 10^7$ U/mg), and ISP were administered individually to mice (10 mice/treatment group) at 20 and 1 hour prior to a single viral challenge with $2 \times 10^4$ pfu of EMCV. All injections were administered i.p. (200 µl/injection). The survival of mice was monitored for 3 weeks post EMCV challenge. Mice receiving a second viral challenge ($2 \times 10^4$) were monitored for an additional 21 days. In each experiment a negative control group was included that received saline but no virus.

Monocite isolation: Peripheral blood mononuclear cells (PBMC) were purified from donor blood buffy coats (supplied by American Red Cross) by Histopaque (Sigma) density gradient centrifugation. Monocytes were then separated from other cell types by counterflow centrifugation using the JE-6B-elutriator system (Beckman). PBMC, resuspended in HBSS ($Ca^{2+}$ and $Mg^{2+}$ free) plus 0.5% BSA and 0.25 mM EDTA, were loaded in the Sanderson chamber at an initial flow rate of 10 ml/min, the rotor speed being 2500 rpm and the temperature 10° C. Subsequently, the flow rate was increased stepwise to obtain elutriated lymphocytes and monocyte fractions.

IFN-alpha ELISA: The ELISA kit was purchased from Pestka Biomedical Laboratories, and the assay was performed as specified by the manufacturer.

Example 1

Demonstration of Anti-Viral Activity on Normal Human Dermal Fibroblasts

The anti-viral activity contained within supernatants from baculovirus infected Sf9 cultures was first defined using a modified Finter assay system as described above in the section entitled "Materials and Methods." As shown in FIG. 2, NHDF cells can be protected from the cytopathic effects of the EMCV virus by ISP in a dose dependent manner. The positive control in the assay is IFN-alpha, a protein that is known to induce an anti-viral state among NHDF cells. This assay system was used to follow the purification of ISP.

Example 2

Purification of ISP

A. Biochemical Purification

Figure 3:
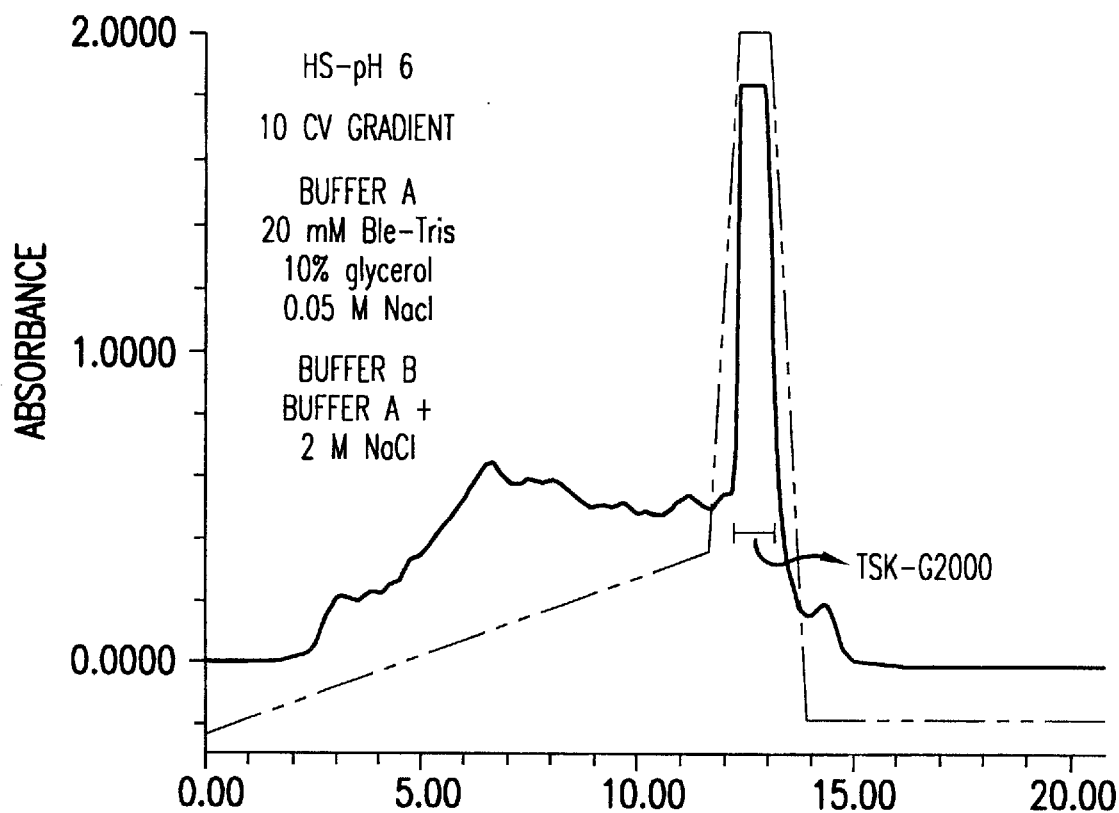
FIG. 3 shows an elution profile of supernatants obtained from baculovirus infected Sf9 cells. The solid line represents the absorbance at 215 nm while the dashed line depicts the salt gradient used to elute material from the HS column. The fractions marked with an arrow contained the majority of anti-viral activity and were thus pooled, concentrated, and applied to the TSK-G2000 sizing column.

ISP was purified from supernatants obtained from baculovirus infected Sf9 cells that were harvested 24 hours post infection. Supernatants were clarified by centrifugation (500 g 15 min.) and then applied to a single HS column run at pH6 (HS-6) with a 10 CV gradient from 0–25% B followed by a step gradient to 100% B (FIG. 3). Individual fractions were tested in the anti-viral assay described above in "Materials and Methods." It was determined that the majority of activity eluted during the later step gradient (25%–100%). The fractions containing the majority of ISP activity were pooled and applied to a sizing column (TSK G2000SW$_{XL}$). Previous attempts at size fractionation have been largely unsuccessful due to the loss of virtually all activity during the run. In an effort to identify a buffer system that would allow size fractionation of ISP without loss of activity, several buffer systems were tested for their effects on the biological activity of ISP.

Figure 4:
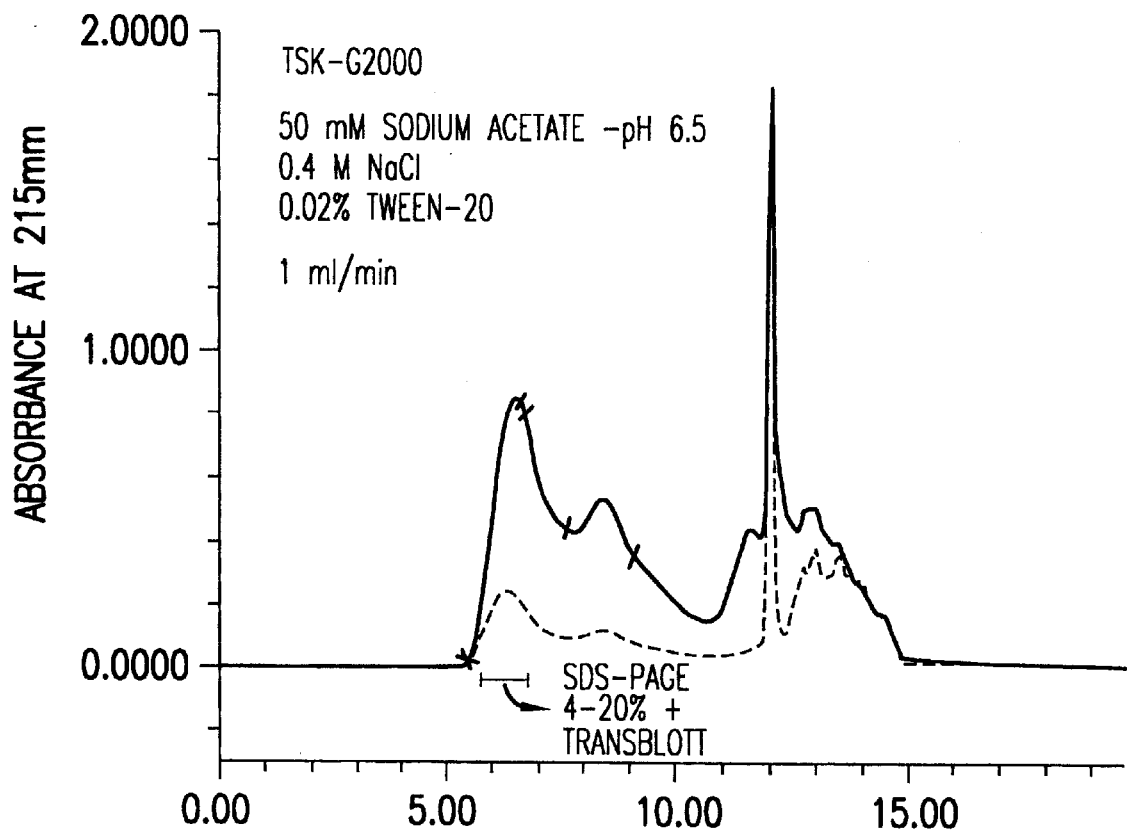
FIG. 4 shows an elution profile of pooled fractions from the HS column. The solid and dashed lines depict the absorbance at 215 and 280 nm, respectively. The majority of ISP activity eluted in Fraction 1.
Figure 5:
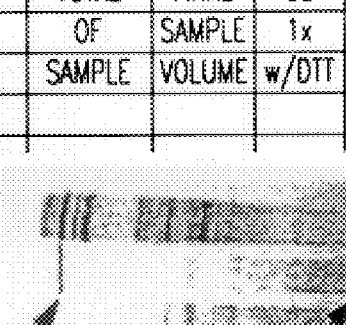
FIG. 5 shows an SDS-PAGE (4–20%) analysis of TSK-G2000 fractionated ISP. Lanes 1–4 were run under non-reducing conditions, while lanes 6–10 were run in the presence of DTT (i.e., reduced). The single band marked with an arrow in lane 7 was transblotted and prepared for microsequencing.
Figure 7:
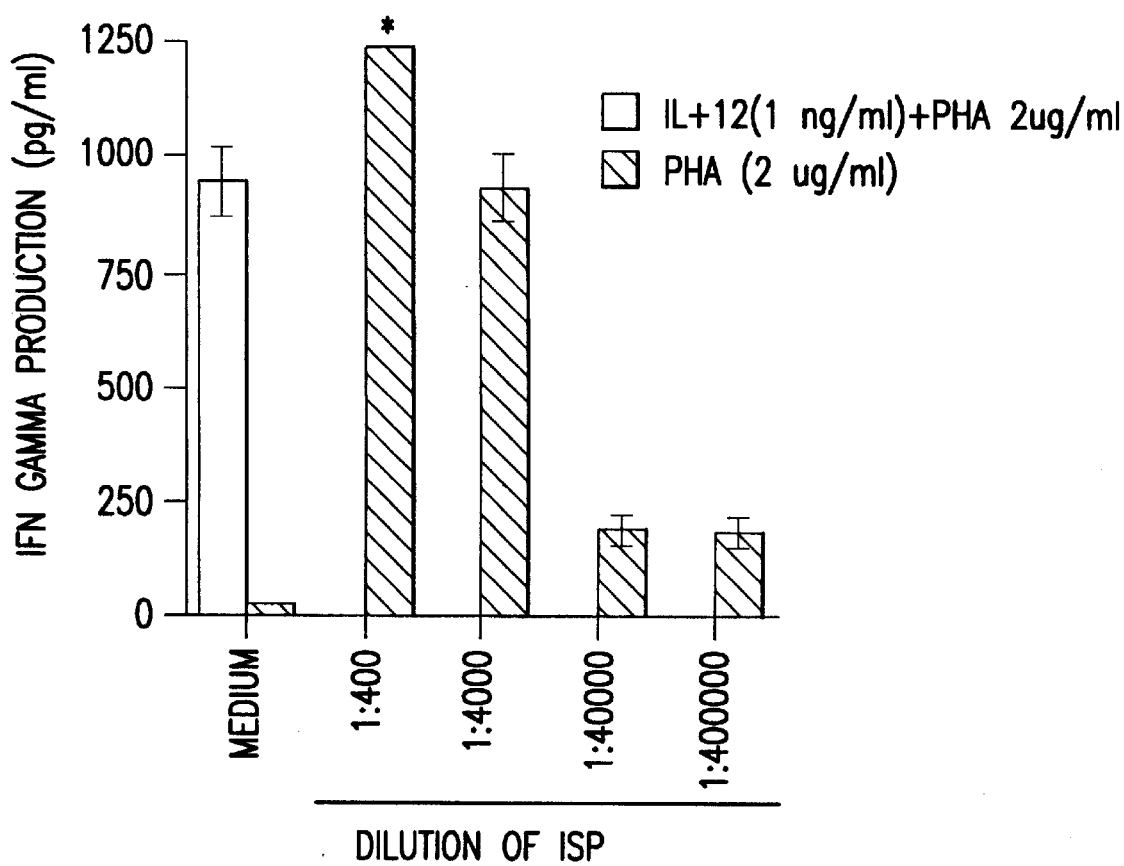
FIG. 7 is a bar graph showing the effect of ISP on IFN-gamma production by phytohemagglutinin (PHA) stimulated peripheral blood mononuclear cells (PBMCs) over 48 hours. The figure shows that ISP induces PHA stimulated PBMC to secrete IFN-gamma. IFN-gamma production by PBMC was monitored by ELISA. IL-12, a known inducer of IFN-gamma was used as a positive control. ISP induced IFN-gamma production at levels comparable to that observed with 1 ng/ml IL-12.
Figure 8:
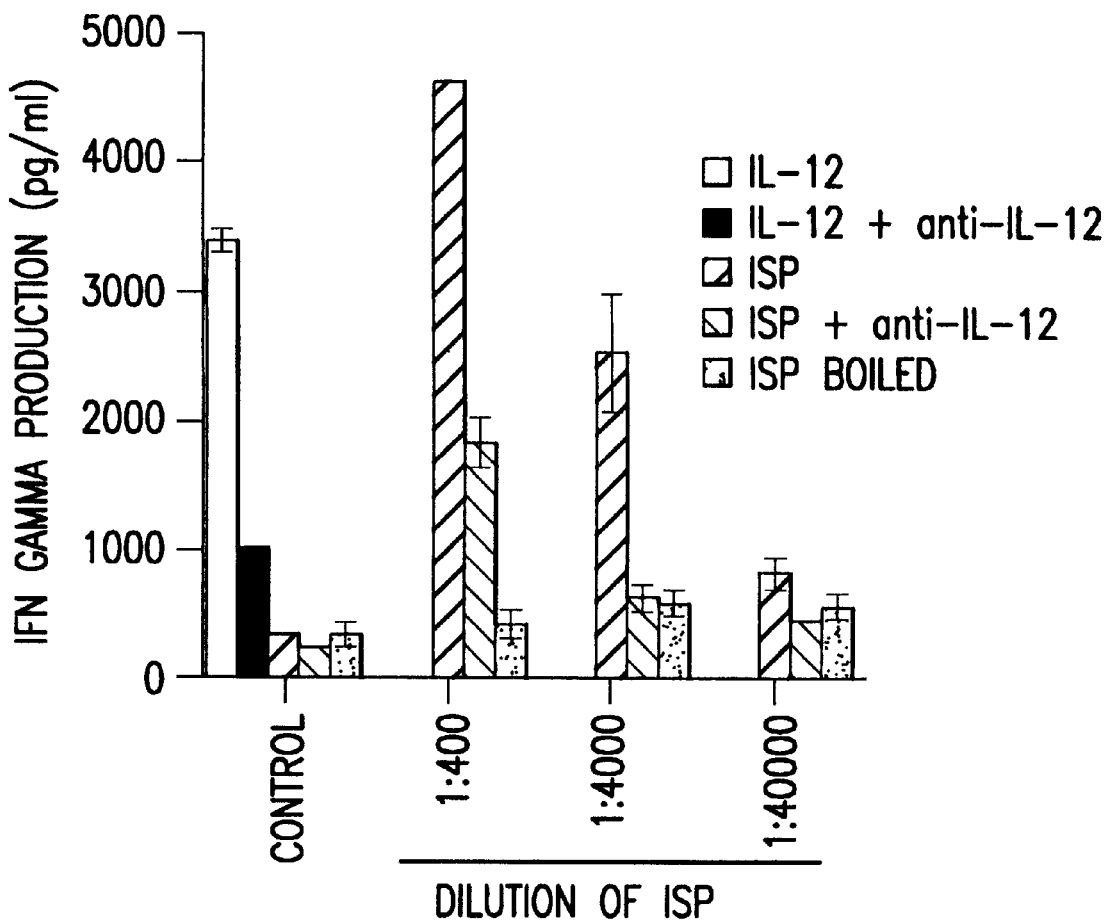
FIG. 8 is a bar graph showing that ISP induced IFN-gamma production by PHA stimulated PBMC was IL-12 dependent. The positive control in this experiment was IL-12. As expected, an anti-IL-12 monoclonal antibody inhibited IL-12 induced IFN-gamma production. The same antibody also inhibited ISP induced IFN-gamma production, suggesting that ISP works through IL-12.
Figure 9A:
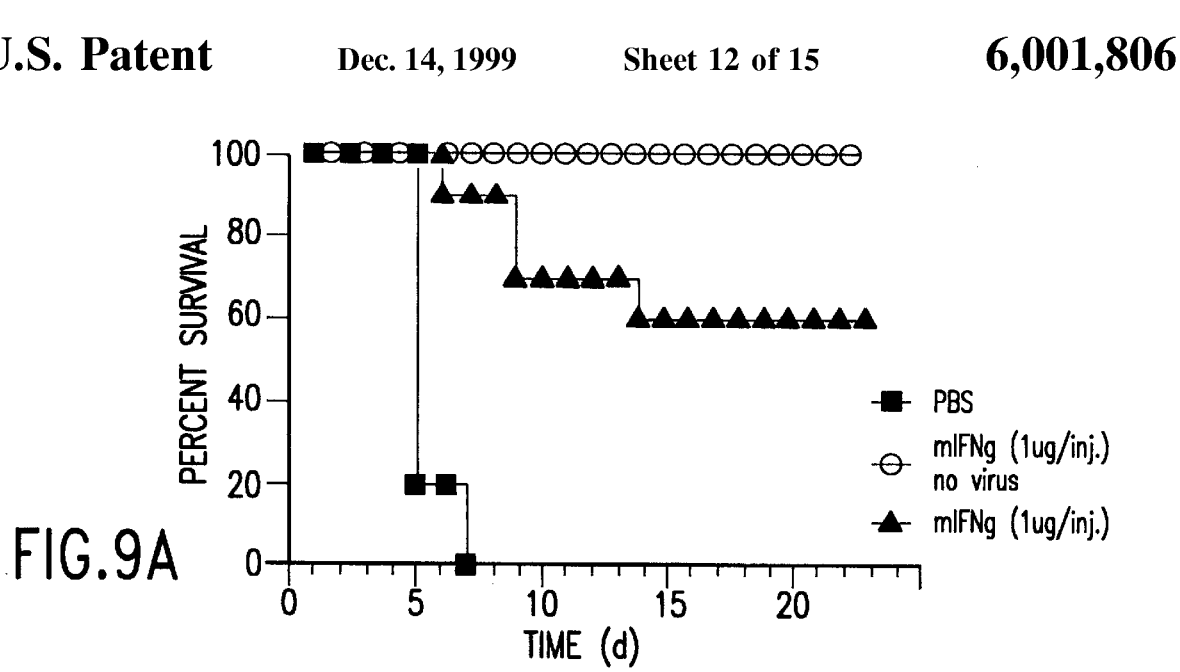
FIGS. 9A, 9B, and 9C are graphs depicting the anti-viral effect of ISP, IFN-gamma, and human IFN-alpha A/D on mice challenged with EMCV.
Figure 9B:
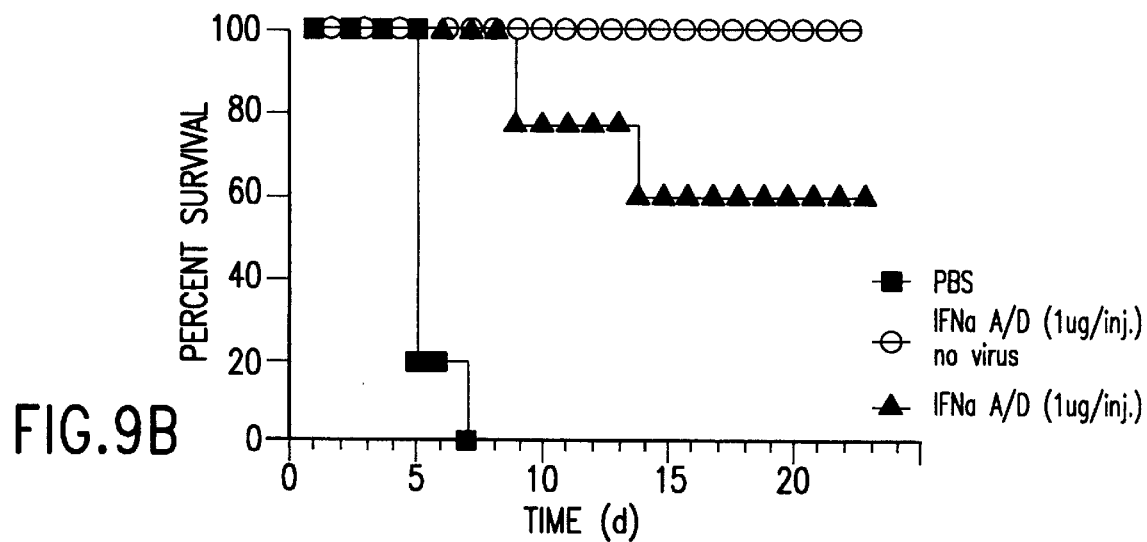
Figure 9C:
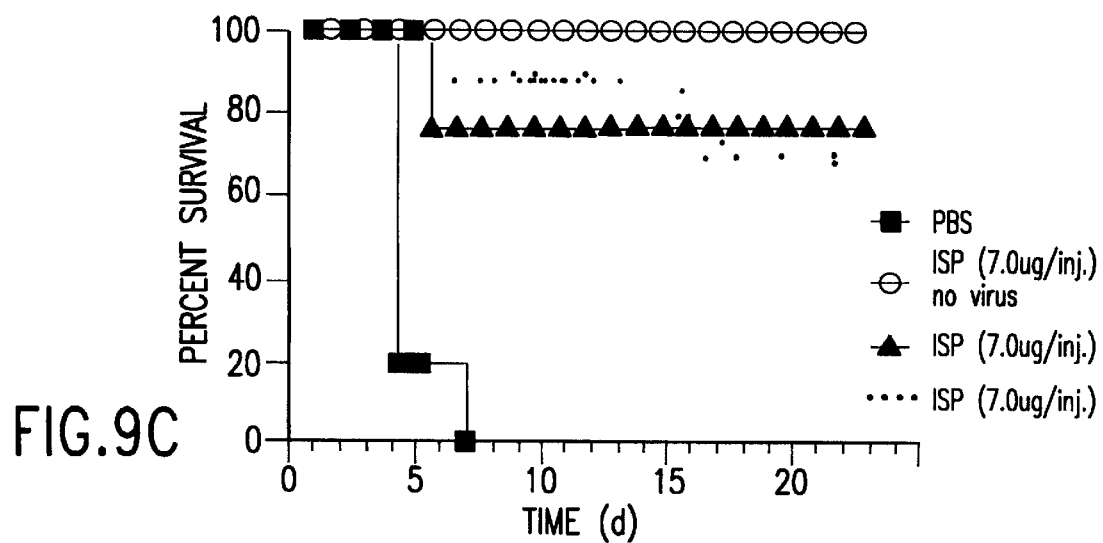

ISP was far less sensitive to urea than guanidine with full activity being detected in the presence of 4M and 1M, respectively. Accordingly, four buffer systems were used for sizing: running buffer alone (RB=50 mM NaAc pH6, 0.4M NaCl), RB+3M urea, RB+0.5M guanidine, and RB+0.02% Tween 20. Each system yielded similar elution profiles (FIG. 4) showing the RB+0.02% Tween 20 buffer elution with the majority of ISP activity eluting in the first fraction. However, in RB, guanidine, and urea, only 1–4% of the starting activity was recovered compared to greater than 50% recovery in the presence of Tween 20. As shown in FIG. 5, the size fractionation of ISP in the presence of Tween 20 resulted in a dramatic purification of ISP as assessed by PAGE. Under both non-reducing (NR, lane 1) and reducing (RED, lane 6) conditions the reference lot clearly contained 30–50 distinct protein bands. The size fractionated material from fractions 1, 2, and 3 (lanes 2–4 and 7–9) contains many fewer bands. In particular, the most active fraction #1 contains three or four prominent bands and an equal number of minor bands. As shown in FIG. 4, the NR fraction #1 contained two high molecular weight components not seen in other lanes and aggregated material that did not enter the stacking gel (see the 3 bands in lane 2 with arrows). Similarly, the RED fraction #1 contained a major protein having a molecular weight of approximately 66K that is not observed in other lanes (see the lane 7 band with arrow in FIG. 5). Polyclonal antibodies to ISP and the correlation of activity being found only in fraction 1 indicated the unique protein of interest would be the latter 66K band in lane 7. This protein was purified by SDS-PAGE, transblotted to a ProBlott membrane, and subjected to N-terminal microsequencing. This method identified two components corresponding to the proteins UDP-glucosyl transferase and GP-67 envelope glycoprotein from the baculovirus, *Autographa californica* (FIG. 6).

B. Monoclonal Antibody Production and Utility in Purification of ISP

Partially purified ISP (100 μl) was injected subcutaneously into a single Armenian hamster (Cytogen Research and Development, West Roxbery, Mass.). The first injection was made in Freund's complete adjuvant in a ratio of 1:1. At ten-day intervals, the hamster received an additional three injections of ISP in Freund's incomplete adjuvant (1:1) intraperitoneally. Following a four-week rest period, a single intravenous injection of ISP was administered. Three days later, the animal was sacrificed, serum collected, and splenocytes prepared for fusion with the myeloma cell line P3X63Ag8.653. The resultant hybridomas were isolated and supernatants screened for their ability to inhibit ISP-induced IFN secretion by the RAW 264.7 macrophage cell line.

The initial screening identified 39 inhibitory antibodies of which 11 were cloned and re-screened. Six inhibitory hybridomas were recloned. Supernatants from one of these clones (6E11.9) were used to immnunoprecipitate ISP from baculovirus-infected Sf9 cells. The isolated material was separated by SDS-PAGE (10%) under reducing conditions, and the isolated band containing ISP transferred to a PVDF membrane for microsequencing (Edman Degradation). As shown below, the sequence obtained was virtually identical to that of gp67 from *A. californica* polyhedrosis virus.

| | |
|---|---|
| Obtained sequence: | (A) E H () N () QM K T () (P) Y |
| | . . . |
| | . . . |
| | . . . |
| gp67 from *A. californica:* | A E H C N AQM K T G P Y |

These results confirm that ISP is in fact gp67, a result consistent with biochemical purification of gp67 and its associated anti-viral activity. The independent nature of the methods used to isolate ISP clearly defined gp67 as the anti-viral agent in baculovirus infected Sf9 supernatants.

Example 3

Induction of IFN-alpha production by monocytes

It is well documented that IFN-alpha inhibits several of the stimulatory effects that IFN-gamma has on monocytes, such as the production of oxidative burst (Garotta et al., Biochem. Biophys. Res. Commun. 14:948 (1986)). To assess whether ISP could stimulate IFN-alpha production by monocytes, supernatants collected from unstimulated and ISP- or IFN-gamma-stimulated monocytes were analyzed in ELISA (Table 2). After one day of ISP treatment, a substantial amount of IFN-alpha was found in the supernatant. Treatment with IFN-gamma did not induce IFN-alpha release.

TABLE 2

IFN-alpha Production (pg/ml) by ISP-Treated Monocytes

| Treatment | Day +1 | Day +3 | Day +5 |
|---|---|---|---|
| None | 0 | 0 | 0 |
| IFN-gamma (50 U/ml) | 0 | 0 | 0 |
| ISP (500 ng/ml) | 840 | 760 | 750 |
| ISP + IFN-gamma | 780 | 1000 | 745 |

Example 4

Induction of IFN-gamma by ISP

The ability of ISP to induce IFN-alpha and IFN-beta raised the possibility that it may also induce IFN-gamma. The following experiments were carried out to address the question of whether ISP can induce IFN-gamma production by human PBMC.

The positive control in the experiment was IL-12 which is considered a potent inducer of IFN-gamma. FIG. 7 clearly shows that ISP induces IFN-gamma in a dose-dependent manner with maximal induction occurring at a 1/400 dilution of the reference ISP lot. Significant IFN induction is also evident at 1/4000, a concentration at which the previously documented anti-viral effects of ISP are seen. The amount of IFN-gamma induced by ISP is comparable to that seen with IL-12 (1 ng/ml). Most interestingly, the ability of ISP to induce IFN-gamma appears dependent on the presence of L-12 as evidenced by the ability of a monoclonal anti-IL-12 antibody to inhibit the effects of ISP (FIG. 8). Also shown in FIG. 8 is a control in which ISP was incubated at 100° C. for 20 minutes. Such treatment destroys the ability of ISP to induce IFN-gamma.

Example 5

Anti-Viral Activity of ISP In Vivo

In this example, the anti-viral activity of ISP was tested in vivo to determine if it provides systemic resistance to EMCV viral challenge. Accordingly, C57B116NCr mice were treated ISP, mIFNgamma, hIFNgamma or hIFNalphaA/D, and all were challenged with a lethal dose of EMCV virus. The results of this experiment clearly demonstrate that 60–80% of the mice treated with mIFNgamma (FIG. 9A), hIFNalphaA/D (FIG. 9B), or ISP (FIG. 9C) were fully protected from the cytopathic effects of EMCV. On a mg/kg basis, all three proteins displayed comparable protective activities.

The ability of ISP and IFN to protect mice from the lethal effects of EMCV raises several questions regarding the mechanism(s) by which these proteins confer resistance. In theory, these compounds should not interfere with the ability of the host to mount a EMCV-specific immune response that would protect them from subsequent infection. Alternatively, ISP and IFN impose transient anergic states in which the host is protected but unable to generate an effective immune response. To investigate these possibilities, we have subjected previously protected mice to a second lethal dose of EMCV. If ISP, mIFNgamma, and hIFNalpha A/D protect and allow the host to mount a normal virus-specific immune response, then previously protected mice should survive a secondary EMCV challenge. If, on the other hand, these compounds provide transient protection that inhibits the expected immune response, then previously protected mice should succumb to a second lethal injection of virus.

Figure 10A:
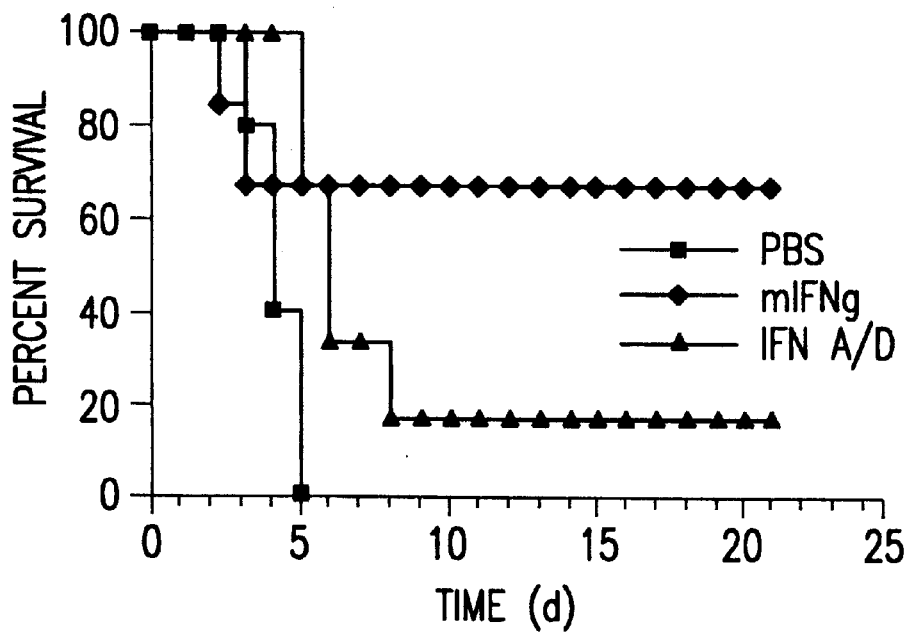
FIGS. 10A and 10B are graphs depicting the duration of the anti-viral effect of ISP, mIFN-gamma and human IFN-alpha A/D.
Figure 10B:
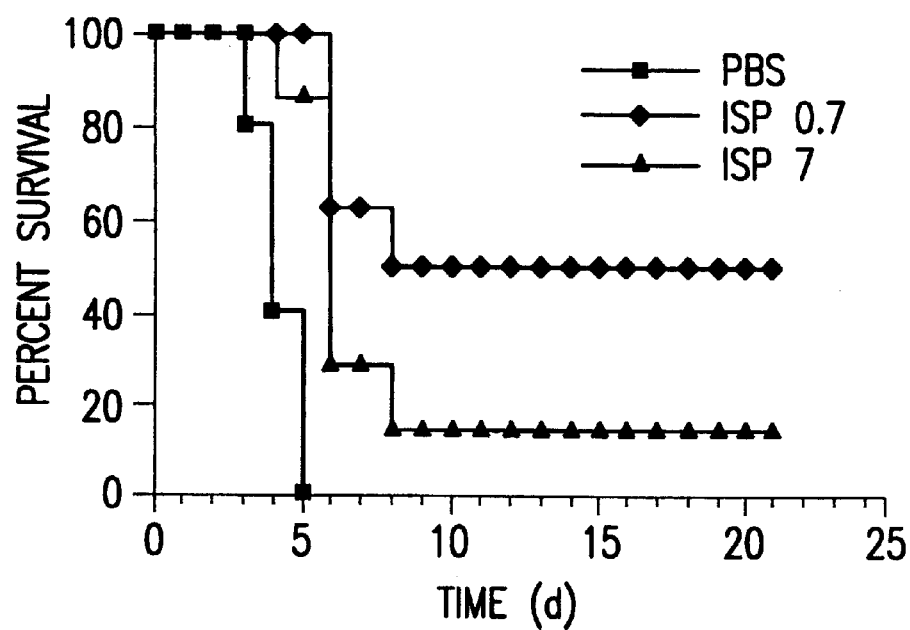
Figure 11A:
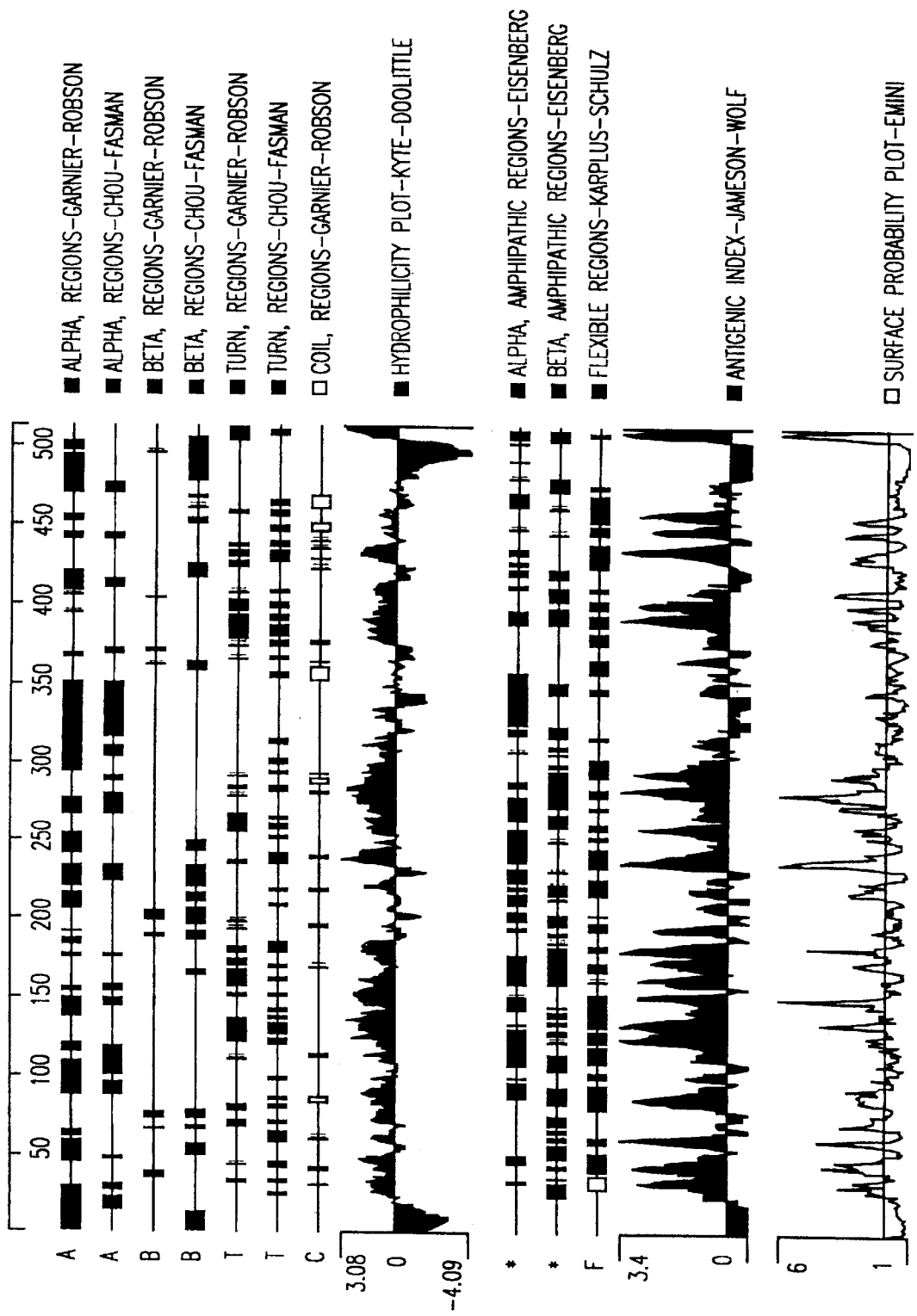
FIGS. 11A and 11B shows a structural analysis of the ISP polypeptides depicted in FIG. 1A and FIG. 1B, respectively. Alpha, beta, turn and coil regions; hydrophilicity and hydrophobicity; amphipathic regions; flexible regions; antigenic index and surface probability were identified using the default settings of the indicated computer progragm.
Figure 11B:
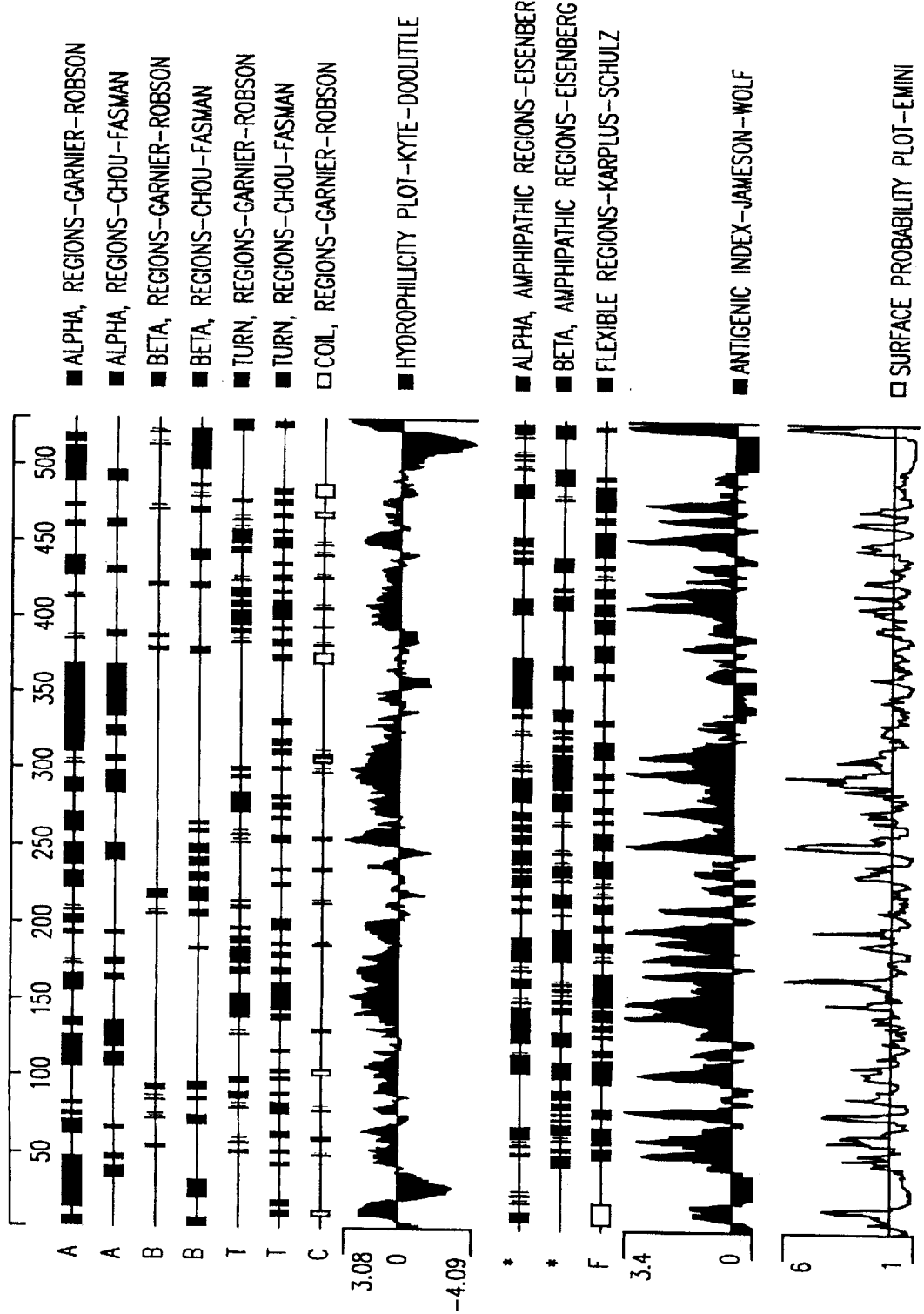

As shown in FIG. 10A, 67% (⅘) of mice protected with mIFNgamma survived a secondary EMCV challenge. In contrast, only 16% (⅙) of hINFalpha A/D treated mice survived similar treatment. Survival of ISP protected mice (FIG. 10B) seemed to be inversely proportional to the original dose of protein, with 50% (⅜) protection observed among mice treated with the low dose (0.7 mg/injection), and 14% (⅐) protection observed in the group receiving the high (7.0 mg/injection) dose of ISP. All mice (⅗) in a control group given PBS (instead of a protective protein) died within 5 days of virus exposure. These results suggest that mIFNgamma and ISP can provide long-lasting protection but do so with only 50–60% efficiency.

The experiments described herein demonstrate that intraperitoneal administration of as little as 0.07 mg/kg of ISP protects 80% of mice from an otherwise lethal injection of murine encephalomyocarditis virus (EMCV). On a mg-kg basis this activity is comparable to that observed in parallel experiments using the known anti-viral agents mIFNgamma, and hIFNalphaA/D. However, unlike hIFNalphaA/D. ISP-induced protection is apparently long-lived as evidenced by the ability of mice previously treated with ISP to survive a secondary EMCV challenge without administration of additional ISP. Taken together, these observations suggest that ISP is a potent anti-viral agent that may be of potential therapeutic value in the treatment of relevant human viral infections.

It will be clear that the invention may be practiced otherwise than as particularly described in the foregoing description and examples.

Numerous modifications and variations of the present invention are possible in light of the above teachings and, therefore, within the scope of the appended claims, the invention may be practiced otherwise than as particularly described.

The entire disclosure of all publications (including patents, patent applications, journal articles, laboratory manuals, books, or other documents) cited herein are hereby incorporated by reference.

What is claimed is:

1. A method for stimulating the production of interferon in a patient comprising administering to a patient in need of elevated levels of interferon. an effective amount of a pharmaceutical composition selected from the group consisting of:

(a) the complete ISP polypeptide having the amino acid sequence shown in SEQ ID NO:2 as residues 1 to 51 and a pharmaceutically acceptable carrier;

(b) the mature ISP polypeptide having the amino acid sequence shown in SEQ ID NO:2 as residues 22 to 511, and a pharmaceutically acceptable carrier;

(c) the extracellular domain of the ISP polypeptide having the amino acid sequence show%n in SEQ ID NO:2 as residues 22 to 487, and a pharmaceutically acceptable carrier;

(d) a fragment of the ISP polypeptide having the amino acid sequence shown in SEQ ID NO:2, wherein said fragment has ISP activity, and a pharmaceutically acceptable carrier:

(e) the complete ISP polypeptide having the amino acid sequence shown in SEQ ID NO:4 as residues 1 to 530 and a pharmaceutically acceptable carrier;

(f) the ISP polypeptide having the amino acid sequence shown in SEQ ID NO:4 as residues 39 to 506, and a pharmaceutically acceptable carrier;

(g) the extracellular domain of the ISP polypeptide having the amino acid sequence shown in SEQ ID NO:4 as residues 39 to 523, and a pharmaceutically acceptable carrier: and (h) a fragment of the ISP polypeptide having the amino acid sequence shown in SEQ ID NO4, wherein said fragment has ISP activity, and a pharmaceutically acceptable.

2. A method of treating infection in a patient comprising administering to a patient in need of such therapy an effective amount of a pharmaceutical composition selected from the group consisting of:

(a) the complete ISP polypeptide having the amino acid sequence shown in SEQ ID NO:2 as residues 1 to 511 and a pharmaceutically acceptable carrier;

(b) the mature ISP polypeptide having the amino acid sequence shown in SEQ ID NO:2 as residues 22 to 511 and a pharmaceutical acceptable carrier;

(c) the extracellular domain of the ISP polypeptide having the amino acid sequence shown in SEQ ID NO:2 as residues 22 to 487, and a pharmaceutically acceptable carrier;

(d) a fragment of the ISP polypeptide having the amino acid sequence shown in SEQ ID NO:2, wherein said fragment has ISP activity and a pharmaceutically acceptable carrier;

(e) the complete ISP polypeptide having the amino acid sequence shown in SEQ ID NO:4 as residues 1 to 530 and a pharmaceutically acceptable carrier;

(f) the ISP polypeptide having the amino acid sequence shown in SEQ ID NO:4 as residues 39 to 506, and a pharmaceutically acceptable carrier;

(g) the extracellular domain of the ISP polypeptide having the amino aid sequence shown in SEQ ID NO:4 as residues 39 to 523, and a pharmaceutically acceptable carrier; and (h) a fragment of the ISP polypeptide having the amino acid sequence shown in SEQ ID NO:4, wherein said fragment has ISP activity, and a pharmaceutically acceptable.

3. The method of claim 2, wherein the infection is of viral, bacterial, or parasitic origin.

4. The method of claim 3, wherein the infection is of viral origin.

5. The method of claim 1, wherein the pharmaceutical composition is (a).

6. The method of claim 1, wherein the pharmaceutical composition is (b).

7. The method of claim 1, wherein the pharmaceutical composition is (c).

8. The method of claim 1, wherein the pharmaceutical composition is (d).

9. The method of claim 1, wherein the pharmaceutical composition is (e).

10. The method of claim 1, wherein the pharmaceutical composition is (f).

11. The method of claim 1, wherein the pharmaceutical composition is (a).

12. The method of claim 1, wherein the pharmaceutical composition is (h).

13. The method of claim 2, wherein the pharmaceutical composition is (a).

14. The method of claim 2, wherein the pharmaceutical composition is (b).

15. The method of claim 2, wherein the pharmaceutical composition is (c).

16. The method of claim 2, wherein the pharmaceutical composition is (d).

17. The method of claim 2, wherein the pharmaceutical composition is (e).

18. The method of claim 2, wherein the pharmaceutical composition is (f).

19. The method of claim 2, wherein the pharmaceutical composition is (g).

20. The method of claim 2, wherein the pharmaceutical composition is (h).

* * * * *

UNITED STATES PATENT AND TRADEMARK OFFICE
CERTIFICATE OF CORRECTION

PATENT NO. : 6,001,806
DATED : December 14, 1999
INVENTOR(S) : Hilbert et al.

It is certified that error appears in the above-identified patent and that said Letters Patent is hereby corrected as shown below:

On the title page, item:

[73], please delete "Humn Genome Sciences, Inc.", and replace therefor --Human Genome Sciences, Inc.,--.

In claim 1, at column 57, line 65, please delete "of interferon. an effective", and replace therefor --of interferon an effective--.

In claim 1, at column 59, line 2, please delete "show%n", and replace therefor --shown--.

In claim 1, at column 59, line 23, please delete "acceptable.", and replace therefor --acceptable carrier.--.

In claim 2, at column 59, line 33, please delete "pharmaceutical", and replace therefor --pharmaceutically--.

In claim 2, at column 59, line 44, please delete "NO4", and replace therefor --NO: 4--.

In claim 11, at column 60, line 27, please delete "is (a).", and replace therefor --is (g).--.

Signed and Sealed this

Twenty-third Day of January, 2001

Attest:

Q. TODD DICKINSON

*Attesting Officer*           *Commissioner of Patents and Trademarks*